(12) United States Patent
Zhang et al.

(10) Patent No.: US 12,195,732 B2
(45) Date of Patent: *Jan. 14, 2025

(54) DIRECT CLONING

(71) Applicant: Gene Bridges GMBH, Heidelberg (DE)

(72) Inventors: Youming Zhang, Heidelberg (DE); Jun Fu, Dresden (DE); Adrian Francis Stewart, Dresden (DE)

(73) Assignee: Gene Bridges GMBH, Heidelberg (DE)

( * ) Notice: Subject to any disclaimer, the term of this patent is extended or adjusted under 35 U.S.C. 154(b) by 1236 days.

This patent is subject to a terminal disclaimer.

(21) Appl. No.: 16/563,274

(22) Filed: Sep. 6, 2019

(65) Prior Publication Data

US 2020/0283759 A1   Sep. 10, 2020

Related U.S. Application Data

(63) Continuation of application No. 13/806,086, filed as application No. PCT/IB2011/052549 on Jun. 10, 2011, now Pat. No. 10,443,051.

(30) Foreign Application Priority Data

Jun. 10, 2010  (GB) ..................... 1009732

(51) Int. Cl.
*C12N 15/10* (2006.01)
*C12N 9/22* (2006.01)
*C12N 15/90* (2006.01)

(52) U.S. Cl.
CPC .......... *C12N 15/1096* (2013.01); *C12N 9/22* (2013.01); *C12N 15/10* (2013.01); *C12N 15/1093* (2013.01); *C12N 15/902* (2013.01); *C12Y 301/16* (2013.01)

(58) Field of Classification Search
CPC ...... C12N 15/1096; C12N 9/22; C12N 15/10; C12N 15/1093; C12N 15/902; C12Y 301/16
See application file for complete search history.

(56) References Cited

U.S. PATENT DOCUMENTS

| | | | |
|---|---|---|---|
| 6,355,412 B1 | 3/2002 | Stewart et al. | |
| 6,509,156 B1 | 1/2003 | Stewart et al. | |
| 10,443,051 B2 * | 10/2019 | Zhang ................. | C12N 15/902 |
| 2003/0017594 A1 | 1/2003 | Youming et al. | |
| 2007/0155014 A1 | 7/2007 | Bertolini et al. | |
| 2013/0210681 A1 | 8/2013 | Zhang et al. | |

FOREIGN PATENT DOCUMENTS

| | | |
|---|---|---|
| CN | 1373803 | 10/2002 |
| EP | 395398 | 10/1990 |
| JP | 2003526376 | 9/2003 |
| JP | 2011217736 A * | 11/2011 |
| WO | 9641008 | 12/1996 |
| WO | 9929837 | 6/1999 |
| WO | 0026396 | 5/2000 |
| WO | 0104288 | 1/2001 |
| WO | 2001004288 | 1/2001 |
| WO | 02062988 | 8/2002 |
| WO | 03010322 | 2/2003 |
| WO | 2004067753 | 8/2004 |
| WO | 2007123636 | 11/2007 |
| WO | 2009104094 | 8/2009 |

OTHER PUBLICATIONS

Murphy, Kenan C. "Lambda Gam protein inhibits the helicase and chi-stimulated recombination activities of *Escherichia coli* RecBCD enzyme." Journal of bacteriology 173.18 (1991): 5808-5821 (Year: 1991).*

Wang, Junping, et al. "An improved recombineering approach by adding RecA to λ red recombination." Molecular biotechnology 32.1 (2006): 43-53 (Year: 2006).*

Wagner, Markus, and Ulrich H. Koszinowski. "Mutagenesis of viral BACs with linear PCR fragments (ET recombination)." Bacterial Artificial Chromosomes: vol. 2 Functional Studies (2004): 257-268 (Year: 2004).*

Zhang, Youming, et al. "DNA cloning by homologous recombination in *Escherichia coli*." Nature biotechnology 18.12 (2000): 1314-1317 (Year: 2000).*

"Genbank Accession No. L23927", accessed from http://www.ncbi.nlm.nih.gov, Sep. 28, 2016.

"Genbank Accession No. M24905", http://www.ncbi.nlm.nih.gov, Sep. 28, 2016.

"SwissProt P15032", accessed from http://www.uniprot.org/uniprot, Sep. 28, 2016.

U.S. Appl. No. 13/806,086 , "Advisory Action", May 16, 2018, 12 pages.

U.S. Appl. No. 13/806,086 , "Final Office Action", Jun. 7, 2016, 12 pages.

U.S. Appl. No. 13/806,086 , "Final Office Action", Mar. 10, 2015, 16 pages.

U.S. Appl. No. 13/806,086 , "Final Office Action", Oct. 4, 2016, 21 Pages.

U.S. Appl. No. 13/806,086 , "Final Office Action", Dec. 20, 2017, 22 pages.

(Continued)

*Primary Examiner* — Nancy J Leith
*Assistant Examiner* — Kyle T Rega
(74) *Attorney, Agent, or Firm* — Kilpatrick Townsend & Stockton LLP

(57) ABSTRACT

A method for performing homologous recombination between at least a first nucleic acid molecule and a second nucleic acid molecule which share at least one region of sequence homology. A method for improving the efficiency of homologous recombination.

8 Claims, 21 Drawing Sheets

Specification includes a Sequence Listing.

(56) References Cited

OTHER PUBLICATIONS

U.S. Appl. No. 13/806,086, "Non-Final Office Action", Sep. 19, 2014, 14 Pages.
U.S. Appl. No. 13/806,086, "Non-Final Office Action", Jun. 29, 2017, 16 pages.
U.S. Appl. No. 13/806,086, "Non-Final Office Action", Oct. 2, 2015, 17 pages.
U.S. Appl. No. 13/806,086, "Non-Final Office Action", Jan. 10, 2019, 21 pages.
U.S. Appl. No. 13/806,086, "Notice of Allowance", May 23, 2019, 10 pages.
U.S. Appl. No. 13/806,086, "Restriction Requirement", Apr. 22, 2014, 8 pages.
Angrand, "Simplified generation of targeting constructs using ET recombination", Nucleic Acids Research, vol. 27, No. 17, Sep. 1999, 6 pages.
Bhargava et al., "Direct cloning of genomic DNA by recombinogenic targeting method using a yeast-bacterial shuttle vector, pClasper", Genomics, vol. 62, No. 2, Dec. 1, 1999, pp. 285-288.
Bio-Rad, "CE Oligonucleotide Analysis Kit", Instruction Manual, Catalog No. 148-4140, URL:http:jjwww.bio-rad.comjLifeSciencejpdf/ Bulletin 9543.pdf, May 4, 1999, 14 pages.
Bolivar et al., "Construction and characterization of new cloning vehicle. II. A multipurpose cloning system", Gene, vol. 2, No. 2, Nov. 1977, pp. 95-113.
Bradshaw et al., "A new vector for recombination-based cloning of large DNA fragments from yeast artificial chromosomes", Nucleic Acids Research, vol. 23, No. 23, 1995, pp. 4850-4856.
Bubeck et al., "Rapid cloning by homologous recombination in vivo", Nucleic Acids Research, vol. 21, No. 15, 1993, pp. 3601-3602.
CA2,802, 167, "Office Action", Sep. 26, 2018, 6 pages.
Chang et al., "Construction and characterization of amplifiable multicopy DNA cloning vehicles derived from the P15A cryptic miniplasmid", Journal of Bacteriology, vol. 134, No. 3, Jun. 1978, pp. 1141-1156.
Chang et al., "Structure and function of the *Escherichia coli* RecE protein, a member of the RecB nuclease domain family", The Journal of Biological Chemistry 276(49), Dec. 7, 2001, pp. 46004-46010.
Chartier et al., "Efficient generation of recombinant adenovirus vectors by homologous recombination in *Escherichia coli*.", Journal of Virology, vol. 70, Jul. 1996, pp. 4805-4810.
Chu et al., "Suppression of a Frameshift Mutation in the recE Gene of *Escherichia coli* K-12 Occurs by Gene Fusion", Journal of Bacteriology, vol. 171, No. 4, Apr. 1989, pp. 2101-2109.
Clark et al., "Genes of the RecE and ReeF pathways of conjugational recombination in *Escherichia coli*", Cold Spring Harbor Symposia on Quantitative Biology, vol. 49, 1984, pp. 453-462.
Clark et al., "Genetic and molecular analyses of the C-terminal region of the recE gene from the Rac prophage of *Escherichia coli* K-12 reveal the recT gene.", Journal of Bacteriology, vol. 175, No. 23, Dec. 1993, pp. 7673-7682.
Datsenko et al., "One-step inactivation of chromosomal genes in *Escherichia coli* K-12 using PCR products", Proceedings of the National Academy of Sciences, vol. 97, No. 12, 2000, pp. 6640-6645.
Degryse, "In vivo intermolecular recombination in *Escherichia coli*: application to plasmid constructions.", Gene, vol. 170, No. 1, Apr. 17, 1996, pp. 45-50.
Deluca et al., "Analysis of the recE Locus of *Escherichia coli* K-12 by Use of Polyclonal Antibodies to Exonuclease VIII", J. Bact 170(12), 1998, 5797-5805 Pages.
Ellis et al., "High efficiency mutagenesis, repair, and engineering of chromosomal DNA using single-stranded oligonucleotides", Proceedings of the National Academy of Sciences, vol. 98, No. 12, 2001, pp. 6742-6746.
EP16192084.8, "Extended European Search Report", Jan. 27, 2017, 13 pages.

Fu et al., "Efficient transfer of two large secondary metabolite pathway gene clusters into heterologous hosts by transposition", Nucleic Acids Research, vol. 36, No. 17, 2008, 14 pages.
Gibson et al., "Creation of a Bacterial Cell Controlled by a Chemically Synthesized Genome", Science, vol. 329, No. 5987, Jul. 2, 2010, pp. 52-56.
Hall et al., "Identification and Characterization of the *Escherichia coli* RecT Protein, a Protein Encoded by the recE Region That Promotes Renaturation of Homologous Single-Stranded DNA", Journal of Bacteriology, vol. 175, No. 1, Jan. 1993, pp. 277-287.
Handa et al., "Type III Restriction Is Alleviated by Bacteriophage (RecE) Homologous Recombination Function but Enhanced by Bacterial (RecBCD) Function", Journal of Bacteriology, vol. 187, No. 21, Nov. 2005, pp. 7362-7373.
Hashimoto-Gotoh et al., "Mutations of temperature sensitivity in R plasmid pSC101", Journal of Bacteriology, vol. 131, No. 2, Aug. 1977, pp. 405-412.
Joseph et al., "Exonuclease VI11 of *Escherichia coli* I. Purification and Physical Properties", Journal of Biological Chemistry vol. 258, No. 17, 1983, pp. 10411-10417.
JP2016-093169, "Office Action", 7 pages.
Kitagawa et al., "Complete set of ORF clones of *Escherichia coli* ASKA library (A Complete Set of *E. coli* K-12 ORF Archive): Unique Resources for Biological Research", DNA Research 12, 2005, pp. 291-299.
Kolodner et al., "Homologous Pairing Proteins Encoded By the *Escherichia coli* RECE and RECT Genes", Molecular Microbiology, vol. 11, No. 1,, Jan. 1, 1994, pp. 23-30.
Kovall et al., "Toroidal structure of lambda-exonuclease", Science, vol. 277, No. 5333, Sep. 19, 1997, pp. 1824-1827.
Kulkarni et al., "Interaction between the sbcC gene of *Escherichia coli* and the gam gene of phage lambda", Genetics, vol. 123, No. 2, Oct. 1989, pp. 249-253.
Larionov et al., "Direct Isolation of Specific Chromosomal Regions and Entire Genes by TAR Cloning", Genetic Engineering, vol. 21, 1999, pp. 37-55.
Low, "Restoration by the rac locus of recombinant forming ability in recB—and recC—merozygotes of *Escherichia coli* K-12", Molecular and General Genetics 122(2), 1973, pp. 119-130.
Mahajan et al., "Physical analysis of spontaneous and mutagen-induced mutants of *Escherichia coli* K-12 expressing DNA exonuclease VIII activity", Genetics 125(2), Jun. 1990, pp. 261-273.
Murphy et al., "Lambda Gam protein inhibits the helicase and chi-stimulated recombination activities of *Escherichia coli* RecBCD enzyme.", Journal of Bacteriology, vol. 173, 1991, pp. 5808-5821.
Murphy et al., "PCR-mediated gene replacement in *Escherichia coli*", Gene, vol. 246, No. 1-2, Apr. 4, 2000, pp. 321-330.
Muyrers et al., "ET-cloning: think recombination first", Genetic Engineering, vol. 22, Jan. 1, 2000, pp. 77-98.
Muyrers et al., "Point mutation of Bacterial Artificial Chromosome by ET recombination", EMBO Reports, 2000, pp. 239-243.
Muyrers et al., "Rapid Modification of Bacterial Artificial Chromosomes by ET-Recombination", Nucleic Acid Research, vol. 27, No. 6, Mar. 1999, pp. 1555-1557.
Muyrers et al., "RecE/RecT and Red/Red initiate double-stranded break repair by specifically interacting with their respective partners", Genes & Development, vol. 14, 2000, pp. 1971-1982.
Muyrers et al., "Recombination between linear double-stranded DNA substrates in vivo", Academic Press Inc, New York, vol. 387, No. 1, Apr. 1, 2009, pp. 139-141.
Muyrers et al., "Techniques: Recombinogenic Engineering-New Options for Cloning and Manipulating DNA", Trends in Biochemical Sciences, vol. 26, No. 5, May 2001, pp. 325-331.
Narayanan et al., "Efficient and precise engineering of a 200 kb beta-globin human/bacterial artificial chromosome in *E. coli* DH10B using an inducible homologous recombination system.", Gene Therapy, vol. 6, No. 3, 1999, pp. 442-447.
Oliner et al., "In vivo cloning of PCR products in *E.coli*", Nucleic Acids Research, vol. 21, No. 22, 1993, pp. 5192-5197.
Olsen et al., "Cellular responses to targeted genomic sequence modification using single-stranded oligonucleotides and zinc-finger nucleases", DNA Repair, Elsevier, Amsterdam, NL., vol. 8, No. 3, Mar. 1, 2009, pp. 298-308.

(56) References Cited

OTHER PUBLICATIONS

PCT/IB2011/052549, "International Search Report and Written Opinion", Dec. 8, 2011, 25 pages.

Penfold et al., "An improved suicide vector for construction of chromosomal insertion mutations in bacteria", Gene, vol. 118, No. 1, Sep. 1, 1992, pp. 145-146.

Puchta et al., "Homologous recombination in plant cells is enhanced by in vivo induction of double strand breaks into DNA by a site-specific endonuclease", Nucleic Acids Research, Oxford University Press, Surrey, GB., vol. 21, No. 22, Nov. 11, 1993, pp. 5034-5040.

Rivera-Muller et al., "Assisted large fragment insertion by Red/ET-recombination (ALFIRE)—an alternative and enhanced method for large fragment recombineering", Nucleic Acids Research, vol. 35, No. 1, 2007, 8 pages.

Schmidt et al., "CapSelect: A highly sensitive method for 5' CAP-dependent enrichment of full-length cDNA in PCR-mediated analysis of mRNAs", Nucleic Acids Research, vol. 27, No. 21, 1999.

Shashikant et al., "Recombinogenic targeting: a new approach to genomic analysis—a review", Gene, vol. 223, No. 1-2, Nov. 26, 1998, pp. 1998.

Siegl et al., "I-SceI endonuclease: a new tool for DNA repair studies and genetic manipulations in streptomyces", Applied Microbiology and Biotechnology, vol. 87, No. 4, May 15, 2010, pp. 1525-1532.

Smith, "Homologous recombination in procaryotes", Microbiological Reviews 52(1), 1988, pp. 1-28.

Swingle et al., "Oligonucleotide recombination in Gram-negative bacteria", Molecular Microbiology, vol. 75, No. 1, 2009, pp. 138-148.

Wang et al., "An improved recombineering approach by adding RecA to λ Red recombination", Molecular Biotechnology, vol. 32, No. 1, 2006, pp. 43-54.

Willis et al., "Mutation-dependent suppression of recB21 recC22 by a region cloned from the Rac prophage of *Escherichia coli* K-12", Journal of Bacteriology, vol. 162, No. 3, Jun. 1985, pp. 1166-1172.

Yanisch-Perron et al., "Improved M13 phage cloning vectors and host strains: nucleotide sequences of the M13mp18 and pUC19 vectors", Gene. vol. 33, No. 1, 1985, pp. 103-119.

Yu et al., "An efficient recombination system for chromosome engineering in *Escherichia coli*", Proceedings of the National Academy of Sciences, vol. 97, No. 11, 2000, pp. 5978-5983.

Zhang et al., "A new logic for DNA engineering using recombination in *Escherichia coli*", Nature Genetics, vol. 20, No. 2, Oct. 1998, pp. 123-128.

Zhang et al., "Crystal structure of *E. coli* RecE protein reveals a toroidal tetramer for processing double-stranded DNA breaks", Structure, vol. 17, No. 5, May 13, 2009, pp. 690-702.

Zhang et al., "DNA Cloning by Homologous Recombination in *Escherichia coli*", Nature Biotechnology, vol. 18(12), Dec. 2000, pp. 1314-1317.

Zhang et al., "Phage Annealing Proteins Promote Oligonucleotide-Directed Mutagenesis in *Escherichia coli* and Mouse ES Cells", BMC Molecular Biology, vol. 4, Jan. 2003, pp. 1-14.

\* cited by examiner

| gene | Swap70 | Tmem56 | Xist | hMeCP2 |
|---|---|---|---|---|
| restriction site | BstZ17I | AfeI/NaeI | NcoI/SnaBI | NaeI/PmlI |
| 5' end to HA (bp) | 2778 | 5052 | 1817 | 503 |
| 3' end to HA (bp) | 2554 | 5770 | 553 | 59 |
| colony number | 53 | 29 | 91 | 38 |
| | 95 | 31 | 111 | 63 |
| correct recombinants | 12/18 | 7/18 | 11/18 | 14/18 |
| | 12/18 | 7/18 | 15/18 | 16/18 |

DIRECT CLONING

CROSS-REFERENCE TO RELATED APPLICATIONS

This application is a continuation of U.S. application Ser. No. 13/806,086, filed Mar. 27, 2013, which is a national stage application under 35 U.S.C. § 371 of International Application No. PCT/IB2011/052549, filed Jun. 10, 2011, which in turn claims priority to United Kingdom Patent Application No. 1009732.7 filed Jun. 10, 2010, the contents of each of which is hereby incorporated by reference into this application in its entirety.

REFERENCE TO A "SEQUENCE LISTING" SUBMITTED AS ASCII TEXT FILE VIA EFS-WEB

The Sequence Listing written in file 098430-1153795-000410US-SequenceListing.txt created on May 22, 2020, 7,872 bytes, machine format IBM-PC, MS-Windows operating system, in accordance with 37 C.F.R. §§ 1.821 to 1.825, is hereby incorporated by reference in its entirety for all purposes.

The standard procedure for cloning of DNA fragments from DNA mixtures, such as genomic DNA or cDNA preparations, involves purifying the DNA from protein, lipids and other contaminants and ligation of this DNA preparation, usually after restriction digestion, onto a cloning vector to make a library. Because libraries are usually complex mixtures of cloned DNA pieces, the retrieval of a specific DNA piece requires screening the library in one of several ways, each of which is laborious. Often the specific DNA piece is not contained within a single clone and needs to be reconstructed from two or more clones or is accompanied by undesired flanking sequences that need to be removed. These extra subcloning steps further add to the laborious nature of cloned DNA library methodologies.

As human diseases become more fully understood, the development of patient specific therapies will become more prevalent, including the development of patient-specific gene correction methods. Ideally, patient-specific gene correction will employ the problematic DNA region obtained from the patient, corrected in the laboratory and re-inserted into the patient.

Furthermore, the development of next generation sequencing technologies (e.g. 454, Solexa or SOLiD4) allows the acquisition of genome sequencing data without genomic library construction. This approach has been termed 'metagenomics' and now vast amounts of genome sequence data, which can be complete in the case of prokaryotic genomes, is known for many species without the accompanying genomic library resources. However functional studies require the acquisition and manipulation of cloned DNA encoding the gene(s) to be studied. Hence there is a need for a new technology to directly clone specific DNA regions from genomic DNA pools into a vector, which is referred to herein as 'direct cloning'.

Furthermore there is a growing demand for assembly of linear DNA pieces in synthetic biology. These linear DNAs could be ssDNA, preferably oligonucleotides, or dsDNA. Synthetic biology assembly of DNA pieces has been used to create genes, operons, chromosomes and recently, an entire genome (see reference 42). The assembly methods, which often involve more than 10 different DNA molecules, have employed conventional DNA ligation or homologous recombination mediated by the Red operon or the endogenous machinery in the yeast *Saccharomyces cerevisiae*. Thus there is a growing need to explore new ways to assemble DNA pieces in a defined order.

Direct cloning and sub-cloning by homologous recombination, also termed 'cloning by gap repair' or 'linear to linear' has been described before (1-4). The term "cloning" refers to methods whereby a DNA fragment is amplified from an original source by ligation to a vector and propagation in a host cell, usually *E. coli* or yeast. The term "subcloning" refers to methods whereby a DNA fragment that has already been amplified from an original source, either by previous cloning or by PCR, is propagated in a host cell. In addition to previous descriptions of direct cloning, subcloning applications of linear to linear homologous recombination have also been described (for example, see cloning kits CLONEEZ® PCR Cloning Kit; or Cold Fusion Cloning Kit). Current methods for subcloning by homologous recombination are not very efficient. However high efficiencies are not required because the substrate DNA fragments are essentially pure before subcloning.

Direct cloning of genes from genomic DNA preparations has been achieved using yeast (8-12). However the method is technically challenging and the subsequent cloned DNA molecules are genetically unstable because recombination in yeast cannot be controlled. Consequently direct cloning in yeast is almost exclusively confined to one laboratory (V. Larionov—see Selective isolation of mammalian genes by TAR cloning. Kouprina N, Larionov V. Curr Protoc Hum Genet. 2006 May; Chapter 5: Unit 5.17). A previous attempt to commercialize this yeast technology failed (Biotech company "Caliper" in Boston closed in 2002).

*E. coli* sbcA strains are very efficient for linear to circular homologous recombination, which is referred to herein as "LCHR", due to the expression of the rac phage proteins, RecE and RecT (5-7). Because RecE and RecT are homologous to the equivalent lambda phage proteins, Red alpha and Red beta, Red alpha and Red beta were also shown to mediate very useful and efficient homologous recombination. Linear to linear homologous recombination, which is referred to herein as "LLHR", is also greatly increased by expression of either RecE/RecT or Redalpha/Redbeta.

Homologous recombination mediated by RecE/RecT currently uses a truncated version of RecE. The original RecE discovered by AJ Clark is a 279 amino acids long 5' to 3' exonuclease (RecE588) (see reference 5). A shorter version by 14 amino acids at the 5' end (RecE602) also conveys LCHR and LLHR activities. This version has been crystallized (Structure. 2009 May 13; 17 (5): 690-702. Crystal structure of *E. coli* RecE protein reveals a toroidal tetramer for processing double-stranded DNA breaks.), and is equivalent to the similarly sized 5' to 3' exonuclease, Red alpha. These forms of RecE are truncated versions of the original rac phage gene, which is 866 amino acids long. The shorter form of RecE (RecE602) corresponds to the last approximately 265 amino acids. In other words, the full-length RecE has an additional 601 amino acid at its N-terminus compared to the truncated RecE602, whereas the full-length RecE has an additional 587 amino acids at its N-terminus compared to the truncated RecE588.

It has been shown that genes from DNA pools can be cloned into a linear vector in one step in *E. coli* mediated by RecET recombination (7). However, this system is too inefficient to be routinely applied for direct cloning from genomic DNA preparations. In particular, it does not allow directly cloning of DNA regions larger than a certain size, which varied with the complexity of the DNA pool. With less complex pools, such as a prokaryotic genomic DNA preparation, the existing technology allows direct cloning of some DNA regions larger than 10 kb. With more complex pools, such as a mammalian genomic DNA preparation, the existing technology allows direct cloning only of shorter DNA regions (around 2 kb) at very low efficiencies.

It is an object of the present invention to improve cloning methodologies. In particular, it is an object of the invention to provide a method of direct cloning which can be used as a method to fish out the gene of interest from a DNA pool.

It is also an object of the present invention to provide an improved method for subcloning.

It is also an object of the present invention to provide improved methods for complex DNA engineering tasks such as assembling multiple DNA pieces into a precise product.

SUMMARY OF THE INVENTION

In a first aspect, the invention provides a method for performing homologous recombination between at least a first nucleic acid molecule and a second nucleic acid molecule which share at least one region of sequence homology, wherein the method comprises bringing the first nucleic acid molecule into contact with the second nucleic acid molecule in the presence of a 5' to 3' exonuclease and an annealing protein;
  wherein the 5' to 3' exonuclease comprises a region having 5' to 3' exonuclease activity and at least:
  i) amino acids 564-587 of SEQ ID NO:1; or
  ii) a 24 amino acid sequence having at least 70% identity to amino acids 564-587 of SEQ ID NO:1 over the entire length of the 24 amino acid sequence.

Preferably, the 5' to 3' exonuclease is full length RecE.

In a second aspect, there is provided a method for improving the efficiency of homologous recombination by performing homologous recombination in the presence of at least one single stranded oligonucleotide that has no sequence homology to the nucleic acid molecules undergoing homologous recombination, wherein the efficiency of homologous recombination is improved relative to when homologous recombination is performed in the absence of the at least one single stranded DNA oligonucleotide.

In a third aspect, there is provided a method for performing homologous recombination between at least a first nucleic acid molecule and a second nucleic acid molecule which share at least one region of sequence homology, comprising, prior to performing homologous recombination in vivo, the step of linearising at least one circular nucleic acid molecule in vivo using a rare-cutting sequence specific DNA cleaving enzyme to generate the first and/or the second nucleic acid molecule.

DETAILED DESCRIPTION OF THE INVENTION

It has surprisingly been found that homologous recombination can be mediated using a RecE which comprises part of the endogenous N-terminal RecE sequence that is not present in the truncated RecE used in existing homologous recombination technology. Moreover, it has surprisingly been found that the efficiency of LLHR is increased by using such an N-terminally extended RecE. The highest efficiencies of LLHR have been obtained using full length RecE and so the invention preferably involves the use of full length RecE to mediate LLHR. The amino acid sequence of full length RecE from *E. coli* K12 is set out below (SEQ ID NO:1):

MSTKPLFLLRKAKKSSGEPDVVLWASNDFESTCATLDYLIVKSGKKLSSY

FKAVATNFPVVNDLPAEGEIDFTWSERYQLSKDSMTWELKPGAAPDNAHY

QGNTNVNGEDMTEIEENMLLPISGQELPIRWLAQHGSEKPVTHVSRDGLQ

ALHIARAEELPAVTALAVSHKTSLLDPLEIRELHKLVRDTDKVFPNPGNS

NLGLITAFFEAYLNADYTDRGLLTKEWMKGNRVSHITRTASGANAGGGNL

TDRGEGFVHDLTSLARDVATGVLARSMDLDIYNLHPAHAKRIEEIIAENK

PPFSVFRDKFITMPGGLDYSRAIVVASVKEAPIGIEVIPAHVTEYLNKVL

TETDHANPDPEIVDIACGRSSAPMPQRVTEEGKQDDEEKPQPSGTTAVEQ

GEAETMEPDATEHHQDTQPLDAQSQVNSVDAKYQELRAELHEARKNIPSK

NPVDDDKLLAASRGEFVDGISDPNDPKWVKGIQTRDCVYQNQPETEKTSP

DMNQPEPVVQQEPEIACNACGQTGGDNCPDCGAVMGDATYQETFDEESQV

EAKENDPEEMEGAEHPHNENAGSDPHRDCSDETGEVADPVIVEDIEPGIY

YGISNENYHAGPGISKSQLDDIADTPALYLWRKNAPVDTTKTKTLDLGTA

FHCRVLEPEEFSNRFIVAPEFNRRTNAGKEEEKAFLMECASTGKTVITAE

EGRKIELMYQSVMALPLGQWLVESAGHAESSIYWEDPETGILCRCRPDKI

IPEFHWIMDVKTTADIQRFKTAYYDYRYHVQDAFYSDGYEAQFGVQPTFV

FLVASTTIECGRYPVEIFMMGEEAKLAGQQEYHRNLRTLSDCLNTDEWPA

IKTLSLPRWAKEYAND

Existing homologous recombination technology mediated by RecE/RecT currently uses a truncated version of RecE, which consists of the C-terminal end of RecE (amino acids 588-866 of SEQ ID NO:1). The use of a truncated version of RecE consisting of amino acids 602-866 of SEQ ID NO:1 has also been described (see references 7, 13, 14, 16, 17, 18 and 36) as have RecE proteins consisting of amino acids 595-866 of SEQ ID NO: 1 and 606-866 of SEQ ID NO:1 (see reference 14). These truncated versions of RecE are referred to herein as "truncated RecE". These truncated RecE proteins have been shown to comprise a region having 5' to 3' exonuclease activity (see reference 14).

The use of truncated RecE as used in existing homologous recombination technology is specifically excluded from the scope of the first aspect of the invention. Specifically, the use of a RecE consisting of the sequence set out in amino acids 588-866, 595-866, 602-866 or 606-866 of SEQ ID NO:1 is specifically excluded from the scope of the first aspect of the invention.

Thus, in a first aspect, the invention provides a method for performing homologous recombination between at least a first nucleic acid molecule and a second nucleic acid molecule which share at least one region of sequence homology, wherein the method comprises bringing the first nucleic acid molecule into contact with the second nucleic acid molecule in the presence of a 5' to 3' exonuclease and an annealing protein;
  wherein the 5' to 3' exonuclease comprises a region having 5' to 3' exonuclease activity and at least:
  i) amino acids 564-587 of SEQ ID NO:1; or
  ii) a 24 amino acid sequence having at least 70% identity (e.g. at least 75%, 80%, 85%, 90%, 95%, 98% or 99%) to amino acids 564-587 of SEQ ID NO: 1 over the entire length of the 24 amino acid sequence.

The 5' to 3' exonuclease used in a method of the first aspect of the invention comprises a region having 5' to 3' exonuclease activity. Preferably, this region having 5' to 3' exonuclease activity is derived from RecE but in some embodiments, the region having 5' to 3' exonuclease is derived from Redalpha or from any other 5' to 3' exonuclease.

In embodiments in which the region having 5' to 3' exonuclease activity is derived from RecE, the region having 5' to 3' exonuclease activity comprises or consists of amino acids 588-866 of SEQ ID NO: 1 or a variant thereof. Preferably, the region comprising 5' to 3' exonuclease activity consists of amino acids 588-866 of SEQ ID NO:1. In some embodiments, the variant comprises a sequence having at least 70% identity (for example at least 80%, at least 85%, at least 90%, at least 95%, at least 98% or at least 99%) to amino acids 588-866 of SEQ ID NO:1 across the length of amino acids 588-866 of SEQ ID NO:1. The variant of the region comprising 5' to 3' exonuclease activity may in some embodiments comprise truncations from or additions to the C-terminal and/or N-terminal end. For example, the region comprising 5' to 3' exonuclease activity of RecE may comprise 1, 2, 3, 4, 5, less than 10, less than 20, less than 30, less than 40 or less than 50 amino acid deletions, additions or substitutions at the C-terminal and/or N-terminal end. Any deletions or additions are preferably at the C-terminal end. Such deletions or additions are preferably not at the N-terminal, but such deletions or additions are envisaged in certain circumstances. In the case of additions, in some embodiments the additional sequences are not from SEQ ID NO:1. Internal deletions or additions may also be useful in certain circumstances.

It has been found that homologous recombination may be mediated by a RecE that, in addition to the previously used region having 5' to 3' exonuclease activity, also comprises at least the 24 amino acids immediately N-terminal to this region, i.e. amino acids 564-587 of SEQ ID NO:1.

Preferably, the additional sequence recited in options i) and ii) of a method of the first aspect of the invention is immediately N-terminal to the region having 5' to 3' exonuclease activity.

Preferably, the 5' to 3' exonuclease is a RecE. In some embodiments, the RecE comprises or consists of amino acids 564-866 of SEQ ID NO:1 or a variant thereof comprising or consisting of a sequence 303 amino acids in length that has at least 70% sequence identity (e.g. at least 75%, 80%, 85%, 90%, 95%, 98% or 99%) to SEQ ID NO: 1 over the entire length of the 303 amino acid sequence. In some embodiments, the RecE additionally comprises an N-terminal methionine residue.

More preferably, the RecE comprises further endogenous N-terminal sequence of RecE. For example, the RecE comprises at least 50, 100, 150, 200, 250, 300, 350, 400, 450, 500, 550, 560, 570, 580, 581, 582, 583, 584, 585, 586 or 587 amino acids immediately N-terminal to the region comprising 5' to 3' exonuclease activity, wherein these additional amino acids correspond to the corresponding amino acids from SEQ ID NO: 1 or from a variant of SEQ ID NO:1 having at least 70% sequence identity (e.g. at least 75%, 80%, 85%, 90%, 95%, 98% or 99%) to SEQ ID NO:1 over the entire length of the sequence.

In some embodiments, the RecE comprises or consists of a sequence selected from the group consisting of amino acids 1-866, 141-866, 423-866 or 564-866 of SEQ ID NO:1 or a variant of a sequence from this group, wherein the variant has at least 70% sequence identity to SEQ ID NO:1 over the entire length of the sequence. In some embodiments, the variant includes an additional N-terminal methionine immediately N-terminal to the recited sequence.

In a most preferred embodiment, the RecE is full length RecE. Preferably, the full length RecE comprises or consists of amino acids 1-866 of SEQ ID NO:1. In some embodiments, the full length RecE comprises or consist of amino acids 1-866 of a variant of SEQ ID NO:1, wherein the variant of SEQ ID NO:1 has at least 70% sequence identity (e.g. at least 75%, 80%, 85%, 90%, 95%, 98% or 99%) to SEQ ID NO: 1 over the entire length of the sequence.

A reference to a percentage sequence identity between two amino acid sequences means that, when aligned, that percentage of amino acids are the same in comparing the two sequences.

In some embodiments, the RecE is a RecE as described above, but which comprises truncations from or additions to the N-terminal and/or C-terminal end. For example, the RecE may comprise 1, 2, 3, 4, 5, less than 10, less than 20, less than 30, less than 40 or less than 50 amino acid deletions or additions at the N-terminal and/or C-terminal end. In the case of additions, in some embodiments the additional sequences are not from SEQ ID NO:1. Internal deletions or additions may also be useful in certain circumstances.

In some embodiments, the 5' to 3' exonuclease is a Red alpha or any other 5' to 3' exonuclease to which at least amino acids 564-587 of SEQ ID NO:1 or a variant thereof have been attached.

The 5' to 3' exonuclease works in conjunction with an annealing protein to mediate homologous recombination. In some embodiments, the annealing protein used in the method of the first aspect of the invention is a phage annealing protein. Preferably, the annealing protein is RecT (from the rac prophage). More preferably, the annealing protein is RecT and the 5' to 3' exonuclease is RecE (preferably full length RecE). The identification of the recT gene was originally reported by Hall et al., (J. Bacteriol. 175 (1993), 277-287). However, any other suitable annealing protein may be used provided that this cooperates with the 5' to 3' exonuclease that is used. Examples of other suitable phage annealing proteins are provided in WO 02/062988 (Gene Bridges, GmbH). It has surprisingly been found that LLHR can occur in the absence of RecT expression in certain host cells such as *E. coli* strain GB2005, presumably because some endogenous RecT-like activity is present. However, the efficiency of LLHR mediated by full length RecE is significantly increased by the presence of RecT.

It has surprisingly been found that the N-terminal additions to truncated RecE from the endogenous SEQ ID NO:1 sequence increase the efficiency of LLHR compared to when a truncated RecE consisting only of amino acids 602-866 of SEQ ID NO:1 is used. Thus, the at least first and second nucleic acid molecules used in the method of the first aspect of the invention are preferably linear nucleic acid molecules. Indeed, it is particularly preferred to use full length RecE in a method of the first aspect of the invention to mediate LLHR.

However, it is also envisaged that in some embodiments, the first nucleic acid molecule is a linear nucleic acid molecule and the second nucleic acid molecule is a circular nucleic acid molecule. Likewise, it is also envisaged that in some embodiments, the first nucleic acid molecule is a circular nucleic acid molecule and the second nucleic acid molecule is a linear nucleic acid molecule. In some embodiments, the circular nucleic acid molecule is a cloning vector. Examples of suitable cloning vectors for use in the various embodiments of a method of a first aspect of the invention are a p15A origin based vector (see reference 39), a pBR322 origin based vector (see reference 40), a pUC origin based vector (see reference 41), a plasmid, a fosmid, a lambda cloning vector and a BAC (bacterial artificial chromosome).

Surprisingly, it has been found that LLHR and LCHR are quite distinct molecular processes. This was discovered during an examination of the properties of the RecE used in the present invention. It has been found that full length RecE is about one order of magnitude more efficient at mediating LLHR than LCHR. It has also been found that full length RecE/RecT is more efficient at LLHR than Red alpha/Red beta, which in turn is more efficient at LCHR than full length RecE/RecT. Full length RecE is significantly better at LLHR than the previously published truncated RecE. In preferred embodiments, full length RecE/RecT is at least 10 times better, for example, at least 20 times better, at least 50 times better, preferably at least 100 times better than truncated RecE/RecT at mediating LLHR (the efficiency of truncated RecE consisting of amino acids 602-866 of SEQ ID NO:1, as used herein, is representative of the efficiency of homologous recombination mediated by the other truncated RecE proteins used in existing homologous recombination technologies). However, full length RecE is worse at LCHR than the previously published shorter form of RecE.

Until now, it has been assumed that both LCHR and LLHR are mediated by similar proteins. The unexpected differences between LLHR and LCHR and the identification of the advantages of Red alpha/Red beta for LCHR and RecE/RecT for LLHR define a way to improve DNA cloning and engineering methods using the right combinations of the two systems.

Thus, in some embodiments, the at least first and second nucleic acid molecules are linear and the method further comprises using the product of the LLHR reaction between the first and second nucleic acid molecules in a second step of LCHR in the presence of Redalpha and Redbeta or in the presence of truncated RecE and RecT. In some embodiments, the product of the LLHR is linear and the second step involves bringing the linear product into contact with a circular nucleic acid molecule. In some embodiments, the product of the LLHR is circular and the second step involves bringing the circular product into contact with a linear nucleic acid molecule. In preferred embodiments, the first and second nucleic acid molecules are linear and are brought into contact with full length RecE and RecT to mediate LLHR and the method comprises a second step of performing LCHR in the presence of Redalpha and Redbeta and preferably Redgamma. In some embodiments, LLHR between the first and second linear nucleic acid molecules is carried out in vitro. In preferred embodiments, the second step of LCHR is carried out in vivo in a host cell. Thus, in some embodiments, the method involves bringing the linear first nucleic acid molecule into contact with the linear second nucleic acid molecule in vitro, preferably in the presence of the 5' to 3' exonuclease and annealing protein (more preferably RecE and RecT), and then transforming the product of the LLHR reaction into a host cell and carrying out LCHR in vivo in the presence of a further nucleic acid molecule, preferably in the presence of Redalpha and Redbeta and preferably also Redgamma. The in vitro step does not require the presence of Red gamma, but in some embodiments, Red gamma is present.

In some embodiments, the method involves bringing the linear first nucleic acid molecule into contact with the linear second nucleic acid molecule in vitro, preferably in the presence of the 5' to 3' exonuclease and annealing protein (more preferably RecE and RecT), and then transforming the resulting nucleic acid into a host cell and carrying out homologous recombination in vivo in accordance with a method of the present invention. This two step method increases the efficiency of homologous recombination by increasing the likelihood that the first and second nucleic acid molecules will come into contact in the host cell.

Typically, the at least first and second nucleic acid molecules comprise or consist of DNA. However, in some embodiments, the at least first and/or second nucleic acid molecule includes RNA or one or more modified nucleotides.

It has been found that the efficiency of homologous recombination using a method of the first aspect of the invention is increased by carrying out the method in the presence of Red gamma (see references 26 and 30). Red gamma inhibits the RecBCD exonuclease in E. coli. It is advantageous to inhibit RecBCD when performing homologous recombination mediated by RecE/RecT or Redalpha and Redbeta because inhibition of the RecBCD exonuclease protects the linear molecules. Thus, in preferred embodiments, the homologous recombination is carried out in the presence of Red gamma. The presence of Red gamma is particularly preferred when the homologous recombination is carried out in a host cell.

In some embodiments, the method of the invention is carried out in the presence of RecA (see reference 27). RecA is a single stranded binding protein which is the endogenous E. coli counterpart to RecT/Redbeta. DNA transformation works better in the presence of RecA than in the absence of RecA because RecA improves the survival of host cells after electroporation. It is preferred to carry out the method of the present invention in the presence of Red gamma and RecA.

It has surprisingly been found that for LCHR, the starting circular nucleic acid molecule needs to be replicating in order for homologous recombination to take place. Thus, in embodiments of the method which use a plasmid based on the R6K gamma origin and LCHR, the method is preferably carried out in the presence of the Pir protein (see reference 33), for example, in a pir+ host cell. In contrast, for LLHR, the starting linear nucleic acid molecules do not need to be replicating. Thus, in some embodiments in which the method is used to mediate LLHR, the method is carried out in the absence of the Pir protein, for example, in a pir– host cell.

The method of the invention may be effected, in whole or in part, in a host cell. Suitable host cells include cells of many species, including parasites, prokaryotes and eukaryotes, although bacteria, such as gram negative bacteria are a preferred host. More preferably, the host cell is an enterobacterial cell, such as a *Salmonella, Klebsiella, Bacillus, Neisseria, Photorhabdus* or *Escherichia coli* cell (the method of the invention works effectively in all strains of *E. coli* that have been tested). A preferred host cell is *E. coli* K12. It should be noted, however, that the method of the present invention is also suitable for use in eukaryotic cells or organisms, such as fungi, plant or animal cells. The system has been demonstrated to function in mouse ES cells and there is no reason to suppose that it will not also be functional in other eukaryotic cells. Typically, the host cell is an isolated host cell, but the use of non-isolated host cells is also envisaged.

The 5' to 3' exonuclease and/or the annealing protein may be expressed from heterologous DNA in the host cell, for example, from a vector with which the host cell has been transformed. One example of a suitable vector is the pSC101 plasmid (see reference 38) but any other suitable vector may be used. Similarly, one or more or all of Red gamma, RecA, Redalpha and/or Redbeta may be expressed from heterologous DNA in the host cell, as required. Any suitable promoter may be used to drive expression of these proteins. However, the use of an inducible promoter such as an arabinose inducible promoter (e.g. Para-BAD, also known as "pBAD") or a rhamnose inducible promoter (e.g. rhaS-Prha) is particularly preferred for expression of RecE. In embodiments in which the method of the invention is performed in the presence of Red gamma and the 5' to 3' exonuclease is RecE, it is preferred to express RecE under the control of the rhamnose-inducible promoter.

The E. coli K12 host cell comprises an endogenous copy of the full length recE gene and the recT gene in its genome. These are present on a rac prophage that has integrated into the host genome. However, expression of full length RecE does not occur naturally from this integrated gene because this gene is silent. Thus, in embodiments in which the 5' to 3' exonuclease is expressed from heterologous DNA, the method may be carried out in the absence of endogenous RecE activity.

There is also provided a host cell that has been transformed with a nucleic acid that encodes a 5' to 3' exonuclease as described above. Preferably, the 5' to 3' exonuclease is expressed from the nucleic acid and so the invention also provides a host cell that expresses a 5' to 3' exonuclease as recited in a method of the first aspect of the invention. Preferably, the host cell expresses full length RecE. The 5' to 3' exonuclease is preferably under the control of an inducible promoter, such as the rhamnose-inducible promoter (for example, rhaS-Prha) or the arabinose-inducible promoter (such as Para-BAD). These promoters are well known in the art.

However, as an alternative to expressing the 5' to 3' exonuclease (for example, RecE) in a host cell from heterologous DNA, in some embodiments, RecE is expressed from the recE gene of the integrated prophage, wherein the expression of RecE is driven by a heterologous promoter. For example, a heterologous promoter may be inserted upstream of the endogenous copy of the recE gene that is present on the prophage such that it is operably linked to the recE gene. Any suitable promoter may be used. Preferably, the promoter is an inducible promoter, for example, an arabinose-inducible promoter such as Para-BAD. In some embodiments, a rhamnose-inducible promoter is used. In some embodiments, a hyg-araC-pPAB cassette is inserted upstream of the endogenous copy of the recE gene.

Thus, there is also provided a host cell comprising a recE gene from an integrated prophage, wherein the recE gene is under the control of a heterologous promoter. Preferably the promoter is an inducible promoter, for example, an arabinose-inducible promoter such as Para-BAD or a rhamnose-inducible promoter (for example, rhaS-Prha). The host cell is preferably E. coli, more preferably E. coli K12.

A host cell of the invention also preferably comprises a nucleic acid encoding an annealing protein (preferably RecT). The host cell preferably also comprises a nucleic acid encoding Red gamma. In some embodiments, the host cell may also comprise a nucleic acid comprising RecA and/or Redalpha and/or Redbeta. Preferably, the host cell expresses RecE, RecT and Redgamma and optionally RecA. In some embodiments, the host cell additionally expresses Redalpha and Redbeta.

In one embodiment, the host cell expresses RecE, RecT, Redgamma and RecA from the Para-BAD promoter, optionally as an operon. In some embodiments, the RecE, RecT, Redgamma and RecA are expressed from the Para-BAD promoter which replaces ybcC in the chromosome of the E. coli host cell.

It is also envisaged that in some embodiments in which the first and second nucleic acid molecule are linear, the method of the present invention is effected in whole or in part in vitro. For example, a purified 5' to 3' exonuclease and annealing protein (preferably purified RecE and RecT proteins) may be used or the extracts from E. coli cells expressing the 5' to 3' exonuclease and annealing protein may be used. When the method is performed in vitro, it is advantageous to pre-treat the linear first and second nucleic acid molecules to expose the single-stranded homology ends.

Both LCHR and LLHR require regions of shared homologies between the first and second nucleic acid molecules through which homologous recombination occurs. In the case of LLHR, the first nucleic acid molecule must share at least one region of sequence homology with the second nucleic acid molecule. In some embodiments, the first nucleic acid molecule shares one region of sequence homology with the second nucleic acid molecule such that LLHR between the first and nucleic acid molecules results in a linear product. In embodiments in which LLHR takes place between the first and second linear nucleic acids and one or more additional linear nucleic acids to form a linear product, each of the linear nucleic acids shares a region of sequence homology with the linear nucleic acid that will form its neighbour in the linear product of the LLHR reaction. In embodiments in which LLHR takes place between the first and second linear nucleic acids and one or more additional linear nucleic acids to form a circular product, each of the linear nucleic acids shares a region of sequence homology with the linear nucleic acid that will form its neighbour in the circular product of the LLHR reaction. In some embodiments, the first nucleic acid molecule shares two regions of sequence homology with the second nucleic acid molecule such that LLHR between the first and second nucleic acid molecules results in a circular molecule. It will be clear to the person of skill in the art how to design regions of homology such that a linear molecule or a circle is formed.

Preferably, the at least one homology arm is at the very end of each linear fragment. The optimum configuration of these regions of sequence homology or "homology arm(s)" occurs when one homology arm is at the very end of each linear fragment and a different homology arm is at the other end, with these homology arms configured so that recombination creates a circle. LLHR can occur when the homology arms are not terminally located, however the efficiency is reduced. Thus, in preferred embodiments, the at least one regions of homology are located at the very end of one or both ends of the at least first and second nucleic acid molecules. In some embodiments, the regions of homology are located internally on the at least first and/or second nucleic acid molecules. In some embodiments, the regions of homology are located proximal to one or both ends of the at least first and second nucleic acid molecules, for example, such that there are less than 100 nucleotides (e.g. less than 75, less than 50, less than 25, less than 10, less than 5 nucleotides) N-terminal or C-terminal to the homology arms at the N- and C-terminals of the linear nucleic acid molecules, respectively.

It has been found that there is a difference between LLHR and LCHR concerning the minimum length of homology arms required. Under certain circumstances, RecET mediated LLHR requires only 6 bp homology between the first and second nucleic acid molecules, whereas lambda Red-mediated LCHR requires at least 20 bp homology to combine the first and second nucleic acid molecules. Thus, in some embodiments in which the method involves LLHR, the regions of sequence homology are at least 6, at least 10, at least 20 or at least 30 nucleotides in length. For examples, in some embodiments, the regions of sequence homology are 6-6, 6-9, 6-30, 6-100, 10-20, 20-29, 20-40, 20-50, 10-100, 25-30, 25-40, 25-50, 30-40 or 30-50 nucleotides in length. The efficiency of homologous recombination generally increases with the length of the homology arms that are used and so the use of longer homology arms is also envisaged.

By "homology" between a first and a second nucleic acid molecule is meant that when the sequences of the first and a second nucleic acid molecule are aligned, there are a number of nucleotide residues that are identical between the sequences at equivalent positions. Degrees of homology can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

The method of the first aspect of the invention may be used to mediate triple recombination (triple recombination is described in detail in WO 2009/104094, the content of which is incorporated by reference). Thus, in some embodiments, the first and second nucleic acid molecules are linear and the method further comprises bringing a third nucleic acid molecule into contact with the first and second nucleic acid molecules in the presence of the 5' to 3' exonuclease and the annealing protein, wherein the first nucleic acid molecule shares a region of homology with the second nucleic acid molecule and shares a different region of homology with the third nucleic acid molecule, wherein the second nucleic acid molecule shares a region of homology with the first nucleic acid molecule and shares a different region of homology with the third nucleic acid molecule and wherein the third nucleic acid molecule shares a region of homology with the second nucleic acid molecule and shares a different region of homology with the first nucleic acid molecule. In some embodiments of triple recombination, the third nucleic acid molecule is linear. In preferred embodiments of triple recombination, the third nucleic acid molecule is circular. In embodiments in which the third nucleic acid molecule is circular, it is hypothesized that this method involves a step of LLHR between the first and second nucleic acid molecules to form a linear product and a step of LCHR between the linear product and the circular third nucleic acid molecule. Full length RecE together with RecT has been found to mediate triple recombination, although with low efficiency when the third nucleic acid molecule is circular. In some embodiments, recombination between the first and second nucleic acid molecules reconstitutes a selection marker which can then be used to select for correct recombinants. In some embodiments, one or both of the first and second nucleic acid molecules comprise a selection marker. If a selection marker is present on both the first and second nucleic acid molecules, these selection markers are preferably different.

In some embodiments of triple recombination, the first nucleic acid molecule and the second nucleic acid molecule have symmetric dephosphorylated ends. In preferred embodiments of triple recombination, the first nucleic acid molecule and the second nucleic acid molecule have asymmetrically phosphorothioated ends.

In some embodiments, the method of the first aspect of the invention may be used to mediate quadruple recombination (see WO 2009/104094). Thus, in some embodiments, the first and second nucleic acid molecules are linear and the method further comprises bringing a third nucleic acid molecule and a fourth nucleic acid molecule into contact with the first and second nucleic acid molecules in the presence of the 5' to 3' exonuclease and the phage annealing protein, wherein the wherein the first nucleic acid molecule shares a region of homology with the second nucleic acid molecule and shares a different region of homology with the fourth nucleic acid molecule, wherein the second nucleic acid molecule shares a region of homology with the first nucleic acid molecule and shares a different region of homology with the third nucleic acid molecule, wherein the third nucleic acid molecule shares a region of homology with the second nucleic acid molecule and shares a different region of homology with the fourth nucleic acid molecule, and wherein the fourth nucleic acid molecule shares a region of homology with the third nucleic acid molecule and shares a different region of homology with the first nucleic acid molecule. In preferred embodiments of quadruple recombination, the third and fourth nucleic acid molecules are linear. In some embodiments, the third nucleic acid molecule is circular and the fourth nucleic acid molecule is linear.

Quadruple recombination is particularly useful for assembling a complex DNA construct or for cloning a linear sequence of interest into a vector using two oligonucleotides, thereby avoiding the need to PCR the sequence to be cloned. Advantageously, quadruple recombination can be used to clone a sequence of interest which is a long fragment of DNA, such as a fragment of genomic DNA, directly into a cloning vector such as a BAC. The first nucleic acid molecule preferably comprises the sequence of interest. The sequence of interest can be any length, for example, a short synthetic oligonucleotide of less than 150 nucleotides in length, but is preferably 2 kb or more in length (more preferably 2.5 kb or more, 3 kb or more, 5 kb or more, 7 kb or more, 10 kb or more, 15 kb or more, 16 kb or more, 20 kb or more, 25 kb or more, 30 kb or more, 40 kb or more). For example, in some embodiments, the sequence of interest is 2-100 kb in length (for example, 2-75 kb, 4-50 kb, 4-25 kb, 5-15 kb, 7-10 kb, 15-100 kb, 15-75 kb, 20-75 kb, 25-50 kb, 40-100 kb, 40-75 kb in length).

In preferred embodiments of quadruple recombination, the third nucleic acid molecule is a linearised cloning vector, for example, it may be a linearised BAC. In other embodiments, the third nucleic acid molecule is a circular nucleic acid molecule. In some embodiments of quadruple recombination, the second and fourth nucleic acid molecules are short oligonucleotides (for example, of 150 nucleotides or less, 120 nucleotides or less, 100 nucleotides or less, 80 nucleotides or less, 60 nucleotides or less or 50 nucleotides or less in length). In a preferred embodiment of quadruple recombination, the first nucleic acid molecule comprises a sequence of interest, the second and fourth nucleic acid molecules are short oligonucleotides and the third nucleic acid molecule is a cloning vector, more preferably a linearised cloning vector.

Triple and quadruple recombination may advantageously be mediated by full length RecE. In some embodiments, triple or quadruple recombination is mediated by full length RecE in the absence of Redalpha and Redbeta.

A method of triple recombination or quadruple recombination as described above in which the third nucleic acid molecule is circular may advantageously be carried out in a host cell that comprises both the RecE/RecT proteins and the Redalpha/Redbeta proteins. Such a host cell is provided by the present invention. In preferred embodiments, the RecE gene is under the control of a different promoter from the Redalpha/Redbeta genes such that the different genes can be independently temporally expressed. For example, in some embodiments, there is provided a host cell comprising Redalpha, Redbeta and optionally Red gamma under the control of a first inducible promoter (for example, an arabinose-inducible promoter such as Para-BAD) and RecE, preferably a phage annealing (most preferably RecT), and optionally Red gamma under the control of a second inducible promoter (for example, a rhamnose-inducible promoter such as rhaS-Prha). In some embodiments, RecA is also expressed from one or both promoters. Advantageously, the host cell may be derived from a GB2005 E. coli host cell (see reference 25) as this contains Redalpha, Redbeta and Red gamma under the control of the Para-BAD promoter on the E. coli chromosome. Preferably, the RecE expressed by these host cells is full length RecE. The use of such a host cell is advantageous for methods which utilize a step of LLHR and a step of LCHR. Advantageously, such a host is useful for cloning large segments of bacterial genomes, for example operons for the production of secondary metabolites.

In some embodiments, a method of triple recombination or quadruple recombination may be a two step method wherein LLHR between the first and second nucleic acid molecule in the case of triple recombination or LLHR between the fourth, first and second nucleic acid molecules in the case of quadruple recombination is carried out in vitro in the presence of a 5' to 3' exonuclease as described herein and a suitable annealing protein (preferably RecE and RecT), and the second step of bringing together the product of the LLHR and the circular third nucleic acid molecule is carried out in a host cell in the presence of Redalpha and Redbeta to mediate LCHR.

In some embodiments, the method of the invention involves zipping multiple linear molecules together to form a circular molecule, for example, a circular plasmid. For example, the method may further comprise bringing at least one (for example, one, two, three, four, five, six, seven, eight, nine, ten, or more than ten) additional linear nucleic acid molecules into contact with the first and second nucleic acid molecules in the presence of the 5' to 3' exonuclease and the annealing protein, wherein each of the nucleic acid molecules shares a region of homology with the nucleic acid molecule that will form its neighbour in the resulting circular product and performing LLHR in accordance with a method of the invention.

In some embodiments, a method according to the first aspect of the invention is used for insertion or integration of a DNA sequence into a circular target. In some embodiments, a method according to the first aspect of the invention is used for subcloning of a DNA sequence from a circular target. In some embodiments, a method according to the first aspect of the invention is used for cloning of a DNA sequence from a linear target. In some embodiments, a method according to the first aspect of the invention is used for oligo repair.

In some embodiments of the first aspect of the invention, the first nucleic acid molecule and/or second nucleic acid molecules are single stranded linear nucleic acid molecules. For example, in some embodiments in which the first and second nucleic acid molecules are linear (and so the method is used to mediate LLHR), the first and/or second nucleic acid molecules are single stranded. The single stranded nucleic acid is preferably synthesized as an oligonucleotide which is less than 180 nucleotides in length (for example, 150 nucleotides or less, 130 nucleotides or less, 110 nucleotides or less, 100 nucleotides or less, 80 nucleotides or less, 60 nucleotides or less or 55 nucleotides or less). Such embodiments are useful for introducing a mutation (for example, a point mutation such as a substitution, an insertion or a deletion) into the sequence of the second nucleic acid molecule. The single stranded nucleic acid molecule preferably comprises the sequence of the lagging strand. In other embodiments, the single stranded nucleic acid comprises the sequence of the leading strand. The strand is defined as leading or lagging according to the replication orientation in the target molecule (typically the second nucleic acid molecule). In some embodiments, the first and/or second nucleic acid molecules are double stranded.

Advantageously, LLHR performed by a method of the first aspect of the invention may be used to generate a cDNA library. This method utilizes in part the "PlugOligo" method that is known in the art (see reference 37). The method of generating a cDNA library preferably involves generating a first nucleic acid molecule by:

i) bringing a 3' oligonucleotide having a run of T nucleotides into contact with one or more mRNA sequences of interest such that the 3' oligonucleotide anneals to the polyA tail; wherein the 3' oligonucleotide comprises sequence 3' to the run of T nucleotides which shares a region of homology with the cloning vector for use in generating the library;

ii) reverse transcribing the complementary cDNA from the mRNA;

iii) bringing a 5' oligonucleotide (the "PlugOligo") having a run of G nucleotides into contact with the product of ii) such that the run of G nucleotides anneals to the run of C nucleotides that have been added onto the end of the cDNA sequence, wherein the 5' oligonucleotide provides template sequence 5' to the run of G nucleotides for extension of first strand synthesis, which shares a region of homology with the cloning vector for use in generating the library and also a 3' phosphate, wherein the region of homology in i) and the region of homology in iii) are different; and iv) removing the PlugOligo and priming second strand synthesis from the 5' end of the second region of homology to generate double stranded cDNA which has the two homology regions at each end.

The first nucleic acid molecule (the double stranded cDNA of iv)) is brought into contact with the second nucleic molecule (preferably a linearised cloning vector) in accordance with this embodiment of the first aspect of the invention. Thus, in a preferred embodiment of the method of this embodiment, the double stranded cDNA of iv) and the linearised cloning vector are the first and second nucleic acid molecules as described in the method of the first aspect of the invention.

Advantageously, a method of LLHR of the present invention may be used to subclone a sequence of interest from a BAC. Preferably, in such embodiments, the first nucleic acid molecule is a linearised BAC comprising the sequence of interest and the second nucleic acid molecule is a linearised cloning vector. The BAC is preferably linearised (for example, with a restriction enzyme) such that the sequence of interest remains intact. The present invention substantially addresses the very difficult problems involved with direct cloning of DNA from complex mixtures, and therefore it also describes a greatly improved method for the much simpler task of subcloning.

In some embodiments, the first nucleic acid molecule is linear and comprises a phosphorothioation proximal to its 5' end and a phosphorothioation proximal to its 3' end. By "proximal to" is meant at the end or close to the end of the nucleic acid molecule, for example, within the 5' 200 nt, 100 nt, 50 nt or 25 nt. In some embodiments, the 5' phosphorothioation is of the first nucleotide after the homology region and the 3' phosphorothioation is of the first nucleotide before the homology region. In some embodiments, the 5' phosphorothioation is of the 51st nucleotide from the 5' end of the first nucleic acid sequence and the 3' phosphorothioation is of the 51st nucleotide from the 3' end of the first nucleic acid sequence. In some embodiments, the two or more linear nucleic acid molecules have asymmetrically phosphorothioated ends. The use of phosphorothioation to create asymmetric linear nucleic acid molecules is discussed in detail in WO 2009/104094, the contents of which is incorporated by reference. Advantageously, when the first nucleic acid molecule is phosphorothioated as described above, the second nucleic acid molecule is linear and comprises a phosphorothioation proximal to its 3' end.

In some embodiments, at least one of the nucleic acid molecules comprises a selectable marker which allows for the selection of correct recombinants. In some embodiments, recombination results in a selectable marker being reconstituted. Any suitable selectable marker may be used in the present invention. In some embodiments, the selectable marker is an antibiotic resistance gene, for example, an antibiotic resistance gene selected from the group consisting of kanamycin resistance, chloramphenicol resistance, ampicillin resistance and blasticidin resistance.

In some embodiments, a counter-selectable marker may be used. For example, the ccdB counter-selectable marker may be used to reduce the background recombination when performing direct cloning according to a method of the invention. In some embodiments, a counter-selectable marker is used such that incorrect recombinants (for example, from self-circularisation of the first or second nucleic acid molecule) result in expression of the counter-selectable gene, whereas correct recombinants prevent expression of the counter-selectable gene. A gene whose expression product is toxic to the host cell is a useful counter-selectable marker. An example of such a gene is ccdB.

In some embodiments, a counter-selectable marker and a selectable marker are used in a method of the invention.

The at least first and second nucleic acid molecule may be derived from any suitable for source. For example, the at least first and second nucleic acid molecules may comprise a nucleic acid sequence from a eukaryote or a prokaryote. In some embodiments, the first and/or second nucleic acid molecule is genomic DNA. Typically, the genomic DNA is a fragment of genomic DNA. The genomic DNA preferably comprises a sequence of interest. In some embodiments, the fragment of genomic DNA is obtained by shearing or digesting genomic DNA (for example, with restriction enzymes) such that the sequence of interest remains intact. In some embodiments, the first and/or second nucleic acid molecule is a member of a cDNA library. In some embodiments, the first and/or second nucleic acid molecule is obtained from a BAC. In some embodiments, the first and/or second nucleic acid molecule (for example, the fragment of genomic DNA, member of a cDNA library or fragment derived from a BAC) comprises a sequence of interest of 2 kb or more in length (for example, 2.5 kb or more, 4 kb or more, 5 kb or more, 7.5 kb or more, 10 kb or more, 15 kb or more, 20 kb or more, 25 kb or more, 40 kb or more, 50 kb or more, 75 kb or more or 100 kb or more in length). In some embodiments, the first and/or second nucleic acid molecule (for example, the fragment of genomic DNA, member of a cDNA library or fragment derived from a BAC) comprises of consists of a sequence of interest of 2-150 kb in length (for example, 5-100 kb, 7.5-75 kb, 10-50 kb, 15-25 kb, 15-75 kb, 40-100 kb or 40-75 kb in length). Preferably, the sequence of interest is the entire region between the homology arms at either end of the first and/or second nucleic acid molecule. For example, the first and/or second nucleic acid molecule may comprise a sequence of interest which comprises or consists of a gene cluster such as a gene cluster encoding a secondary metabolite pathway or a fatty acid synthesis pathway. In embodiments in which the first nucleic acid molecule is a fragment of genomic DNA, the second nucleic acid molecule is preferably a linearised cloning vector, such as a linearised BAC.

In embodiments in which the first nucleic acid molecule is a fragment of genomic DNA, the method may comprise generating the first nucleic acid molecule by digesting or shearing genomic DNA to obtain a linear fragment of genomic DNA comprising a sequence of interest (preferably the first nucleic acid molecule), followed by co-electroporating the linear fragment of genomic DNA (preferably the first nucleic acid molecule) into a host cell together with a linear cloning vector (preferably the second nucleic acid molecule), thereby bringing the first nucleic acid molecule into contact with the second nucleic acid molecule. The second nucleic acid molecule preferably comprises a selectable marker. In order to increase the number of correct recombinants obtained, in some embodiments the method may advantageously further comprise selecting for correct recombinants using the selectable marker and electroporating the resistant colonies with a further linear DNA molecule encoding a second selectable gene flanked by homology arms corresponding to part of the intended cloned region, followed by selecting for correct colonies that grow after selection for the second selectable marker.

Preferably, the first nucleic acid molecule is linear and comprises a sequence of interest and the second nucleic acid molecule is a cloning vector. In some embodiments, the cloning vector is circular. In preferred embodiments, the cloning vector has been linearised.

In some embodiments, a method of the first aspect of the invention may be used to directly clone a region of DNA from a human or non-human animal, for example, for use in health studies or for regenerative therapies through correction by gene targeting. For example, in some embodiments, the first nucleic acid molecule comprises or consists of a fragment of genomic DNA from a human or non-human animal. The fragment of genomic DNA may comprise a sequence of interest such as a gene comprising a mutation, wherein the mutation leads to a disease or disorder and correction of the mutation to the wild type sequence treats or prevents the disease or disorder. In some embodiments, the fragment of genomic DNA may comprise the wild type sequence of a gene. In some embodiments, the first nucleic acid molecule comprises a fragment of genomic DNA comprising the wild type sequence of a gene and the second nucleic acid molecule is a host cell chromosome. Such a method may advantageously be used for treatment or prevention of a disease or disorder by gene targeting. However, in some embodiments, a method for treatment of the human or animal body by surgery or therapy is specifically excluded from the scope of the invention. Advantageously, there is provided a first nucleic acid molecule in accordance with this embodiment of the invention for use in a method of treatment or prevention of a disease or a disorder by gene targeting, wherein the second nucleic acid molecule with which the first nucleic acid molecule undergoes homologous recombination is a host cell chromosome.

There is provided a kit for use in a method of the first aspect of the present invention. In some embodiments, the kit comprises a nucleic acid encoding a 5' to 3' exonuclease, as described herein. In some embodiments, the kit comprises a 5' to 3' exonuclease, as described herein. Preferably, the 5' to 3' exonuclease is RecE and more preferably, the RecE is full length RecE. More preferably, the kit comprises a host cell as described herein. For example, in some embodiments, the host cell in the kit comprises a nucleic acid encoding a RecE as described herein under the control of a heterologous promoter and an annealing protein, preferably RecT. In some embodiments, the host cell also comprises a nucleic acid encoding Red gamma. In some embodiments, the host cell expresses RecE, RecT and preferably Red gamma. The kit may also comprise one or more pre-prepared linear vectors.

Another preferred application of a method of the first aspect of the invention involves the assembly of linear nucleic acid molecules, preferably linear DNA, in synthetic biology. Thus, in some embodiments, the first and second nucleic acid molecules are linear and the method further comprises bringing the first and second nucleic acid molecules into contact with one or more additional linear nucleic acid molecules (for example, 1, 2, 3, 4, 5, 6, 7, 8, 9, at least 10, at least 25, at least 50 additional nucleic acids) in the presence of the 5' to 3' exonuclease and the annealing protein to produce a linear product. In some embodiments, one or more or all of the linear nucleic acids molecules are single stranded. Preferably, one or more or all of the nucleic acid molecules are oligonucleotides or double stranded DNA. In preferred embodiments, homologous recombination between the first and second nucleic acids and the one or more additional nucleic acids results in the production of a gene, an operon, a chromosome or an entire genome. Synthetic biology assembly of DNA nucleic acids has been used to create genes, operons, chromosomes and recently an entire genome (see reference 42). The assembly methods currently used have employed conventional DNA ligation or homologous recombination mediated by the Red operon or the endogenous machinery in the yeast *Saccharomyces cereviseae*. The improved performance defined here based on RecE will become a method of choice for synthetic biology DNA assemblies in commerce and research.

It has also surprisingly been found that the efficiency of LLHR mediated by RecE and RecT can be increased by spiking the reaction mixture with at least one single stranded DNA oligonucleotide that has no shared sequence homology with the nucleic acid sequences undergoing recombination. This single stranded DNA oligonucleotide spike increases the efficiency of LLHR mediated by the truncated RecE used in existing LLHR technologies and by the N-terminally extended RecE used in the first aspect of the invention compared to when LLHR is carried out in the absence of the single stranded DNA oligonucleotide. The molecular basis for this improvement remains unknown. However, it has surprisingly been found that the addition of single stranded oligonucleotides phenocopies the additional LLHR efficiency conveyed by the N-terminally extended version of RecE described above.

Thus, in a second aspect, there is provided a method for improving the efficiency of homologous recombination by performing homologous recombination in the presence of at least one single stranded oligonucleotide that has no sequence homology to the nucleic acid molecules undergoing homologous recombination, wherein the efficiency of homologous recombination is improved relative to when homologous recombination is performed in the absence of the at least one single stranded oligonucleotide.

By "no sequence homology" is meant a level of sequence homology that is less than that required to effect homologous recombination between two nucleic acid sequences. Thus, the single stranded oligonucleotide does not contain any region of sequence identity to the nucleic acid molecules undergoing homologous recombination that is greater than 6 nucleotides in length.

Typically, the at least one single stranded oligonucleotide comprises or consists of DNA. However, in some embodiments, the at least one single stranded oligonucleotide includes RNA or one or more modified nucleotides.

In some embodiments, the at least one single stranded oligonucleotide is 10-100 nucleotides in length. For example, in some embodiments, the at least one single stranded oligonucleotide is 10-80, 10-70, 20-70, 20-60, 30-60, 30-50, 35-45, 38-42 or 39-41 nucleotides in length. Preferably, the at least one single stranded oligonucleotide is 40 nucleotides in length.

Generally, multiple copies of the at least one single stranded oligonucleotide are present. In some embodiments, two or more (for example, three, four, five, ten, fifteen, twenty or more) different single stranded oligonucleotides are used. These two or more different single stranded oligonucleotides may differ in sequence and/or in length.

A method of homologous recombination according to the second aspect of the invention may take place in a host cell or may take place in vitro. Similar considerations apply to the choice of host cell as for the method of the first aspect of the invention. An example of a preferred host cell is *E. coli* K12, for example, GB2005.

Any suitable concentration of the at least one single stranded oligonucleotide may be used. In some embodiments in which homologous recombination takes place in a host cell and is introduced into the host cell by electroporation, the at least one single stranded oligonucleotide is used at a concentration of 1-200 pmol (for example, 20-150 pmol, 75-150 pmol, 85-120 pmol, 95-105 pmol, 98-102 pmol, 99-101 pmol) for each electroporation. The use of 100 pmol per electroporation is preferred. In a preferred embodiment the at least one single stranded oligonucleotide is 40 nucleotides in length and is used at 100 pmol per electroporation.

The homologous recombination performed in the method of the second aspect of the invention may be mediated by an endogenous mechanism in the host cell, for example, an endogenous mechanism in GB2005. For example, it has surprisingly been found that co-transformation of the at least one single stranded oligonucleotide with a first and second nucleic acid molecule sharing two regions of sequence homology into the GB2005 host cell increases the LLHR efficiency by 10 fold in the absence of expression of RecE and RecT or Redalpha and Redbeta compared to when the first and second nucleic acid molecule are co-transformed into the host cell in the absence of the at least one single stranded oligonucleotide.

In preferred embodiments, the method of the second aspect of the invention may be mediated by any suitable 5' to 3' exonuclease and annealing protein. In some embodiments of a method of the second aspect of the invention, the homologous recombination is mediated by RecE and a phage annealing protein. The phage annealing protein is preferably RecT. In some embodiments, RecE is a truncated RecE as used in existing methods of homologous recombination. For example, in some embodiments, the RecE used in the method of the second aspect of the invention comprises the 5' to 3' exonuclease activity of RecE but does not comprise any N-terminal sequence from amino acids 1-587 of SEQ ID NO:1. For example, in some embodiments, the RecE used in a method of the second aspect of the invention is selected from a RecE consisting of amino acids 588-866, 595-866, 597-866, 602-866 or 606-866 of SEQ ID NO:1.

In some embodiments, the method of homologous recombination performed in the second aspect of the invention is a method of homologous recombination as described in the first aspect of the invention. All embodiments described for the first aspect of the invention may be applied to the second aspect of the invention. Thus, in some embodiments, the RecE used in the method of the second aspect of the invention is a RecE as used in a method of the first aspect of the invention. The use of a RecE comprising or consisting of 564-866 of SEQ ID NO:1 is particularly preferred. In some embodiments, full length RecE is used.

In other embodiments, the homologous recombination performed in the method of the second aspect of the invention is mediated by Redalpha and Redbeta. However, it has been found that the addition of the at least one single stranded oligonucleotide increases the efficiency of homologous recombination mediated by full length RecE and RecT much more than it increases the efficiency of homologous recombination mediated by Redalpha and Redbeta.

In a preferred embodiment of a method of the second aspect of the invention, the method comprises performing homologous recombination in the presence of full length RecE, RecT, Red gamma, RecA and at least one single stranded oligonucleotide that has no sequence homology to the nucleic acid molecules undergoing homologous recombination. In such embodiments, expression of RecE is preferably under the control of a rhamnose-inducible promoter. A host cell for carrying out such a method is also provided.

In some embodiments, a method of the second aspect of the invention is used to mediate LLHR. In some embodiments, a method of the second aspect of the invention is used to mediate LCHR. In some embodiments, a method of the second aspect of the invention is used to mediate LLHR and LCHR.

A kit is provided for performing a method of homologous recombination according to the second aspect of the invention. A kit for performing a method of the second aspect of the invention comprises at least one single stranded oligonucleotide as described above. Preferably, the kit also comprises one or more nucleic acid molecules encoding RecE, RecT and optionally Red gamma. In some embodiments, the kit also comprises one or more nucleic acid molecules encoding Redalpha and Redbeta. In some embodiments, the nucleic acid molecules are in the form of expression vectors suitable for transformation into a host cell. In other embodiments, the kit comprises a host cell that comprises these nucleic acid molecules. In some embodiments, the kit comprises a host cell that expresses RecE, RecT and optionally Red gamma and/or which expresses Redalpha and Redbeta. In some embodiments, the kit is the CLONEEZ® PCR Cloning Kit or the Cold Fusion Cloning Kit which additionally comprises the at least one single stranded oligonucleotide as described above. In some embodiments, a kit for performing a method of homologous recombination is a kit for use in a method of the first aspect of the present invention, as described above, which additionally comprises the at least one single stranded oligonucleotide.

It has also surprisingly been found that it is possible to increase the efficiency of homologous recombination by generating linear nucleic acid molecules in vivo which then undergo homologous recombination in vivo (i.e. in the host cell in which the linear nucleic acid molecule was generated). As detailed above, it has been observed that under some conditions LLHR can be performed with greater efficiency than LCHR. In some examples of homologous recombination, for example ex vivo homologous recombination, LLHR can be performed simply by providing linear nucleic acid molecules in the presence of a 5' to 3' exonuclease and an annealing protein. This approach may also be used for in vivo homologous recombination methods, but to do so requires the transformation of the linear molecules into the host cell in which homologous recombination is to occur. The approach is therefore limited by the fact that transformation of linear molecules typically occurs at a frequency of $10^4$-fold lower than the corresponding circular molecule.

In order to overcome the limitation in the transformation efficiency of linear molecules which prevents the full exploitation of the advantages of this form of homologous recombination in vivo, the inventors have developed a method of producing linear nucleic acid molecules in vivo, using a rare-cutting sequence specific DNA cleaving enzyme, which may then be used in in vivo methods of homologous recombination. This step of generating linear nucleic acid molecules in vivo is therefore particularly advantageous because it avoids the loss in efficiency resulting from the low efficacy of transformation of cells with linear fragments, while simultaneously permitting the exploitation of the higher frequency of homologous recombination resulting from recombination involving linear fragments.

Thus, in a third aspect, there is provided a method for performing homologous recombination between at least a first nucleic acid molecule and a second nucleic acid molecule which share at least one region of sequence homology, comprising, prior to performing homologous recombination in vivo, the step of linearising at least one circular nucleic acid molecule in vivo using a rare-cutting sequence specific DNA cleaving enzyme to generate the first and/or the second nucleic acid molecule.

In some embodiments of the third aspect, the step of linearising the at least one circular nucleic acid molecule in vivo using a rare-cutting sequence specific DNA cleaving enzyme is used to generate the first nucleic acid molecule but not the second nucleic acid molecule. In some embodiments, the step of linearising the at least one circular nucleic acid molecule in vivo using a rare-cutting sequence specific DNA cleaving enzyme is used to generate the second nucleic acid molecule but not the first nucleic acid molecule.

In a preferred embodiment of the third aspect, there is provided a method for improving the efficiency of homologous recombination between at least a first nucleic acid molecule and a second nucleic acid molecule which share at least one region of sequence homology, comprising, prior to performing homologous recombination in vivo, the step of linearising at least one circular nucleic acid molecule in vivo using a rare-cutting sequence-specific DNA cleaving enzyme to generate the first and/or the second nucleic acid molecule, wherein the efficiency of homologous recombination is improved relative to when homologous recombination is performed in vivo without the step of linearising at least one circular nucleic acid molecule in vivo using a rare-cutting sequence specific DNA cleaving enzyme. In some embodiments of the third aspect, the efficiency of homologous recombination is improved relative to when homologous recombination is performed in vivo using a linear first nucleic acid molecule and a circular second nucleic acid molecule. In some embodiments of the third aspect, the efficiency of homologous recombination is improved relative to when homologous recombination is performed in vivo using a circular first nucleic acid molecule and a linear second nucleic acid molecule. In some embodiments of the third aspect, the efficiency of homologous recombination is improved relative to when homologous recombination is performed in vivo using a linear first nucleic acid molecule and a linear second nucleic acid molecule, wherein the host cell has been transformed with at least the linear second nucleic acid molecule in linearised form. In some embodiments of the third aspect, the efficiency of homologous recombination is improved relative to when homologous recombination is performed in vivo using a linear first nucleic acid molecule and a linear second nucleic acid molecule, wherein the host cell has been transformed with at least the linear first nucleic acid molecule in linearised form.

The increase in the efficiency of homologous recombination that results from the use of the method of the third aspect of the invention is by virtue of a different mechanism than the increases in efficiency of homologous recombination that are produced by the methods of the first and second aspects of the invention. Accordingly, the method of third aspect of the invention may be employed (i) on its own, (ii) in combination with the first aspect of the invention or the second aspect of the invention, or (iii) in combination with both the first and second aspects of the invention.

This increase in the frequency of recombination that is provided by the method of the third aspect of the invention is particularly advantageous when employed in methods of cloning, such as library generation, for example in combination with the methods detailed above at page 17ff. In these methods, the first nucleic acid molecule is the nucleic acid to be cloned (for example, a genomic DNA fragment, or the double stranded cDNA recited in step iv) on page 19), and the second nucleic acid molecule is a linear cloning vector. The method of the third aspect of the invention can therefore be used to linearise the cloning vector in vivo (where the cloning vector has been designed to contain one or more recognition sites for a rare-cutting sequence specific DNA cleaving enzyme expressed by the host cell) from a circular form before homologous recombination occurs. In this instance, typically the host cell in which homologous recombination occurs will be transformed with the circular cloning vector, and then a culture of this transformed host cell will be grown up, and the rare-cutting sequence specific DNA cleaving enzyme induced so that it may act to linearise the circular vector. In some embodiments, the host cell may then be made competent and transformed with the nucleic acid to be cloned. Upon transformation, the linearised cloning vector can then undergo in vivo homologous recombination with the nucleic acid to be cloned. In some embodiments, the first nucleic acid is endogenous to the host cell, for example, genomic DNA or a fragment of genomic DNA, for example a fragment of a chromosome of the host cell, and so simple induction of expression of the rare-cutting sequence specific DNA cleaving enzyme together with shearing or digesting the genomic DNA (for example, with restriction enzymes) such that the sequence of interest remains intact, enables cloning to take place.

In the instance where the nucleic acid molecule being linearised is a cloning vector, generation of the linear nucleic acid molecule in vivo increases the likelihood that any given host cell in which homologous recombination may occur will contain linearised cloning vector, when compared to transforming linear vector into the host cell in order to effect LLHR. Accordingly, the increased probability that linear cloning vector is present increases the likelihood that homologous recombination will occur (and because recombination is more likely with linear rather than circular nucleic acid molecules) and which, in turn, increases the likelihood that a host cell will contain a cloned fragment. The increased frequency of recombination therefore leads to efficiencies in cloning libraries, and also in the cloning of specific individual DNA fragments, because lower quantities of reagents (host cells, nucleic acid to be cloned, cloning vector etc.) are required in order to obtain a successful result. This advantage is most apparent when the desired sequence to be cloned is only present at low frequency in the mixture of nucleic acids from which it is to be cloned, for example, when the first nucleic acid is genomic DNA or a fragment of genomic DNA. For example, in embodiments in which the first nucleic acid molecule is 50 kb in length, a 50 kbp fragment comprises a much lower percentage of the DNA in a eukaryotic genome compared to the percentage of the DNA in a prokaryotic genome—the ratio of a 50 kbp target fragment to other DNA sequences is at least 1:100 in prokaryotic genomes compared to 1:50000 in mammalian genomes. This embodiment of the invention is therefore particularly useful for cloning of fragments from eukaryotic genomes, which, as a result of their significantly greater size, have a much lower efficiency of cloning (per unit of reagent) than when cloning fragments from prokaryotic genomes.

A method of homologous recombination according to the third aspect of the invention takes place in a host cell. Similar considerations apply to the choice of host cell as for the method of the first aspect of the invention or the second aspect of the invention, but in the method of the third aspect of the invention the cell further comprises a rare-cutting sequence specific DNA cleaving enzyme. Thus the third aspect of the invention provides a host cell according to the first aspect of the invention or the second aspect of the invention, but wherein that cell further comprises a rare-cutting sequence specific DNA cleaving enzyme. An example of a host cell of the third aspect of the invention is an E. coli host cell comprising full-length RecE, RecT, red gamma and recA under control of the arabinose inducible Para-BAD promoter, wherein this construct has replaced the ybcC gene of the chromosome, and wherein the host cell further comprises a rare-cutting sequence specific DNA cleaving enzyme. For example, E. coli strain GB2005-dir further comprising a rare-cutting sequence specific DNA cleaving enzyme is an example of a host cell of the third aspect of the invention.

The rare-cutting sequence specific DNA cleaving enzyme should be chosen so that it does not recognize and cleave a sequence present in the chromosome of the host cell. Selection of an appropriate rare-cutting sequence specific DNA cleaving enzyme may be performed by the skilled person following the teachings herein. The use of a rare-cutting sequence specific DNA cleaving enzyme (i.e. an enzyme with a recognition sequence of more than 10 bp, for example more than 12 bp, more than 14 bp, more than 16 bp or more than 18 bp) is important because it ensures that when the DNA cleaving enzyme is expressed, it cleaves only a sequence in the plasmid, and does not cleave the host cell's chromosome(s) (which would be very detrimental to the host cell and may destroy the sequence that is being cloned by cleaving within it). Thus, preferably, the rare-cutting sequence specific DNA cleaving enzyme does not recognize sequences in the host cell's chromosome.

The rare-cutting sequence specific DNA cleaving enzyme used in the third aspect of the invention may be a homing endonuclease, a zinc finger nuclease (ZFN) or transcription activation-like effector nuclease (TALEN) or any other suitable rare-cutting sequence specific DNA cleaving enzyme. Preferably the homing endonuclease is selected from the group consisting of I-SceI, I-CeuI, I-CreI, I-ChuI, I-CsmI, I-DmoI, I-PanI, I-SceII, I-SceIII, I-SceIV, F-SceI, F-SceII, PI-AaeI, PI-ApeI, PlCeuI, PI-CirI, PI-CtrI, PI-DraI, PI-MavI, PI-MfII, PI-MgoI, Pl-MjaI, PI-MkaI, PI-MleI, PI-MtuI, PI-MtuHI, PI-PabIII, PI-PfuI, Pi-PhoI, PI-PkoI, PI-PspI, PI-RmaI, PI-SceI, PI-SspI, PI-TfuI, PI-TfuII, PI-TliI, PI-TliII. PI-TspI, PI-TspII, PI-BspI, PI-MchI, PI-MfaI, PI-MgaI, PI-MgaII, PI-MinI, PI-MmaI, Pi-MshI, PI-MsmII, PI-MthI, PI-TagI, PI-ThyII, I-NcrI, I-NcrII, I-PanII, I-TevI, I-PpoI, I-DirI, I-HmuI, I-HmuII, I-TevII, I-TevIII, F-SceI, F-SceII (HO), F-SuvI, F-TevI, and F-TevII.

In preferred embodiments, the method of the third aspect of the invention may be mediated by any suitable 5' to 3' exonuclease and annealing protein. In some embodiments of a method of the third aspect of the invention, the homologous recombination is mediated by RecE and a phage annealing protein. The phage annealing protein is preferably RecT. In some embodiments, RecE is a truncated RecE as used in existing methods of homologous recombination. For example, in some embodiments, the RecE used in the method of the third aspect of the invention comprises the 5' to 3' exonuclease activity of RecE but does not comprise any N-terminal sequence from amino acids 1-587 of SEQ ID NO:1. For example, in some embodiments, the RecE used in a method of the third aspect of the invention is selected from a RecE consisting of amino acids 588-866, 595-866, 597-866, 602-866 or 606-866 of SEQ ID NO:1.

In some embodiments, the method of homologous recombination performed in the third aspect of the invention is a method of homologous recombination as described in the first aspect of the invention or the second aspect of the invention. All embodiments described for the first or second aspects of the invention may be applied to the third aspect of the invention. Thus, in some embodiments, the RecE used in the method of the third aspect of the invention is a RecE as used in a method of the first aspect of the invention or the second aspect of the invention. The use of a RecE comprising or consisting of 564-866 of SEQ ID NO:1 is particularly preferred. In some embodiments, full length RecE is used.

In one embodiment of a method of the third aspect of the invention, the method comprises performing homologous recombination in the presence of full length RecE, RecT, Red gamma, RecA and at least one single stranded oligonucleotide that has no sequence homology to the nucleic acid molecules undergoing homologous recombination, following generation of linear nucleic acid molecules in vivo using a rare-cutting sequence specific DNA cleaving enzyme. In such embodiments, expression of RecE is preferably under the control of a rhamnose-inducible promoter. A host cell for carrying out such a method is also provided.

The rare-cutting sequence specific DNA cleaving enzyme is typically under the control of an inducible promoter (as discussed above for expressing the exonuclease and/or annealing protein). In some embodiments the promoter used to express the rare-cutting sequence specific DNA cleaving enzyme is the same promoter as used to express the exonuclease and/or annealing protein. For example, if RecE is expressed under the Para-BAD promoter, then the DNA cleaving enzyme is also expressed under the Para-BAD promoter. In some embodiments the promoter used to express the rare-cutting sequence specific DNA cleaving enzyme differs from the promoter used to express the exonuclease and/or annealing protein. For example, if RecE is expressed under the Para-BAD promoter, then the rare-cutting sequence specific DNA cleaving enzyme may be expressed under the Plac promoter, or if RecE is expressed under the rhamnose-inducible promoter, then the DNA rare-cutting sequence specific DNA cleaving enzyme may be expressed under the Para-BAD promoter.

The rare-cutting sequence specific DNA cleaving enzyme may be expressed from an episome introduced into the host cell in which the in vivo LLHR is to occur. If the rare-cutting sequence specific DNA cleaving enzyme is expressed from a vector, then the origin and any selection marker on the vector should be chosen such that they are compatible with any other vectors present in the cell, for example the cloning vector to be linearised, if one is present. The choice of appropriate origins and selection markers can be performed by the skilled person using their common general knowledge together with the teachings herein. For example, in some embodiments, the rare-cutting sequence specific DNA cleaving enzyme is expressed from an R6K origin based plasmid, which is compatible with BAC, p15A or pBR322 origin based plasmids. In an alternative, the rare-cutting sequence specific DNA cleaving enzyme may be expressed from the chromosome of the host cell.

In some embodiments, the linearised cloning vector is a multicopy plasmid, a BAC, a YAC, or the chromosome of the host.

A kit is provided for performing a method of homologous recombination according to the third aspect of the invention. A kit for performing a method of the third aspect of the invention comprises at least one nucleic acid encoding a rare-cutting sequence specific DNA cleaving enzyme as described above. Preferably, the kit also comprises one or more nucleic acid molecules encoding RecE, RecT and optionally Red gamma. In some embodiments, the kit also comprises one or more nucleic acid molecules encoding Redalpha and Redbeta. In some embodiments, the nucleic acid molecules are in the form of expression vectors suitable for transformation into a host cell. In other embodiments, the kit comprises a host cell that comprises these nucleic acid molecules. In some embodiments, the kit comprises a host cell that expresses RecE, RecT and optionally Red gamma and/or which expresses Redalpha and Redbeta, and a rare-cutting sequence specific DNA cleaving enzyme. In some embodiments, the kit is the CLONEEZ® PCR Cloning Kit or the Cold Fusion Cloning Kit which additionally comprises the at least one nucleic acid encoding a rare-cutting sequence specific DNA cleaving enzyme as described above. In some embodiments, a kit for performing a method of homologous recombination is a kit for use in a method of the first aspect of the present invention or the second aspect of the present invention, as described above, which additionally comprises the at least one nucleic acid encoding a rare-cutting sequence specific DNA cleaving enzyme.

Abbreviations
 LLHR—linear to linear homologous recombination
 LCHR—linear to circular homologous recombination
 gba in constructs=Red gamma,-Red beta,-Red alpha operon
 gbaA in constructs=Red gamma-Red beta-Red alpha operon plus recA from *E. coli* K12
 Red-gba=Red gamma, Red beta and Red alpha
 ETg in constructs=RecE-RecT operon plus Red gamma (full length RecE)
 ETgA in construct=RecE-RecT operon plus Red gamma plus RecA nt—nucleotide
bp—base pair
kbp—kilo base pairs
ng—nanogram Reference to RecE in the examples refers to full length RecE unless an amino acid residue number is provided in conjunction with the RecE.

BRIEF DESCRIPTION OF THE FIGURES

(FIG. 1A) Schematic illustration of a linear to circular homologous recombination (LCHR) assay. (FIG. 1B) Schematic illustration of the equivalent linear to linear homologous recombination (LLHR) assay. (FIG. 1C) A comparison of the efficiency of LCHR mediated by different proteins as indicated by the number of Cm plus Kan resistant colonies. (FIG. 1D) A comparison of the efficiency of LLHR mediated by different proteins as indicated by the number of Cm plus Kan resistant colonies.

(FIG. 2A) A comparison of LCHR efficiency in GB2005 upon expression of full length and truncated forms of RecETg. (FIG. 2B) The same as (FIG. 2A) except using the LLHR assay. (FIG. 2C) Detection of RecE expression by western blotting using a RecE antibody. (FIG. 2D) Detection of RecT by western blotting of the same protein extracts.

(FIG. 3A) The effect on LLHR efficiency of the induction of expression of a C-terminally truncated form of RecE comprising amino acid 1 to amino acid 601 expressed from pSC101-BAD with RecT and Red gamma using the LLHR assay of Example 1. (FIG. 3B) A comparison of LLHR with expression of pSC101-BAD E (1-601) Tg in HS996-BAD-E602T (right hand column) to expression of the Red gamma expression vector, pSC101-BAD-gam-tet (left hand column). (FIG. 3C) Efficiency of LLHR in E. coli strain GB2005 without RecT expression using the plasmid pSC101-BAD-Eg-tet to express full length RecE and Red-gamma but without RecT (Eg) compared to efficiency of LLHR with expression of Red gamma only from pSC101-BAD-gam-tet (gam).

(FIG. 4A) LCHR mediated by Red-gba expressed from pSC101-BAD-gba-tet. (FIG. 4B) LLHR mediated by RecETg expressed from pSC101-BAD-ETg-tet. The length of the homology arms used vary as indicated on the x-axis.

(FIG. 5A) The recombination efficiency of LLHR in GB2005 mediated by full length RecE plus RecT alone (ET), with Red gamma (ETg) or with RecA (ETgA), expressed from pSC101-BAD-ET-tet, pSC101-BAD-ETg-tet, and pSC101-BAD-ETgA-tet respectively. (FIG. 5B) The recombination efficiency of LLHR in E. coli strain GB2005-dir, in which an araC-Para-BAD-ETgA operon has been integrated into the genome, in comparison to the E. coli strain YZ2005, which has the recET operon in the genome expressed under a constitutive promoter. The efficiency is indicated by the ratio of recombinants (colonies on Cm and Kan selection plates) to the survivals (colonies on LB plates without any antibiotics). (FIG. 5C) The transformation efficiency of E. coli stains GB2005-dir and YZ2005 as measured by the ratio of transformants (colony number of Amp selection plates) to the survivals (colony number of LB plates without any antibiotics).

(FIG. 6A) The effect of the addition of single stranded DNA oligonucleotides on background LLHR (FIG. 6B) The same experiment as in (A) except exogenous proteins were expressed as indicated from pSC101 BAD by arabinose induction (gba-Red gamma, beta, alpha; ETg-full length RecE, RecT and Red gamma; E564Tg—the C-terminus of RecE starting at amino acid 564, RecT and Red gamma; E602Tg—the C-terminus of RecE starting at amino acid 602, RecT and Red gamma.

(FIG. 6C) The efficiency of LCHR mediated by expression of Red-gba from the arabinose inducible BAD promoter (Para-BAD); the rhamnose inducible Prha promoter (rhaS-Prha) and the tetracycline inducible tetO promoter (tetR-tetO). (FIG. 6D) The efficiency of LCHR mediated by expression of RecET from the same promoters and additionally the temperature inducible pL promoter (cI578-pL). All promoters were cloned into the pSC101 plasmid.

(FIG. 7B) Schematic illustration of a LCHR assay using a ssDNA oligonucleotide and a BAC (FIG. 7C) Expression of various combinations of proteins evaluated with the LLHR assay. The ssDNA oligonucleotide was either one strand (leading) or its complement (lagging) or an annealed double-stranded DNA from two complementary oligos (control). Recombination was evaluated by scoring the number of chloramphenicol resistant colonies. (FIG. 7D) As for the experiment in (FIG. 7C) except using the LCHR assay of (B).

(FIG. 8A) The efficiency of LLHR in three E. coli strains with or without induction of Red gamma (FIG. 8B) Schematic of the cassette hyg-araC-Para-BAD in front of the recE gene in HS996 (FIG. 8C) The efficiency of LLHR in HS996-BAD-ET before or after arabinose induction of endogenous RecET expression and with or without expression of Red-gamma.

(FIG. 9A) Schematic of an example of triple recombination. (FIG. 9B) The efficiency of triple recombination mediated by Red and RecET using linear products with symmetric dephosphorylated ends (OO) or assymetrical phosphothioated ends (OS+SO).

(FIG. 10A) Exemplary schematic of quadruple recombination in which a linear DNA molecule is integrated into a target vector by two oligonucleotides. (FIG. 10B) The efficiency of quadruple recombination mediated by Red or RecET measured by kanamycin resistance colonies after electroporation of the linear DNA and oligonucleotides into GB2005 harbouring the target vector.

(FIG. 11A) Schematic illustration of a multiple linear DNA recombination to generate a circular plasmid. Each PCR product has an overlapping region of sequence identity with its neighbour as indicated by the dotted arrows. (FIG. 11B) Detailed map of pUBC-neo plasmid that was generated from 4 PCR products, which are illustrated inside the plasmid.

(FIG. 12A) Schematic of the synthesis of cDNA. i) A 3' oligonucleotide composed of a homology arm (HA; grey line) at its 5' end and a stretch of Ts at its 3' end will anneal to mRNA polyA tails and prime first strand cDNA synthesis with MMLV-based RT reverse transcriptase. ii) At the mRNA 5' end, the RT continues to add non-templated nucleotides, primarily deoxycytidines (dC), to the 3' end of the newly synthesized first strand cDNA. iii) A second oligonucleotide (known as a 'PlugOligo'), composed of a homology arm (grey line) at its 5' end and a stretch of Gs at its 3' end plus a 3' phosphate anneals to the C track and primes second strand synthesis. The final double-stranded cDNA has homology arms (HAs) for recombination with the cloning vector. (FIG. 12B) Schematic of the cloning of cDNA with linear plus linear recombineering. i) Diagram of the cDNA cloning vector. ii) The cloning vector is linearized at the restriction sites R to expose the HAs. iii) The double-stranded cDNA and the linearized cloning vector are transformed into RecETgA expressing GB2005-dir for linear to linear recombination. iv) The final cDNA library.

(FIG. 13A) Schematic of a LLHR method for subcloning from a BAC. (FIG. 13B) Table summarising the successful subcloning of four genes.

(FIG. 14A) Two plasmids for reducing the frequency of intramolecular recombination. (FIG. 14B) Schematic of a double recombination 'fishing' strategy for enhancing the identification of correct products.

(FIG. 16A) Schematic illustration of a recombination assay to check if DNA replication is required to initiate LCHR. (FIG. 16B) In the strain GB2005-pir, LCHR is efficiently mediated by Red gamma, beta, alpha (gba), and less efficiently mediated by RecETg. In the strain GB2005 (pir–), no recombination occurs. (FIG. 16C) Schematic illustration of the equivalent LLHR assay to that shown in (FIG. 16A) created by linearizing the R6K plasmid in the pir gene. (FIG. 16D) LLHR occurred in GB2005 and GB2005-pir, regardless of whether pre-existing Pir protein was present or not.

FIG. 17C) and LCHR (FIG. 17B; FIG. 17D) assays with RecETg or Red gba expressed from pSC101-BAD. The PCR products have symmetric or asymmetric ends. A 5' hydroxyl is indicated by (O); 5' phosphate (P); two consecutive 5' phosphothioate bonds at the 5' end with a 5' hydroxyl(S); two consecutive 5' phosphothioate bonds at the 5' end with a 5' phosphate (pS); two consecutive 5' phosphothioate bonds 50 nucleotides from the 5' end (iS). For linear plus linear recombination, the status of both linear DNAs is given, whereas for linear plus circular, only the status of the single linear DNA is given.

(FIG. 19A) Cloning vector comprising I-SceI cleavage sites. Plasmid map of p15A-amp SceI site-km. The plasmid contains a kanamycin resistance marker flanked by two I-SceI recognition sites. (FIG. 19B) Image of an agarose gel showing the plasmid DNA prepared from cells in which the I-SceI expression plasmid and the recipient plasmid co-exist, with and without arabinose induction. Lane 1-2 are DNA prepared from un-induced cells and lane 3-4 are DNA from 1 hour induced cells. The plasmid DNA was loaded directly on the agarose gel without further digestion.

EXAMPLES

Example 1—RecET is More Efficient at Mediating LLHR than Red Beta and Red Alpha

Figure 1A:
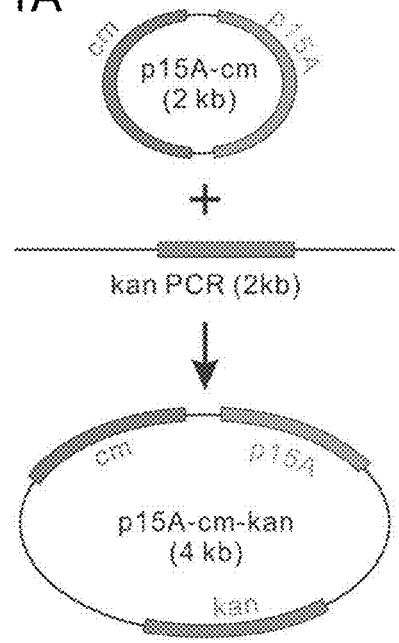
FIGS. 1A-1D. Distinct in vivo bioactivity of Red and RecET.
Figure 1B:
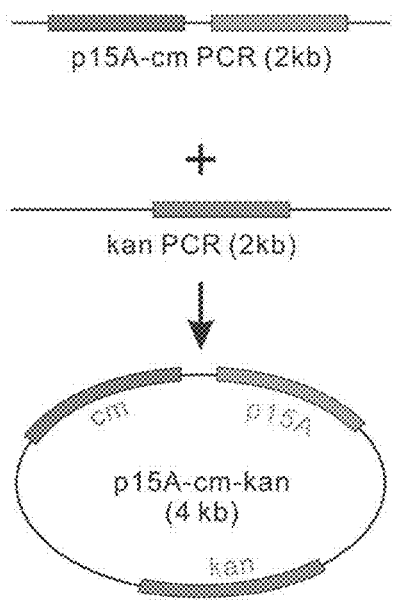

The ability of different proteins to mediate LCHR and LLHR was assayed. LCHR and LLHR were performed as described schematically in FIG. 1A and FIG. 1B respectively. For LCHR, the kan PCR product (kanamycin resistance gene amplified by PCR) has 50 bp homology arms at either end to the p15A-cm plasmid which carries chloramphenicol (Cm) resistance. Co-electoporation of the plasmid and the PCR product into recombineering proficient *E. coli* cells (here GB2005) and successful LCHR results in the formation of the chloramphenicol (Cm) plus kanamycin (Kan) resistant plasmid p15A-cm-kan. Similarly, in the LLHR assay, the kan PCR product has two 50 bp homology arms to the linear p15A-cm PCR product. Again, co-electoporation of the two PCR products into recombineering proficient *E. coli* cells and successful LLHR results in the Cm plus Kan resistant plasmid p15A-cm-kan.

To study the function of the RecET and Red systems in LCHR and LLHR, the recombinase genes were cloned into a temperature sensitive origin based plasmid under an arabinose inducible promoter to generate a series of expression vectors. The GB2005 strain, which is a derivative of HS996 (16, 17) with the RecET operon deleted in its chromosome (25), was used to perform the recombination assay. Most *E. coli* strains used in research including GB2005 are RecBCD intact. To prevent the degradation of linear DNA molecules by RecBCD, Red-gamma protein was temporarily expressed in GB2005 to inactivate RecBCD in *E. coli* (26). Two hundred nanograms of each DNA molecule were transformed by electroporation.

Figure 1C:
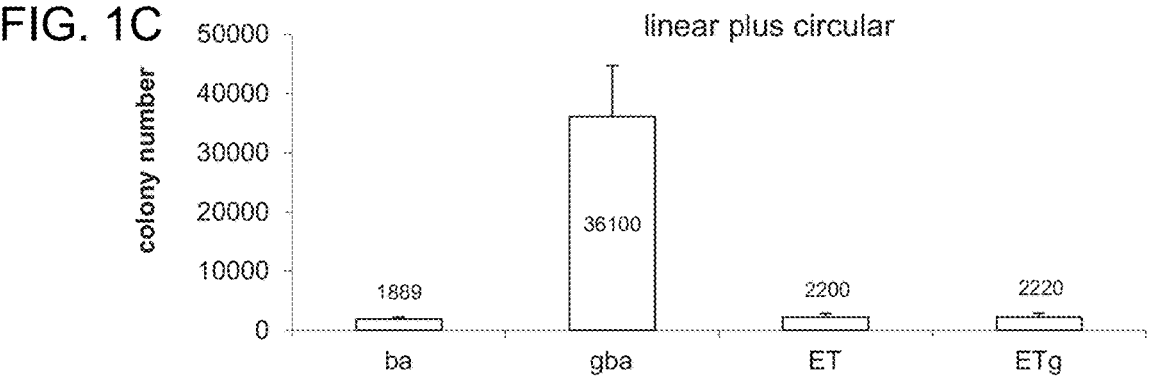
Figure 1D:
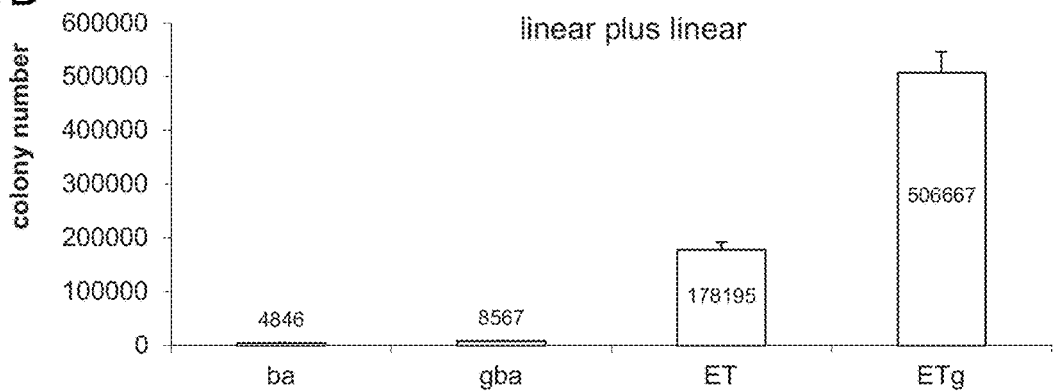

The proteins were expressed from pSC101 BAD by arabinose induction of operons containing; ba—Red beta, Red alpha; gba—Red gamma, Red beta, Red alpha; ET—full length RecE, RecT; ETg—full length RecE, RecT, Red gamma. Successful recombination and transformation was measured by the number of Cm and kan resistant colonies. As shown in FIG. 1C, LCHR is mediated most efficiently by the lambda Red system and expression of Red alpha, beta and gamma. In contrast, as shown in FIG. 1D, the RecET system is far better than the lambda Red system in mediating LLHR, producing approximately 60 times more colonies.

It is also important to note that the number of colonies produced by LLHR with RecET is an order of magnitude higher than that produced by LCHR with Red beta and Red alpha. In both systems, additional expression of Red gamma improved efficiency.

Example 2—Full Length RecE with RecT is Required for Efficient LLHR

It is known that only the C-terminal region of RecE is required for LCHR and that truncated RecE increases LCHR efficiency (13, 14). Here the ability of truncated RecE and full length RecE to mediate LLHR was assayed. The LCHR (FIG. 2A) and LLHR (FIG. 2B) assays were the same as described in Example 1.

Figure 2A:
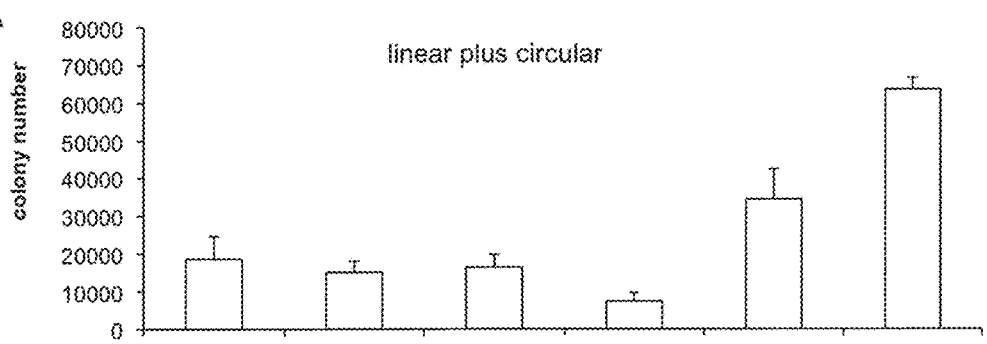
FIGS. 2A-2D. Truncated RecE efficiencies in LCHR and LLHR.
Figure 2B:
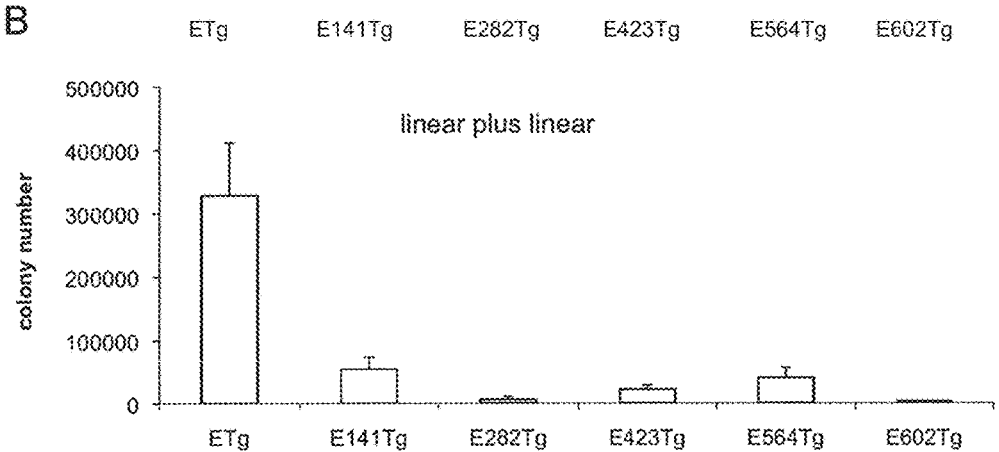

All proteins were expressed from pSC101 BAD plasmid after arabinose induction. RecT, Red gamma and different RecE constructs were expressed. The assay of Example 1 was used and kanamycin resistant colonies were counted. The numbers in the RecE constructs indicate the residue at which the truncated RecE starts (E=full length RecE, E141=truncated RecE starting at residue 141 and containing an N-terminal methionine, etc.). Full length RecE is better at mediating LLHR than any of the truncated constructs (FIG. 2B). This is in stark contrast to LCHR, for which full length RecE is the least efficient and the efficiency of the truncated RecE constructs increases with increasing truncation (FIG. 2A).

Figure 2C:
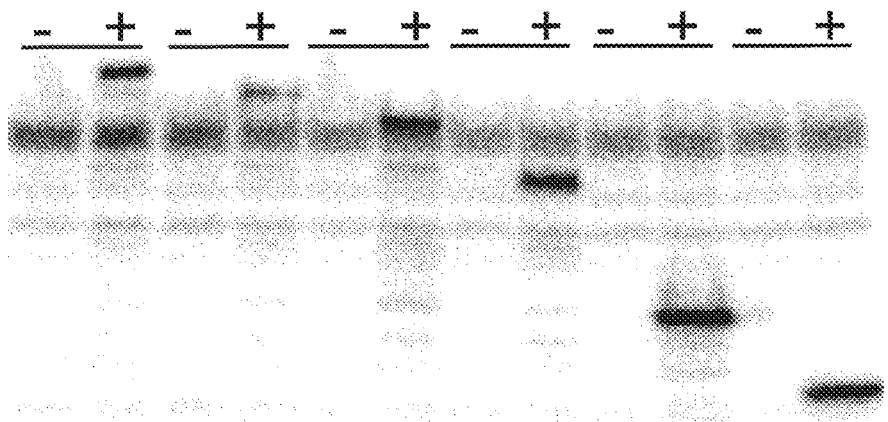
Figure 2D:
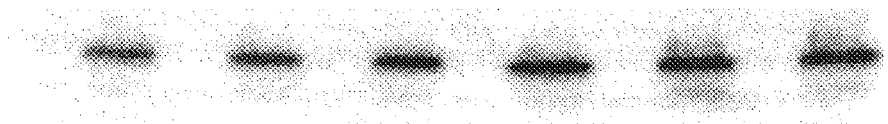

FIGS. 2C and 2D display the detection of RecE and RecT with western blots using rabbit anti-RecE602 (FIG. 2C) and anti-recT anti-sera (FIG. 2D). The uninduced (−) and arabinose induced (+) protein extracts were electrophoresed on an SDS PAGE. All RecE versions include the final 264 amino acids. The molecular weight of full length RecE, RecE141 (i.e. the first 140 amino acids were deleted and replaced with an N-terminal methionine), RecE282, RecE423, RecE564 and RecE602 are 96.4, 80.8, 65.6, 50.1, 34.6 and 30.4 kDa respectively. The molecular weight of RecT is 29.7 kDa. It can be seen that RecE and RecT were only expressed after L-arabinose induction. These data confirm that the L-arabinose inducible BAD promoter is tightly regulated. Furthermore, these data demonstrate that the improvement in LLHR efficiency achieved with full length RecE is not caused by variations in expression and neither does the truncated RecE cause instability of the protein or of RecT.

Figure 3A:
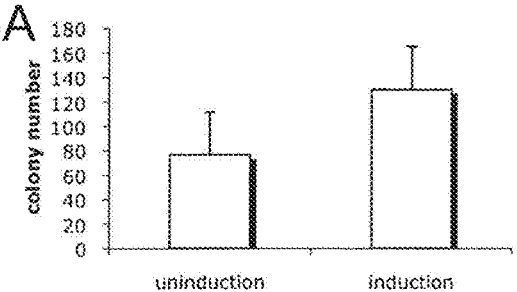
FIGS. 3A-3C. Full length RecE must be expressed in one piece for enhanced LLHR.
Figure 3B:
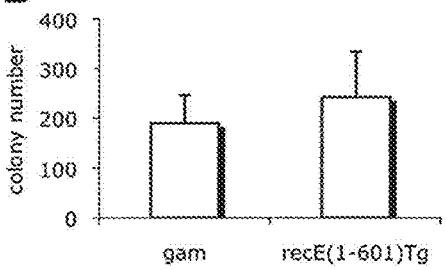

Having identified that full length RecE is more efficient at LLHR than C-terminal fragments, it was investigated whether N-terminal RecE fragments have any activity or whether N-terminal and C-terminal fragments have any activity when expressed together. Using the LLHR assay of Example 1 in GB2005, a C-terminally truncated form of RecE comprising amino acid 1 to amino acid 601 was expressed from pSC101-BAD along with RecT and Red gamma. Very little recombination was observed and there was no significant difference between induction and non-induction of the proteins (FIG. 3A). The recombinants are a result of background recombination. Therefore, N-terminal RecE (from aa1-aa601) alone has no LLHR activity. To investigate whether N-terminal and C-terminal fragments of RecE can compliment each other, a BAD promoter was inserted in front of recE602 of the recET operon in the chromosome of HS996 to activate expression of the C-terminus of RecE from amino acid 602 and RecT from the chromosome (24). This strain is HS996-recE602T. The same expression plasmid as for FIG. 3A, PSC101-BAD E (1-601) Tg, was used in the HS996-BAD-E602T strain. LLHR was compared to the level achieved using the Red gamma expression vector, pSC101-BAD-gam-tet. No significant effect conveyed by RecE 1-601 was observed. After induction this strain expresses RecT and C-terminal RecE. On top of this, Red Gam (FIG. 3B left column) or RecE (aa1-601) Tg (FIG. 3B right column) were expressed from the pSC101 plasmid. These data show that complimentary expression of N-terminal RecE and C-terminal RecE cannot mediate LLHR (FIG. 3B). RecE must be expressed as one polypeptide.

Figure 3C:
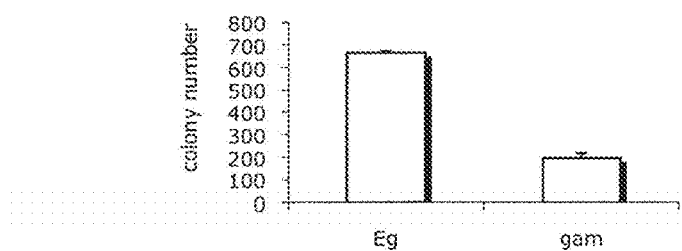

Finally, FIG. 3C compares LLHR in *E. coli* strain GB2005 mediated by full length RecE and Red gamma expression (left hand bar, pSC101-BAD-Eg-tet) to LLHR mediated by Red gamma expression alone (right-hand bar, pSC101-BAD-gam-tet), both in the absence of RecT. These data demonstrate that some LLHR occurs, presumably because some endogenous RecT-like activity is present. However, without RecT expression, full length RecE is not able to mediate highly efficient LLHR.

Example 3—Effect of Homology Length on LLHR Efficiency

Figure 4A:
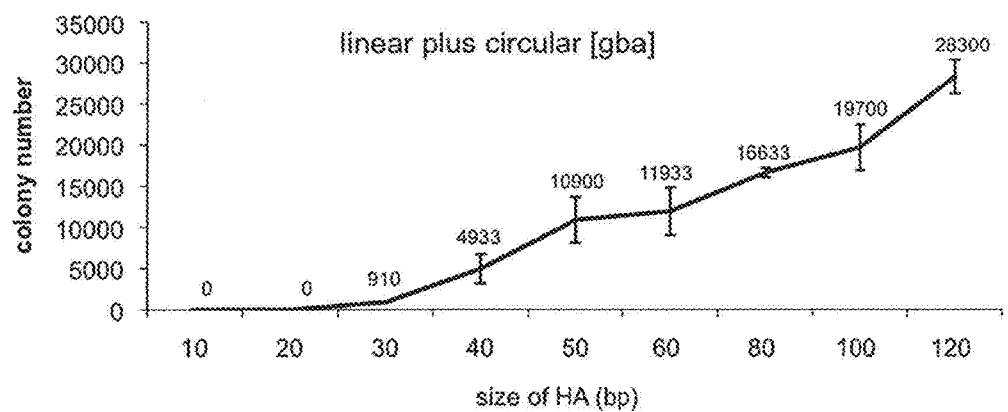
FIGS. 4A and 4B. Minimum size of homology sequence required for recombineering.
Figure 4B:
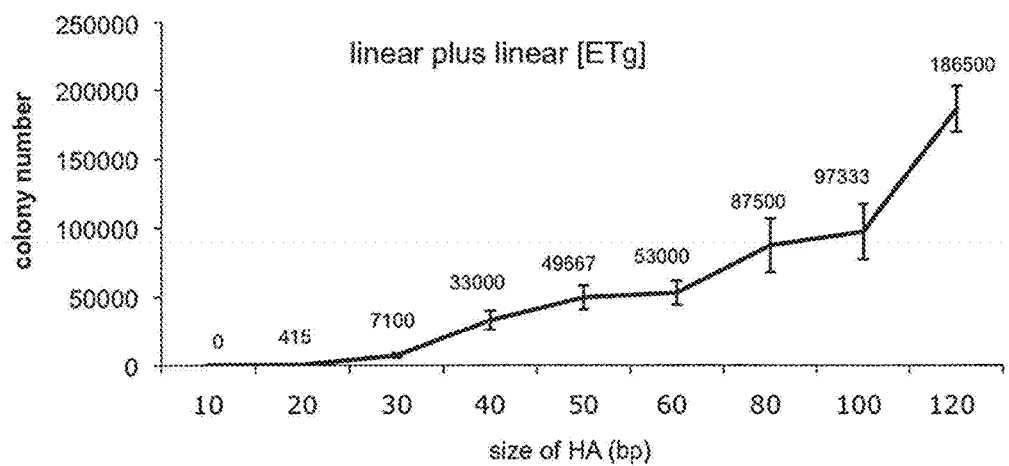

To investigate the effect of the length of homology arms on LCHR and LLHR efficiency, the assays as described in Example 1 were performed with a series of linear molecules with different length homology arms at both ends. The increasing length of homology arms increases the efficiency of both Red recombinase mediated LCHR (Red-gba expressed from pSC101-BAD-gba-tet, FIG. 4A) and RecET mediated LLHR (RecETg expressed from pSC101-BAD-ETg-tet, FIG. 4B). There is a difference between LLHR and LCHR concerning the minimum length of homology arms. RecET mediated LLHR needs only 20 bp homology between the two molecules. Lambda Red mediated LCHR needs at least 30 bp homology to combine the two molecules. However, these minimum requirements are similar and both LCHR and LLHR exhibit a linear relationship between efficiency and length of homology arms.

Figure 5A:
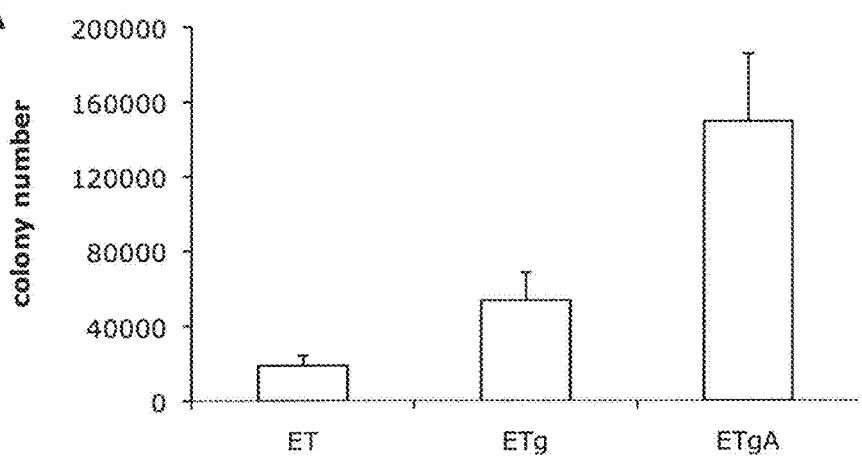
FIGS. 5A-5C. LLHR success is increased by co-expression of RecA because the transformation efficiency is increased.

Example 4—Improvement of LLHR by Transient Expression of RecA in a recA Deficient *E. coli* Strain It has previously been reported that JC8679 (recBC sbcA) (see references 5 and 13) is more efficient at performing LLHR than JC9604 (recA recBC sbcA) (see references 5 and 13) and that transient expression of RecA in recA deficient hosts does not contribute to Red/ET recombineering or to LCHR (13, 15, 22) but that it improves LCHR by increasing the transformation efficiency (27). To test the effect of transient expression of RecA on LLHR, the efficiency of LLHR with expression of RecE and RecT (ET) was compared to the efficiency of LLHR with expression of RecE, RecT and Red gamma (ETg) and to the efficiency of LLHR with expression of RecE, RecT, Red gamma and RecA (ETgA) (FIG. 5A), using the LLHR assay of Example 1. The proteins were expressed from pSC101-BAD-ET-tet, pSC101-BAD-ETg-tet, and pSC101-BAD-ETgA-tet respectively. RecA expression improves LLHR efficiency and resulted in a 3 fold increase in colony numbers.

Figure 5B:
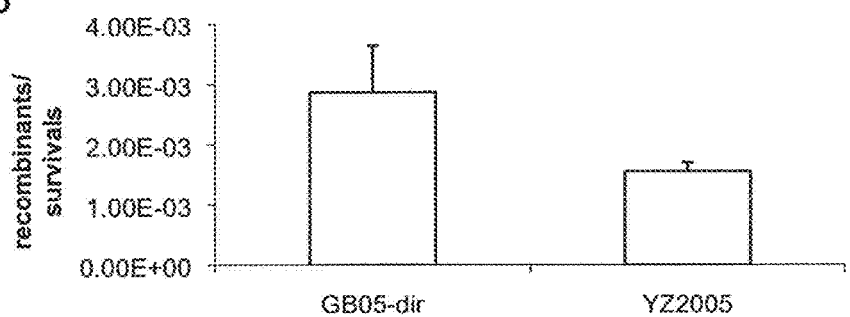
Figure 5C:
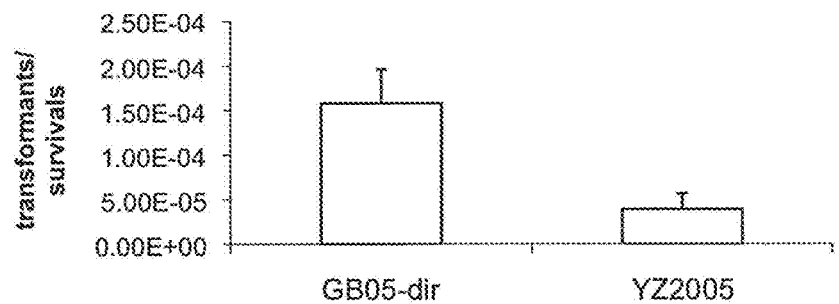

YZ2005 constitutively expresses RecA, RecE and RecT. We have observed that over-expression of RecET reduces transformation efficiency and causes slow growth and death of *E. coli* cells. Additionally, constitutively expressed recombinase leads to rearrangement of DNA molecules with repetitive sequences. To generate a suitable host for LLHR, ETgA under BAD promoter was integrated into GB2005 chromosome to replace ybcC, which encodes a putative exonuclease similar to Red alpha. The new host GB2005-dir is LLHR proficient after arabinose induced expression of ETgA. When LLHR was tested, GB2005-dir showed better LLHR efficiency than YZ2005 (FIG. 5B). Since the growth rate and the survival rate after electroshock differ between GB2005-dir and YZ2005, the LLHR efficiency in FIG. 5B was determined by the ratio of recombinants to surviving cells after electroporation and 1 hour recovery. Transformation efficiency from both hosts was tested by transforming 5 ng of pUC19 plasmid. As in FIG. 5B, the transformation efficiency was determined by the ratio of transformants to surviving cells. These data indicate that GB2005-dir after induction has a better transformation efficiency than YZ2005 (FIG. 5C). This experiment demonstrates that RecA improves the transformation efficiency rather than the recombination efficiency.

Example 5—Non-Homologous Single-Stranded DNA (ssDNA) Oligonucleotides Enhance LLHR It was surprisingly determined that non-homologous single-stranded DNA oligonulceotides improve the efficiency of LLHR. This was demonstrated both without expression of additional recombinases, relying on inefficient background levels of recombination in GB2005 (FIG. 6A), and also with expression of the Red and RecET systems (FIG. 6B).

Figure 6A:
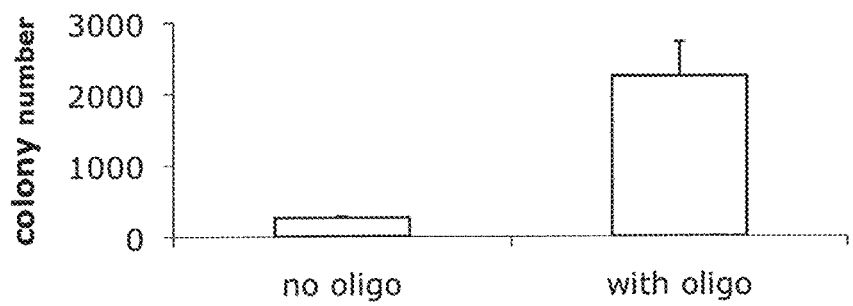
FIGS. 6A and 6B. LLHR is enhanced by adding nonhomologous ssDNA.
Figure 6B:
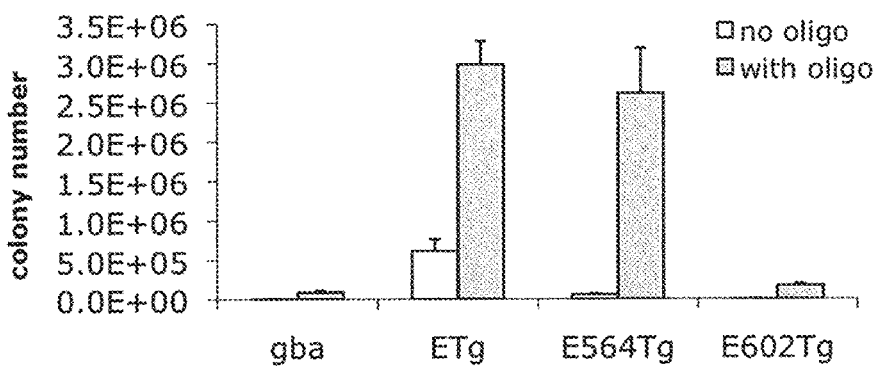

LLHR occurs in a wild-type E. coli K12 strain with low efficiency (1-3), as shown in FIG. 3A, left column and FIG. 6A, left column. The LLHR assay illustrated in Example 1 was used to evaluate the effect of adding single stranded DNA oligonucleotides (100 pmol of a 40 nt oligo that has no sequence homology to either linear DNA substrates; with oligo). This was compared to not adding any ssDNA oligonucleotides (no oligo). No additional recombinases were expressed and the very inefficient levels of recombination observed here were mediated by unknown endogenous mechanisms in GB2005 (FIG. 6A). Co-transformation of the non-homologous DNA oligo together with two linear molecules increases the LLHR efficiency by 10 fold in GB2005 without RecET or Red expression (FIG. 6A). The 40 nt ssDNA (40 mer oligo) used had no homology to the two linear molecules for LLHR or to the chromosome DNA of the host.

Non-homologous ssDNA also improves LLHR in the presence of recombinases. The Red system (Red alpha, Red beta and Red gamma, gba) and the RecET system (RecE (either full length, E; or truncated, E564, E602) RecT and Red gamma, ETg) were expressed in GB2005. Co-electroporation of the non-homologous oligo together with two linear molecules for LLHR increased the efficiency by at least 45 times for E564Tg and about 5 times for ETg (FIG. 6B). LLHR is very inefficient when the Red system or RecE E602 is used, however, an improvement was seen when non-homologous ssDNA was used (FIG. 6B). It was determined that the best results are achieved with non-homologous oligonucleotides 40 nucleotides in length and used at 100 pmol per electroporation.

Example 6—Comparison of Inducible Promoters Used for Recombinase Expression

Four inducible promoters (Para-BAD promoter—arabinose inducible, rhaS-Prha promoter—rhamnose inducible, tetR-tetO promoter—tetracycline inducible and cI578-pL promoter—temperature inducible) are often used in E. coli. These different inducible promoters were used to drive expression of the Red and RecET systems to evaluate the efficiency of recombination driven by the promoters. All promoters were cloned onto the pSC101 plasmid. The models used for LCHR and LLHR were the same as described in Example 1.

Figure 6C:
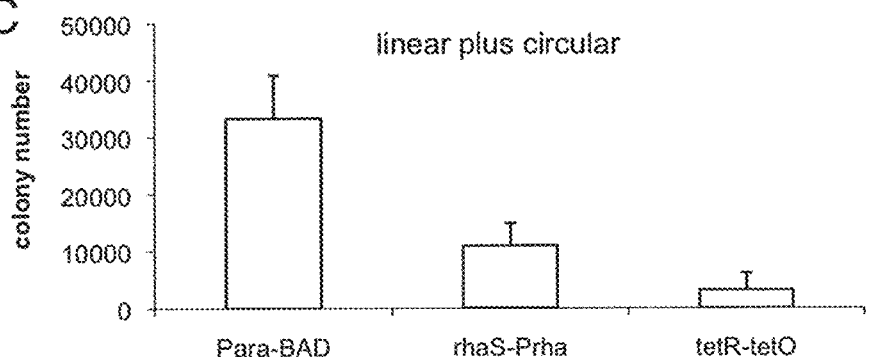
FIGS. 6C and 6D. Evaluation of LCHR and LLHR using different inducible promoters to express the phage proteins.
Figure 6D:
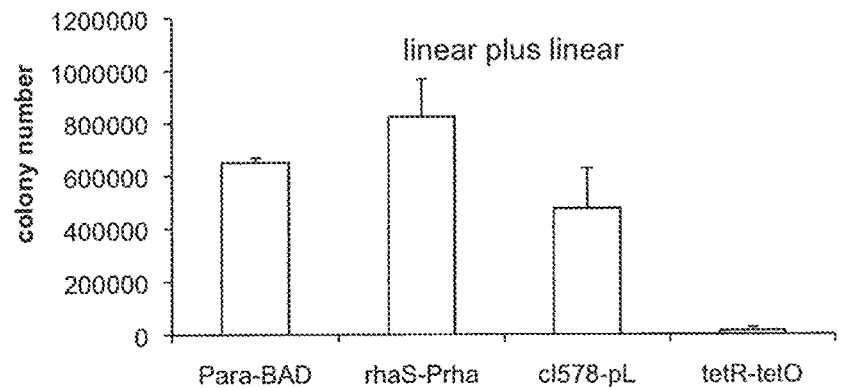

As shown in FIG. 6C, the BAD promoter driving gba was best suited to LCHR (FIG. 6C). For LLHR, the arabinose and rhamnose inducible promoters were best suited (FIG. 6D). The tetR-tetO tetracycline inducible promoter was the least effective for both LCHR and LLHR (FIGS. 6C and 6D). This may be because the tetR-tetO promoter is a weaker promoter in E. coli or because the inducer tetracycline is toxic to E. coli cells.

Example 7-Oligo (or ssDNA) to Linear Homologous Recombination (OLHR)

Figure 7A:
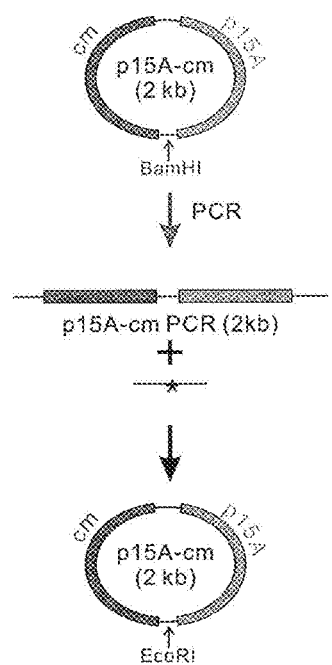
FIGS. 7A-7D. Evaluating LLHR when one substrate is a ssDNA oligonucleotide (FIG. 7A) Schematic illustration of the LLHR oligonucleotide assay.
Figure 7B:
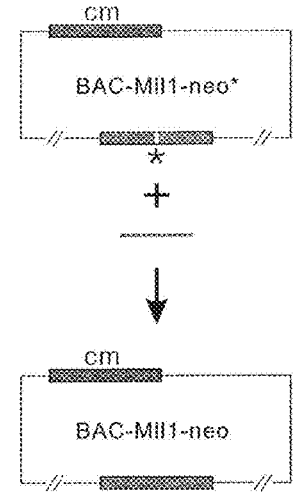

Red/ET recombineering technology has 3 main applications: a) insertion or integration of a DNA sequence into a circular target (13, 15); b) subcloning of a DNA sequence from a circular target or cloning of a DNA sequence from a linear target (7); and c) oligo repairing (22, 23). The data of FIGS. 1-6 show there are significant differences between the performance of the RecET system and the Red system in LLHR and LCHR. The difference may also apply in oligo repairing. Oligo repairing can be separated into two actions: recombination of an oligo into a linearised vector to recircularise the vector (OLHR, FIG. 7A) and recombination of an oligo to integrate into a circular vector (FIG. 7B). Synthetic oligos can be either upper strand or lower strand according to the parental double-stranded DNA. Here we distinguish the oligos as leading strand or lagging strand according to the replication orientation in the target molecule. Annealed double-stranded DNA from two complementary oligos was also used as control in the experiment in FIG. 7C.

Figure 7C:
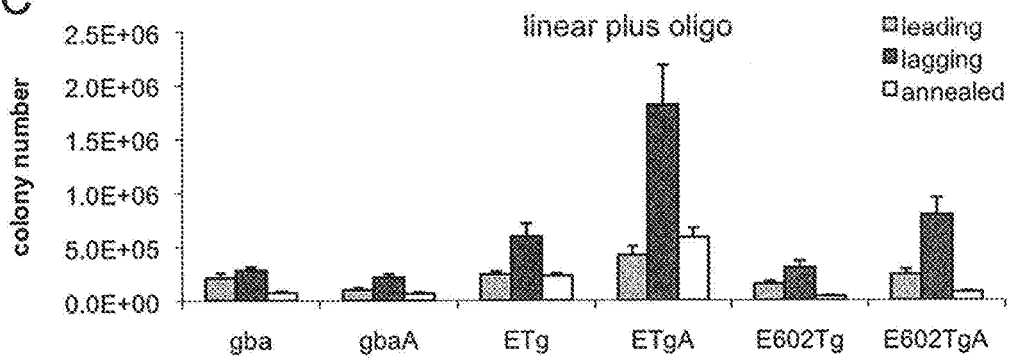

In the first experiment (FIGS. 7A and C, linear plus oligo), the plasmid was linearised with the use of BamH1 and an oligo with homology arms to the linearised plasmid was used to recircularise it and introduce an EcoR1 site. The p15A-cm plasmid was linearised by BamH I and co-electroporated into GB2005 with the ssDNA oligonucleotide. The oligo was 106 nt long and included two 50 nt regions of sequence identity (homology arms) to either side of the BamH1 site in p15A-cm plus an EcoR I site (6 nt) in the very centre. After recombination, the new p15A-cm plasmid had an EcoR I site in place of the BamH I site. As shown in FIG. 7C, the RecET system was most efficient at mediating this recombination. Transient expression of RecA also improved efficiency.

Figure 7D:
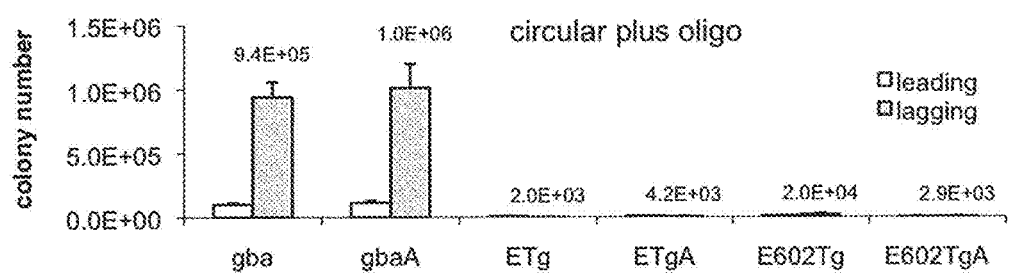

In the second experiment (FIGS. 7B and D, circular plus oligo), a BAC was used which was a circular episome BAC-MII1-neo* which included a mutated kanamycin resistance gene (neo*) caused by a frame shift. The 100 nt long oligo can correct the mutation and so restore kanamycin resistance. Successful incorporation of the oligo resulted in kanamycin resistance. As shown in FIG. 7D, the Red system was most efficient at mediating this recombination. Transient expression of RecA also improved efficiency. With both systems, use of a lagging strand oligo improved efficiency over the use of a leading strand oligo (FIGS. 7C and D). These results consolidate the conclusions drawn from the experiments of Examples 1, 2 and 5, and extend them to include the case when one linear substrate is ssDNA rather than dsDNA.

Example 8—the RecET Operon Exists in all *E. coli* K12 Strains but is Only Expressed in Strains with sbcA Background The *E. coli* K12 genome contains an integrated, incapacitated partial copy of the rac prophage with the RecET operon (28, 29). RecT is expressed from this operon but *E. coli* K12 does not express RecE. This experiment confirmed that *E. coli* K12 does not express RecE and demonstrated that it is possible to activate the RecE integrated in the *E. coli* genome to mediate LLHR.

Three strains derived from *E. coli* K12 were used; GB2005, HS996 and DH10B. GB2005 was created by deleting the recET operon from the genome of HS996. This removal of the RecET operon had no effect on residual LLHR and there was no difference between GB2005 and HS996 (uninduction data points). Because LLHR may have been blocked by RecBCD, we also evaluated LLHR in the presence of the RecBCD inhibitor, Red gamma by introducing pSC101-BAD-gam-tet and inducing Red gamma expression with arabinose (induction). Again, there was very little difference between the RecET deleted strain, GB2005, and its parent, HS996. This confirms that the RecE integrated into the *E. coli* genome is not active and that any background LLHR observed is not mediated by the RecET pathway.

Figure 8A:
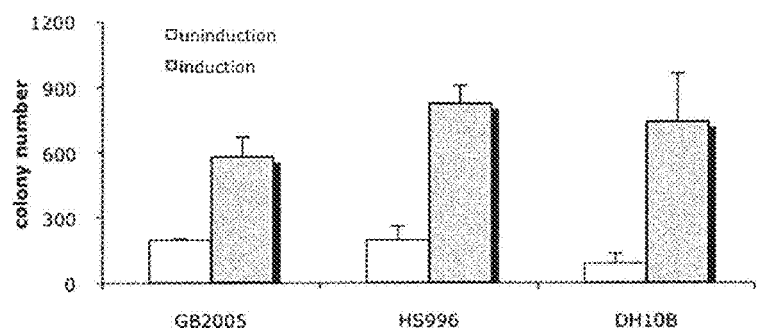
FIGS. 8A-8C. The RecET operon integrated into the E. coli K12 genome can be activated by insertion of the BAD promoter to express full length RecE.
Figure 8B:
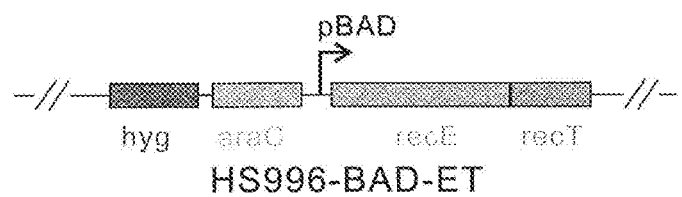
Figure 8C:
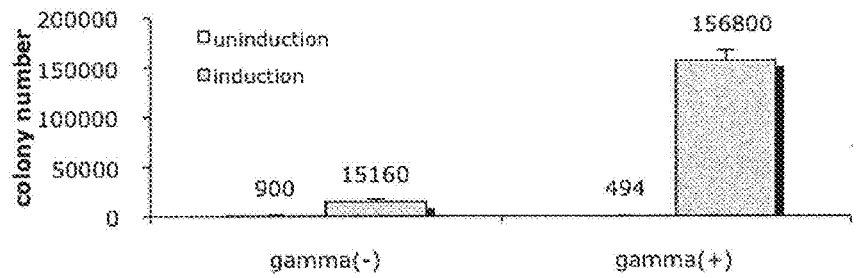

To activate the RecET operon in HS996, the BAD arabinose-inducible promoter was inserted as part of a cassette (hyg-araC-Para-BAD, FIG. 8B) in front of the recE gene in HS996 to create HS996-BAD-ET. LLHR, as measured using the assay of Example 1, was increased upon arabinose induction, indicating that the integrated RecE was mediating RecET LLHR (FIG. 8C, left bars). Expression of Red gamma further improved efficiency (FIG. 8D, right columns).

Example 9—Triple Recombination-Two Linear Molecules into a Circular Vector

Figure 9A:
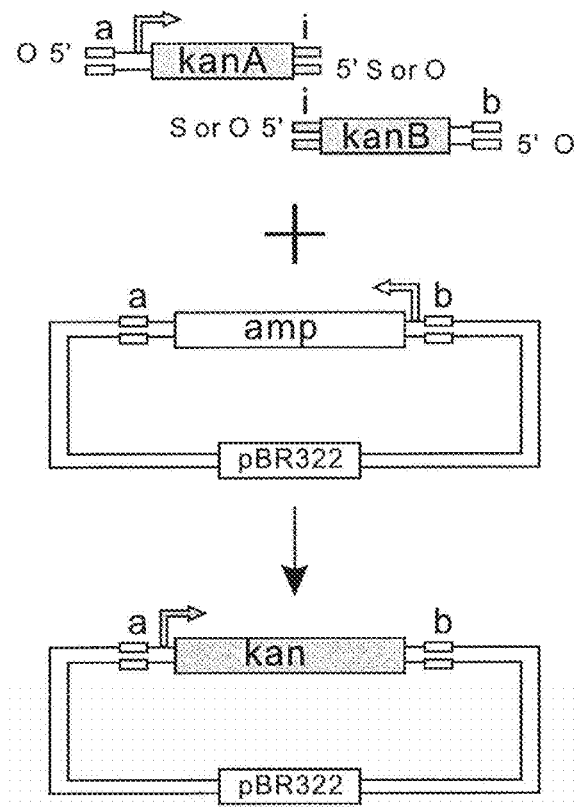
FIGS. 9A and 9B. Triple recombination mediated by Red or RecET.

Red/ET recombineering technology has been widely used to engineer a range of DNA molecules. The main application is to insert or integrate a cassette with a selection marker (sm) gene into the target molecule. In many situations, cassettes do not already have a selectable marker. The most common way to generate a cassette with an sm is to combine non-sm and sm constructs together to form one large molecule using Red/ET recombineering or by using over-lapping PCR to generate the large molecule of non-sm plus sm. To simplify this procedure, a strategy called triple recombination is provided herein (FIG. 9A). Triple recombination utilizes the Red/ET system and the effectiveness of full length RecE to combine three molecules, for example one circular target plus two linear molecules (non-sm and sm), together in vivo using short homology sequences present in the 3 molecules. In the present Example, as described in FIG. 9A, two linear DNA molecules have 50 bp over-lapping regions and each of them carries a homology arm to the target vector. Normally one of the linear molecules is a selection marker gene. After recombineering, the two linear molecules will be integrated into the target vector In this experiment to compare the ability of the Red operon (Red gamma, beta, alpha; gba) and full length RecET to mediate triple recombination, the kanamycin resistance gene was amplified by PCR into two pieces, which overlap in the middle by 50 bps of sequence identity. On the other end of each PCR product 50 bp homology arms to a plasmid were introduced. These two PCR products were electroporated into GB2005 already harbouring the target plasmid, Para-BAD24, and a pSC101-BAD plasmid from which either Red gba or RecET were expressed. The PCR products either had symmetric dephosphorylated ends (OO) or assymetrical phosphothioated ends (OS or SO) arranged so that the protected strands will anneal.

Figure 9B:
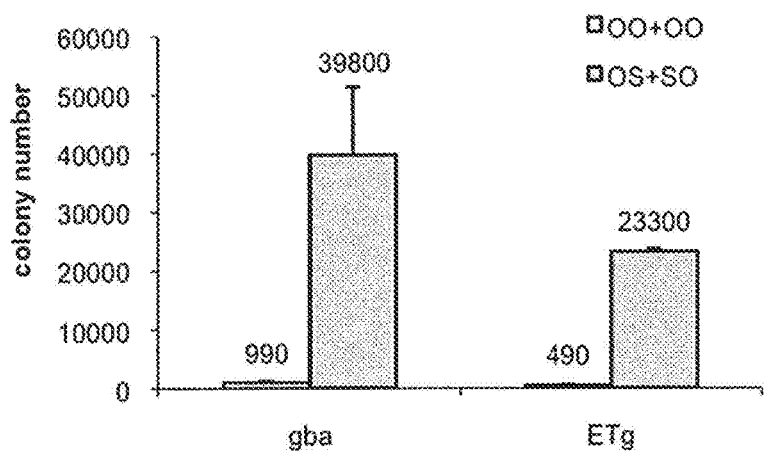

The data of FIG. 9B demonstrate that triple recombination using PCR products with phosphorothioation is far more efficient than using PCR products without phosphorothioation. Triple recombination mediated by full length RecE, RecT and Red gamma (ETg) is of comparable efficiency to that mediated by the Red system of Red alpha, Red beta and Red gamma. This is notable as it demonstrates that full length RecE is useful in applications which require a certain amount of LCHR. Optimally, better results may be obtained by concerted application of both Red and RecET systems.

Example 10—Quadruple Recombination—Two Oligos Plus a Large Fragment into a Circular Vector The integration of large cassettes is problematic due to the limitations of PCR, which can not handle large cassettes and which can introduce mutations. The method provided here utilises a double-homology recombineering strategy to first generate a cassette with flanking homology regions and then to recombine it into the target vector (31).

Figure 10:
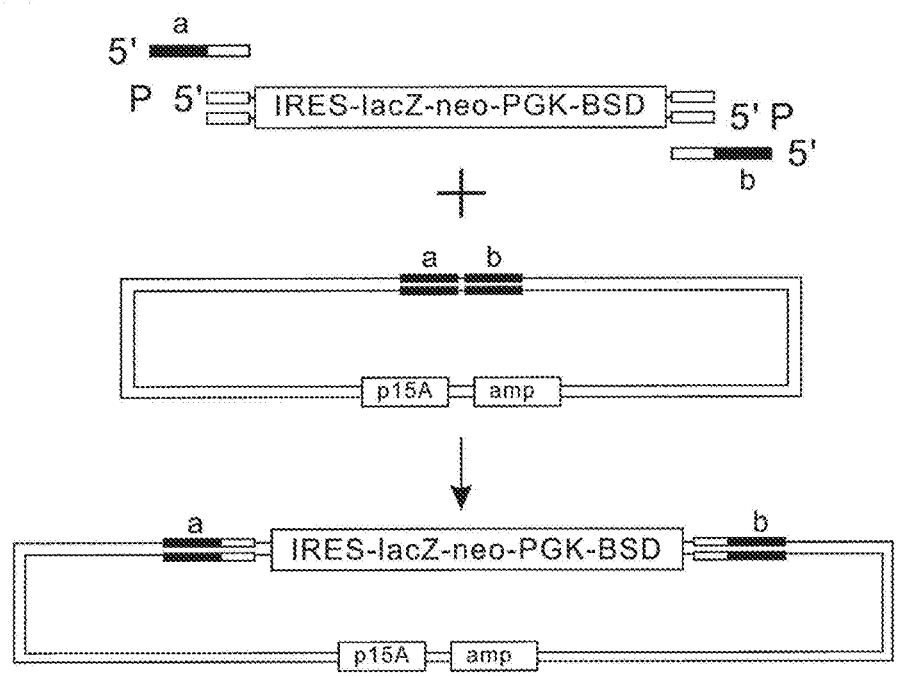
FIGS. 10A and 10B. Quadruple recombination mediated by Red or RecET.

To save one step of recombineering, quadruple recombination was developed by using two oligos to bridge the large linear molecule to the target vector (FIG. 10A). The oligos comprise regions of homology to the linear molecule and regions of homology to the target vector. The 100 nt oligonucleotides were synthesized to contain homology arms to each end of the linear molecule as well as the target regions in the vector. Hence the linear molecule does not need to be PCR amplified and so can be long (here an 8 kb IRES-lacZ-neo-PGK-BSD cassette), in addition to being free from the problem of PCR-based mutagenesis.

Figure 10B:
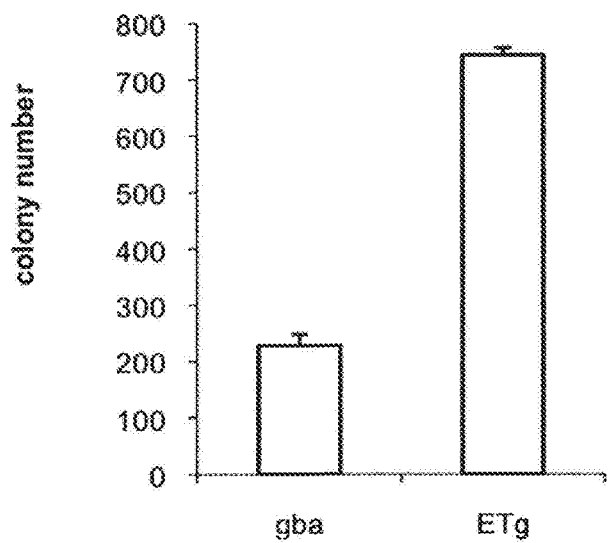

A large linear molecule carrying a functional cassette can be released from an existing plasmid, ideally a R6K origin based plasmid which cannot replicate in a normal *E. coli* strain. After co-transforming these three molecules into Red/ET proficient cells (GB2005) containing a target vector, the large linear molecule will be recombined into the vector via the oligo bridges (FIG. 10A). Here, a gene trapping cassette for mouse genome engineering, which is about 8 kb, was used to insert into mouse genomic clones using this technology. Full length RecE (RecETg) is more efficient than Red-gba at quadruple recombination (FIG. 10B).

Figure 11:
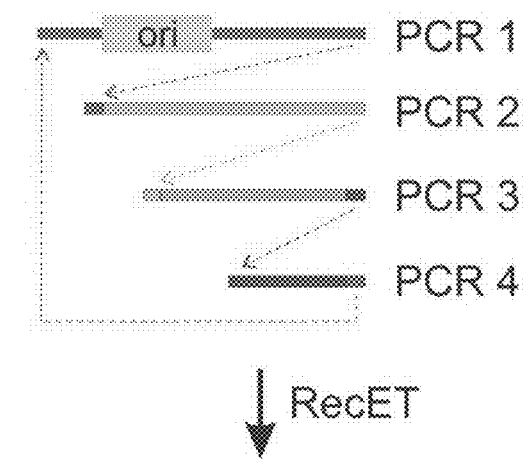
FIGS. 11A and 11B. Multiple linear DNA recombination.
Figure 11:
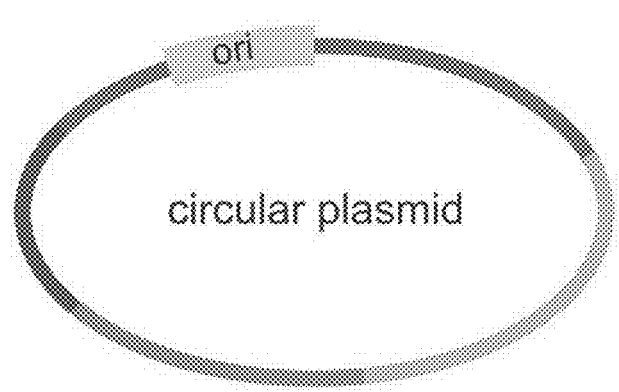
Figure 11B:
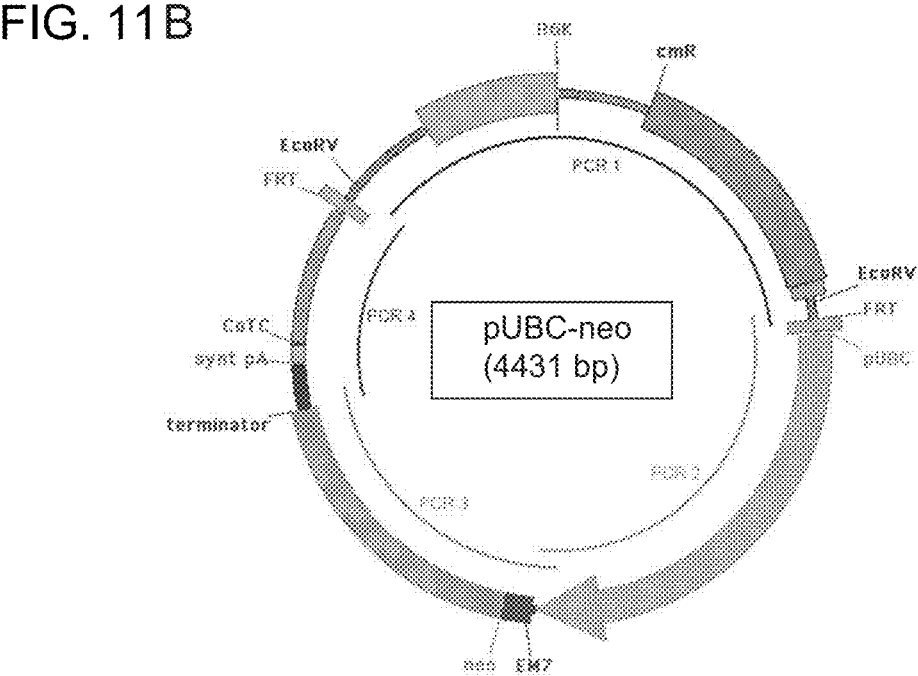

Example 11—Multi-Recombination—Two or More Linear Molecules into a Linear Vector A linear molecule can be recombined with a linear vector with high efficiency by homologous recombination (LLHR) mediated by the RecET system and full length RecE. The RecET system can be also applied to recombine multiple linear molecules with a linear vector, for example, in the generation of multi-fusion genes or operons (multiple genes separated by individual ribosomal binding sites). FIG. 11A is a diagram of this strategy and FIG. 11B is an exemplary experiment to generate a mammalian expression construct. Each PCR product has an overlapping region of sequence identity with its neighbour as indicated by the dotted arrows.

The final recombination product should contain a plasmid origin and a selectable gene. One linear vector (R6K-cm, 1680 bp) plus three functional cassettes with different size (1358 bp, 961 bp and 602 bp) were generated by PCR and co-transformed into GB2005-pir+pSC101-BAD-ETgA after L-arabinose induction of RecET. The 4 linear molecules were recombined by RecET through the short homology arms at the ends of each molecule in vivo. From 3 electroporations, 34 colonies were selected on kanamycin plates. Thirty two clones were verified by restriction analysis.

Example 12—cDNA Library Construction Using the RecET System

Figure 12A:
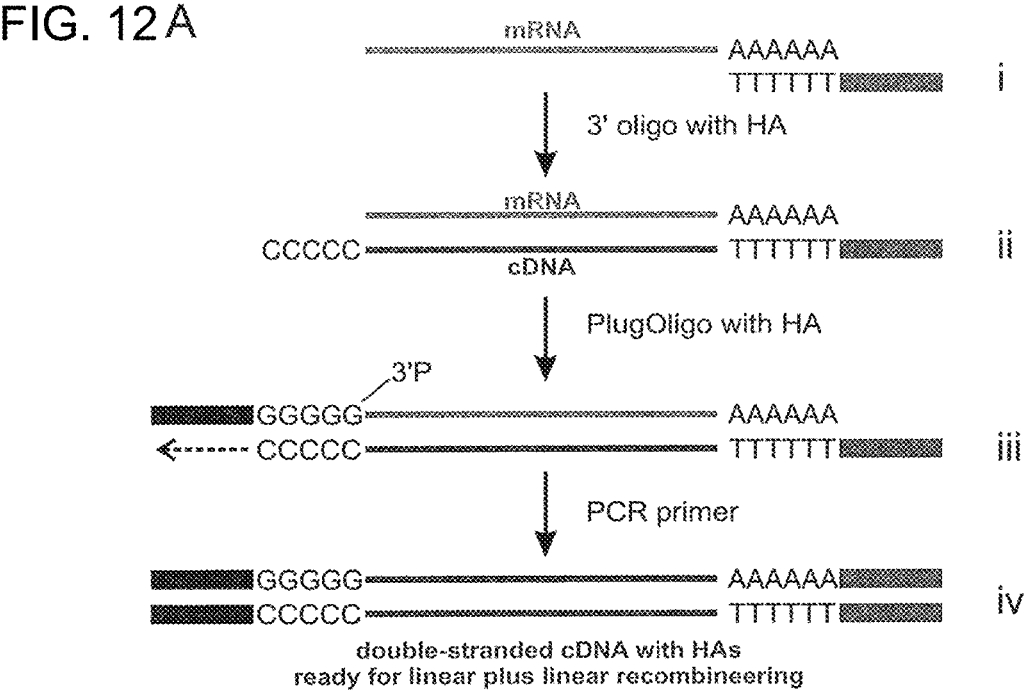
FIGS. 12A and 12B. Generation of cDNA libraries by LLHR.
Figure 12B:
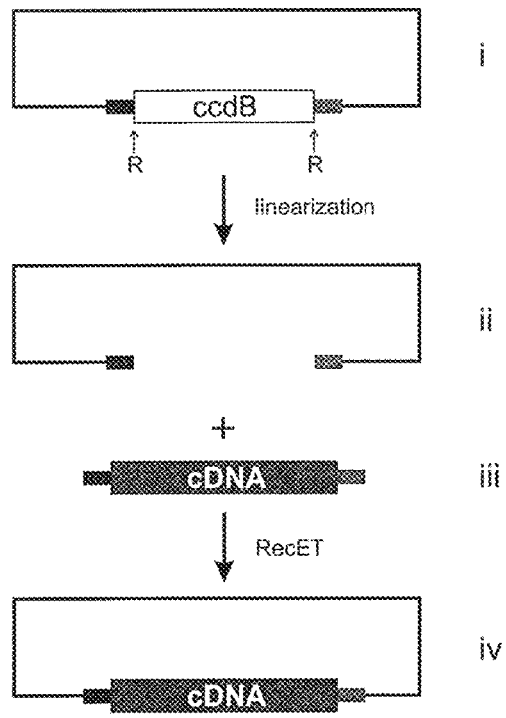

Usually cDNA library construction relies on the ligation of double-stranded cDNA molecules to a linear vector. Under the RecET system, LLHR has an absolute efficiency of more than $3 \times 10^6$ colonies per electroporation (FIG. 6B). Based on this high efficiency, a strategy for the construction of cDNA libraries using LLHR is provided (FIGS. 12A and 12B). As shown in FIG. 12A, i) a 3' oligonucleotide composed of a homology arm (HA; grey line) at its 5' end and a stretch of Ts at its 3' end will anneal to mRNA polyA tails and prime first strand cDNA synthesis with MMLV-based RT reverse transcriptase; ii) at the mRNA 5' end, the RT continues to add non-templated nucleotides, primarily deoxycytidines (dC), to the 3' end of the newly synthesized first strand cDNA; iii) a second oligonucleotide (known as a 'PlugOligo'), composed of a homology arm (grey line) at its 5' end and a stretch of Gs at its 3' end plus a 3' phosphate anneals to the C track and primes second strand synthesis. The final double-stranded cDNA has homology arms (HAs) for recombination with the cloning vector. The final product is a cDNA pool for cDNA library construction. This procedure can be easily altered to generate gene specific cDNA if specific primers are used in step iv.

The target vector containing the ccdB gene is digested to release the linear vector and expose the homology sequences at both ends. CcdB is a counterselectable gene and is used to reduce the background from undigested or re-joined vectors. Here the vector can be a series of expression vectors or simple cloning vectors. The double-stranded cDNA and the linearized cloning vector are transformed into RecETgA expressing GB2005-dir for linear to linear recombination. Screening of the desired clones can be carried out by conventional techniques or by using Red/ET recombineering technique as described later in Example 14 and 14. After cDNA pool formation, without library construction, a specific cDNA clone can be fished out by using a linear vector as shown in FIG. 12B but with the specific homology sequences to the specific cDNA. A cDNA clone larger than 5 kb was successfully cloned by LLHR. It was not possible to clone this from a conventional cDNA library.

Example 13—Cloning of a Target Sequence within a Linear Fragment

This example provides a method for cloning a target sequence without needing to rely on conveniently placed restriction sites. The BAC or genomic DNA pool (for example) is digested at a number of restriction sites which are not necessarily near to the target region. The target region remains intact. A linear vector is used with homology arms that define the region to be subcloned. The BAC DNA and vector are co-electroporated into an E. coli strain which expresses full length RecE and is able to perform LLHR. This results in recombination and the generation of a circular vector comprising the DNA of interest and, for example, the selectable markers of the linear vector.

In this exemplary experiment a number of target sequences were cloned from different BACs using the above strategy. As described in FIG. 13A, a BAC carrying a region for subcloning (darker section) was digested with a restriction enzyme so that the region for subcloning remained intact. A vector containing the p15A origin and an antibiotic resistance gene (ampicillin) was PCR amplified using oligonucleotides that were synthesized to contain two regions of sequence identity to the ends of the region to be subcloned. The BAC DNA and PCR product were co-electroporated into an E. coli strain (here GB2005) in which the full length RecE, RecT and Red gamma genes were expressed (here from pSC101-BAD ETg), followed by selection for ampicillin resistance.

Figures 13A, 13B:
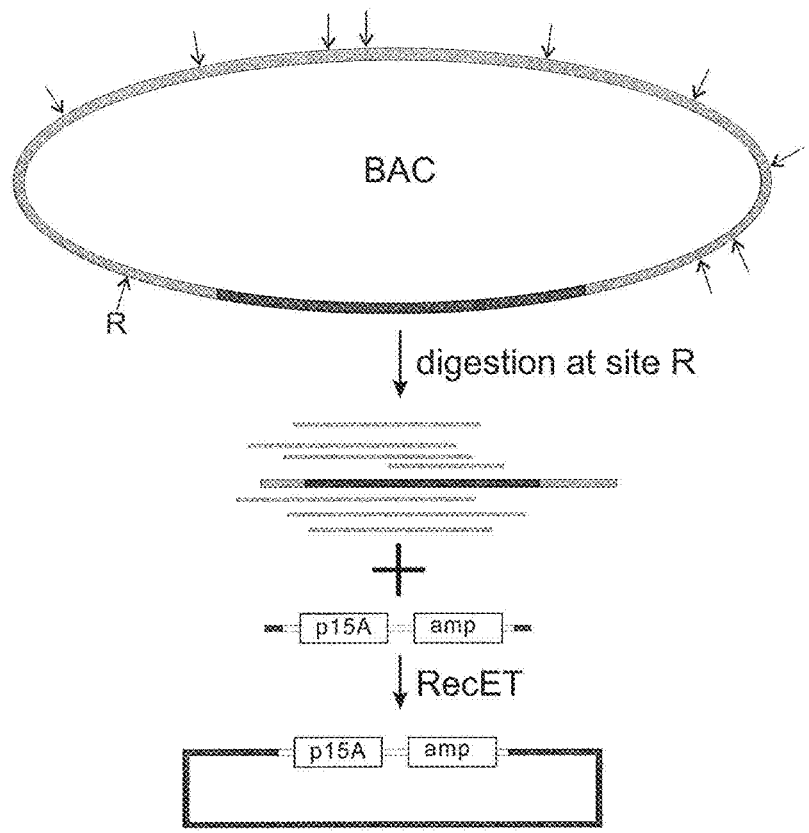
FIGS. 13A and 13B. Subcloning using LLHR mediated by full length RecET.

FIG. 13B summarises the results of the experiment. Four mammalian genes (mouse Swap70, Tmem56, Xist and human MeCP2) were subcloned by LLHR. The restriction enzymes used to cut the BACs carrying these genes is nominated, as is the distance from the nearest restriction site to the homology arm in the BAC. For example, with Swap70, BstZ17I was used to cut the BAC DNA and the region to be subcloned started 2778 bps from the nearest BstZ17I site at the 5' end and 2554 bps at the 3' end. Two independent experiments were performed for each insert. For example, with Swap70, 53 and 95 ampicillin resistant colonies grew on the plates in the two experiments, of which 18 each were examined by restriction mapping and 12 each were found to be correct. Restriction analysis confirmed that the majority of the clones were correct with the exception of the Tmem56 clone. This may be because it has long heterologous sequences at both ends. All of the incorrect products were found to be recircularized vector without any insert. Hence, intramolecular recombination is the major competing reaction and the main source of background.

Example 14—Direct Cloning of Gene or Gene Clusters from Genomic DNA Pool

Small genomic fragments can easily be cloned by PCR. But cloning of large fragment (over 15 kb) from genomic DNA is highly challenging and time consuming. A number of different steps are required including: genomic DNA preparation, digestion, ligation into a vector, transformation into a host, individual colony picking, library screen and subcloning. To simplify the procedure and increase the cloning efficiency, a direct cloning strategy based on LLHR is provided herein as shown in FIG. 14B. As shown in Example 13B, the incorrect products from LLHR are recircularized vectors. About 80% of recircularized vectors are formed by recombination of short repeats (less than 5 bp) or non-homology end joining within the 50 nucleotides of the outer sequence of a linear vector.

Figure 14A:
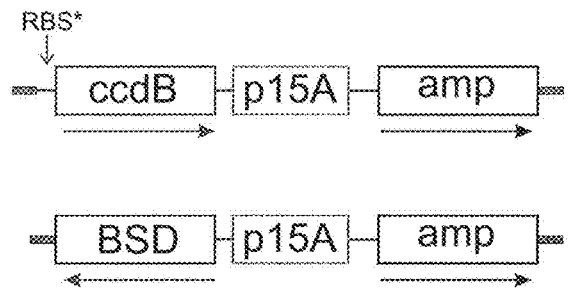
FIGS. 14A and 14B. Methods for optimizing direct cloning.
Figure 14B:
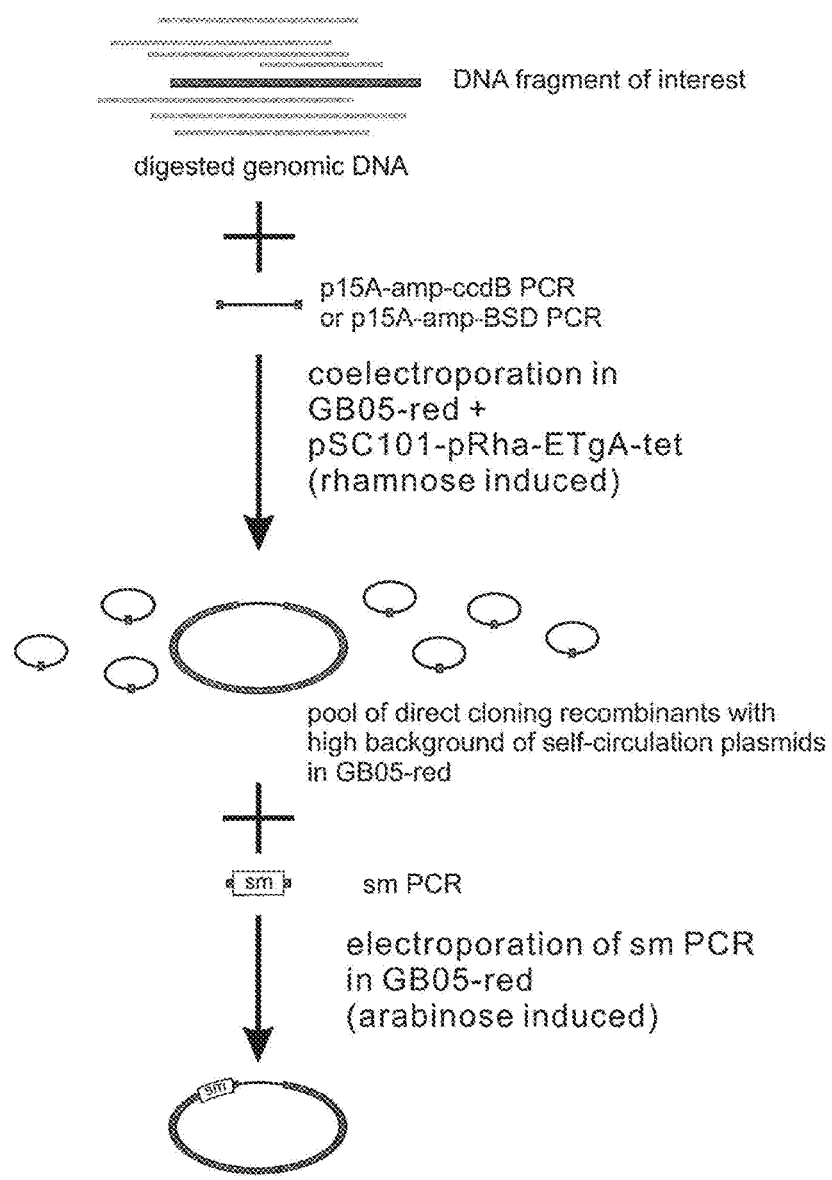

To solve this problem, two direct cloning vectors were generated (FIG. 14A). One is based on the suicide toxin gene ccdB. The 15A-amp-ccdB plasmid replicates in a gyrA246 host and is used as a template for the PCR product. ccdB is lethal in normal E. coli strains but permissive in strains carrying the gyrA246 mutation or expressing its partner ccdA. If the ends re-join, ccdB is driven by the amp promoter and the cell cannot survive in GB2005-dir, which has wild type gyrase. When a gene or gene clusters cloned from genomic DNA recombine in front of ccdB, there will be no promoter to drive ccdB expression and the correct clones can survive in GB2005-dir. This vector will reduce the self-circulation plasmid background by approximately 80%. However, there may be a risk of cryptic promoter activity from the cloned sequence activating ccdB and killing successful clones. An alternative solution to the above problem is a vector is utilising double-selection (p15A-amp-BSD) (lower section of FIG. 14A). The vector has two antibiotic resistance genes at the very ends of the vector. Most intramolecular recombination events will delete a part of one of these two genes hence rendering the intramolecular background sensitive to the corresponding antibiotic. The self-circularisation background will therefore be reduced.

Another strategy for the identification of the correct products is provided in FIG. 14B. This strategy employs LLHR and LCHR. This strategy is especially useful for the direct cloning of large fragments (over 40 kb) where the recombination efficiency is lower. The DNA (here illustrated as genomic DNA) is digested or sheared and co-electroporated with a linear vector with a selectable marker and homology arms that define the region to be targeted (for example, one of the vectors in FIG. 14A) into a LLHR-competent host containing full length RecE and RecT. After selection for, for example, ampicilin or ampicillin plus blasticidin, the resistant colonies are taken as a pool and electroporated with a linear DNA molecule encoding a selectable gene flanked by homology arms corresponding to part of the intended cloned region. The correct colonies will grow after selection for the last selectable gene.

To facilitate this strategy, which is essentially an LLHR step followed by an LCHR step, a combinatorial host was developed. This host, GB2005-red has the BAD-Red gbaRecA operon integrated into the chromosome so that arabinose induces the expression of Red gbaA. The plasmid pSC101-Rha-ETgA-tet, in which the RecE, RecT, Red-g and RecA are expressed after rhamnose induction, was also introduced. Hence the first illustrated LLHR step was performed after rhamnose induction and the second, LCHR step after arabinose induction. This host set-up can also be employed for triple and quadruple recombination experiments like those illustrated in Examples 9 and 10, to enhance efficiency.

Such a host, capable of LLHR and LCHR by expressing both RecET and Red systems, will be especially useful for cloning large segments of bacterial genomes, for example operons for the production of secondary metabolites.

Figure 15A:
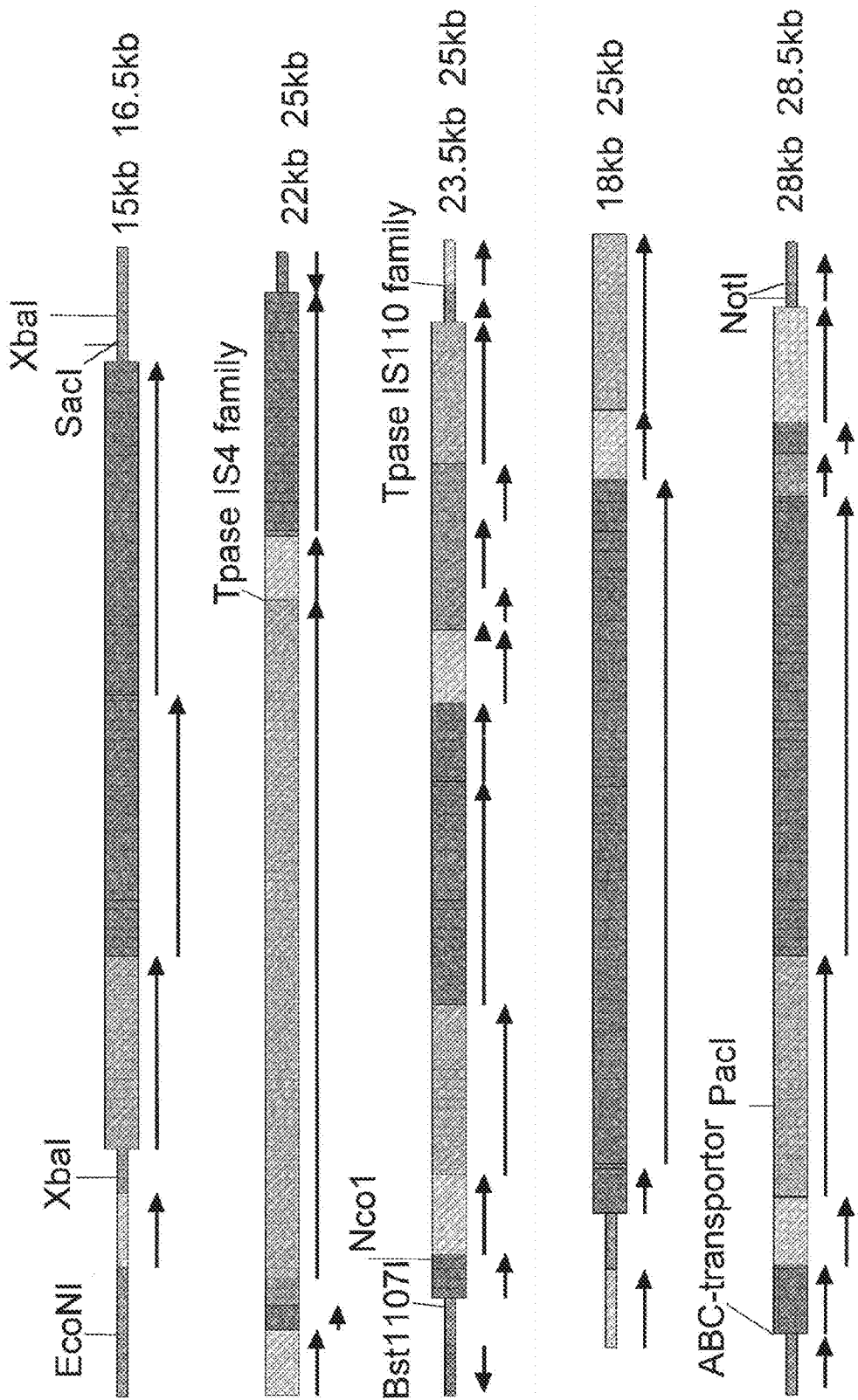
FIGS. 15A and 15B. Gene clusters related to secondary metabolic pathways identified in *Photorhabdus luminescens* DSM15139. The size of the gene cluster is indicated by the number immediately to the right of each cluster. The size of the region that was cloned is indicated by the number on the far right.
Figure 15B:
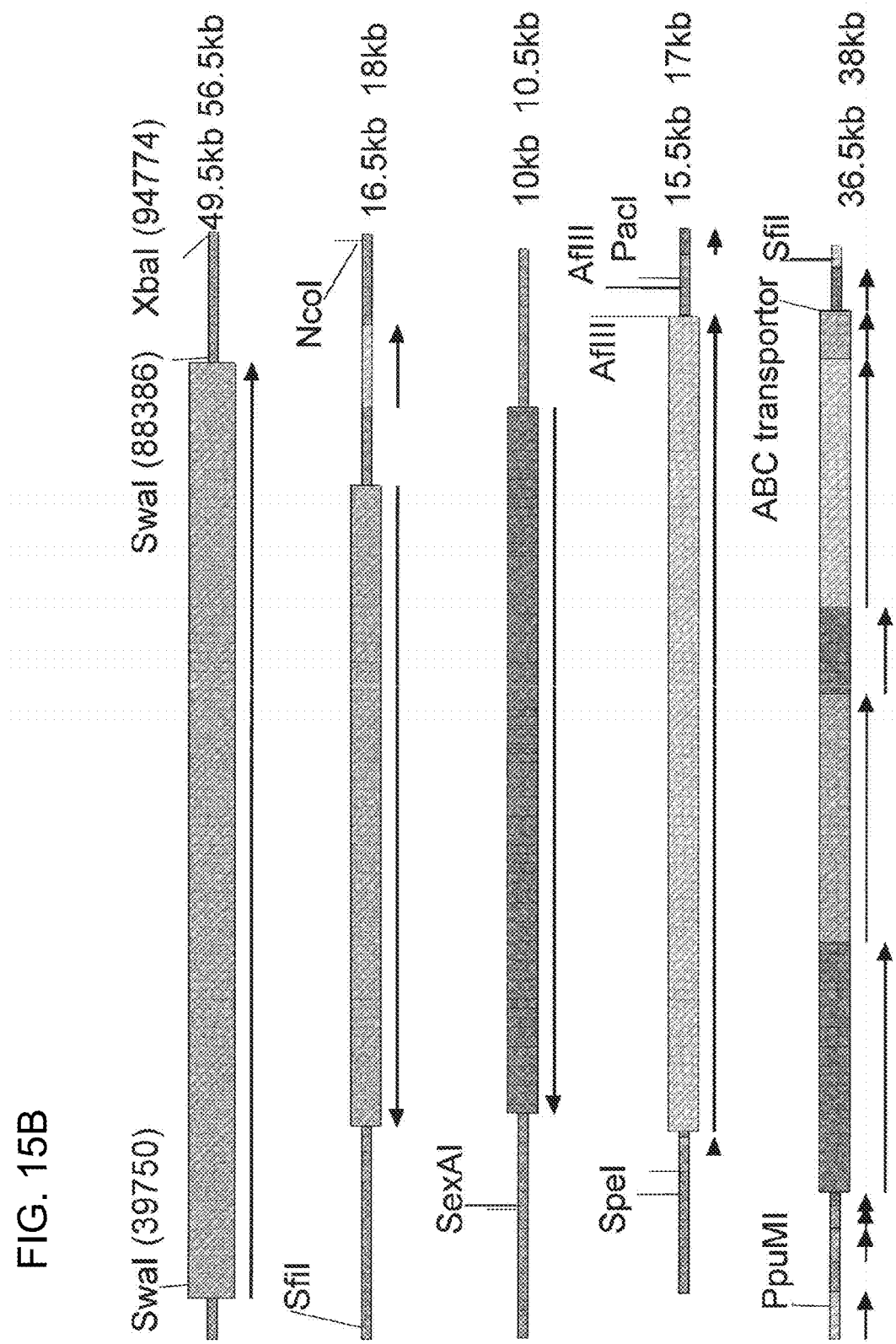

The utility of this strategy has been demonstrated in the direct cloning of a large gene cluster from *Photorhabdus luminescens* DSM15139. This species is a symbiotic of the entomopathogenic nematode Heterorhabditis bacteriophora which is an insect parasite used for the biological control of insects. The genome of *Photorhabdus luminescens* DSM15139 has been sequenced and is approximately 5.7 mb. More than 30 protein toxin genes are present in the chromosome which includes 10 silent or unknown PKS/NRPS gene clusters. Such secondary metabolite gene clusters are suitable targets for direct cloning mediated by ET recombination and full length RecE. FIGS. 15A and 15B provide 10 gene clusters that were identified in *Photorhabdus luminescens* DSM15139. The size of the gene cluster is indicated by the number immediately to the right of each cluster. The size of the region that was cloned is indicated by the number on the far right.

9 out of 10 of the gene clusters shown in FIGS. 15A 15B were directly cloned successfully in one round of ET recombination using ET recombination. Pairs of oligos were used to generate linear vectors carrying homology arms. Genomic DNA was linearised with the use of different restriction enzymes. LLHR was performed in YZ2005 and 12 colonies from each electroporation were picked into 96-deep-well plates for verification.

One gene cluster was not successfully cloned using this semi-high-throughput strategy. This cluster is plu3263 and is one of the largest genes found in bacterial genomes (first cluster in FIG. 15B). It is composed of 15 modules of non-ribosomal peptide synthetase. To directly clone this large region the vectors and strategy described above and in FIG. 14A were used.

Table 1a shows the successful utilisation of the vectors and strategy described above in the direct cloning of this large prokaryotic DNA cluster, from *Photorhabdus luminescens*. The target was 52616 bp or 50485 bp, as indicated in the first row by the presence or absence of ATG. The first row shows which linear construct was used, as described in FIG. 14A. The second row shows the amount of genomic DNA used for electroporation and the third row shows the time constant used for electroporation. The LLHR step of the strategy was carried out 8 times (columns 1-8). The LCHR step of the strategy was carried out 5 times for 7 of the 8 initial preparations (rows A-E). 15 clones had the insertion, 12 of which were correct, as verified by restriction analysis.

Table 1b shows the successful utilisation of the vectors and strategy described above in the direct cloning of eukaryotic DNA, the mouse gene hprt. The first LLHR stage was carried out with the vectors described in FIG. 14A, using the ccdB vector in the bottom half of the table and the BSD vector in the top half of the table. For each preparation, the LCHR stage of the protocol was carried out 5 times, (rows A-E). The correct insert was successfully generated in 4 clones

TABLE 1A

| Cloning of plu3263 | | | | | | | | |
|---|---|---|---|---|---|---|---|---|
| | 1 | 2 | 3 | 4 | 5 | 6 | 7 | 8 |
| P15A-amp (2 ug) | BSD | BSD | ccdB | ccdB | BSD no ATG | BSD no ATG | ccdB no ATG | ccdB no ATG |
| Genomic DNA (ug) | 5 | 10 | 5 | 10 | 5 | 10 | 5 | 10 |
| Time constant | 5.0 | 4.2 | 4.8 | 4.4 | 5.0 | Short cut | 5.2 | 4.4 |
| A | 25 | 2 | 2 | 1 | 8 | | 1 | 2 |
| B | 3 | 5 | 0 | 0 | 4 | | 4 | 1 |
| C | 3 | 3 | 1 | 6 | 10 | | 21 | 8 |
| D | 6 | 6 | 2 | 0 | 2 | | 30 | 0 |
| E | 1 | 1 | 0 | 0 | 5 | | 47 | 98 |
| Clones with insertion | 0/6 | 0/6 | 2/6 | 5/6 | 4/6 | | 2/6 | 2/6 |

TABLE 1A-continued

| Cloning of plu3263 | | | | | | | | |
|---|---|---|---|---|---|---|---|---|
|  | 1 | 2 | 3 | 4 | 5 | 6 | 7 | 8 |
| Correct clones |  |  | 2 | 5 | 2 |  | 2 | 1 |

8 electroporations of linear plus linear + 35 electroporations of linear plus circular
Colonies: 308
Clones with insertion: 15/42
Correct clones: 12/42

TABLE 1B

| Cloning of hprt | | | | |
|---|---|---|---|---|
| L. + L. | 1 (BSD) | | 2 (BSD) | |
| L. + C. | cm | result | cm | result |
| A | 124 | 10/24 with insert | 116 | 11/24 with insert |
| B | 26 | 2 correct | 69 | 1 correct |
| C | 376 |  | 37 |  |
| D | 81 |  | 272 |  |
| E | 14 |  | 31 |  |
| L. + L. | 3 (ccdB) | | 4 (ccdB) | |
| L. + C. | cm | result | cm | result |
| A | 276 | 17/24 with insert | 680 | 21/24 with insert |
| B | 24 | 0 correct | 176 | 1 correct |
| C | 136 |  | 192 |  |
| D | 592 |  | 488 |  |
| E | 240 |  | 456 |  |

Example 15—LLHR is Replication Independent but LCHR is Replication Dependent

A transformed linear molecule in an E. coli cell expressing Red-gba or RecETg will be digested by exonucleases Red-alpha or RecE from the 5' end to the 3' end to expose a 3' single-stranded end. Although the donor is a linear molecule in both LCHR and LLHR, the recipient is a circular replicatable vector in LCHR and is a linear vector in LLHR. There is a fundamental difference between the two situations. Since the circular molecule is intact in LCHR, the linear molecule processed by Red-alpha or RecE will invade into the replication folks where the homology sequence is exposed. In LLHR, both the linear molecules will be processed by Red-alpha and RecE and the single-stranded homology sequences will be exposed after the reaction. The annealing of both molecules in vivo is promoted by RecET. This difference between LCHR and LLHR allowed the inventors to predict that LCHR is replication dependent whilst LLHR is not replication dependent.

Figure 16A:
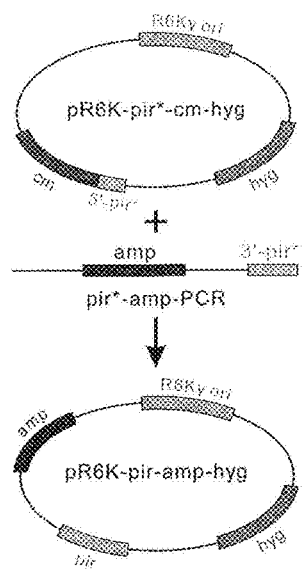
FIGS. 16A-16D. LLHR and LCHR are mechanistically distinct with respect to their reliance on DNA replication.
Figure 16B:
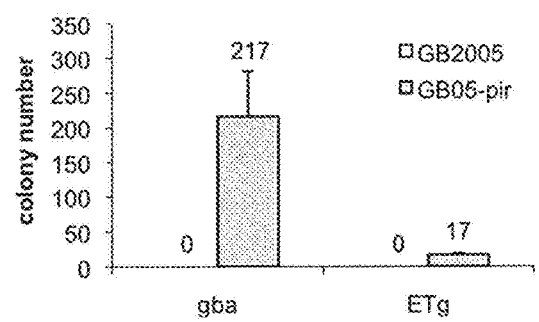

To prove this, two experiments were designed using the R6K replication origin. The protein product of the pir gene is required to initiate replication from R6K (33 ref of pir). The R6K origin and the pir gene can be separated and any plasmid carrying the R6K origin alone can be propagated in a strain expressing pir gene. The GB2005-pir strain was generated by inserting the pir gene in the chromosome of GB2005. GB2005 does not have pir and therefore cannot replicate plasmids with the R6K origin. FIG. 16A is a schematic diagram of the experiment to test whether LCHR can occur independently of replication. Plasmid pR6K-pir*-cm-hyg has only the 5' part of the pir gene. This plasmid cannot replicate in the pir− strain GB2005. The PCR product of pir*-amp has the 3' part of the pir gene. There is homology between the two parts of the pir gene to allow recombination. Through recombination of the PCR product and the plasmid, the resulting plasmid pR6K-pir-amp-hyg, which has a complete pir gene, can replicate in both pir− strain GB2005 and pir+ strain GB2005-pir. As shown in FIG. 16B, no recombination occurred in the pir− strain GB2005. However, in the pir+ strain GB2005-pir, where replication is occurring, recombination did occur. This demonstrates that for LCHR to occur, replication of the plasmid must be occurring. As this is LCHR, cells expressing gba mediated the recombination more efficiently than RecETg.

Figure 16C:
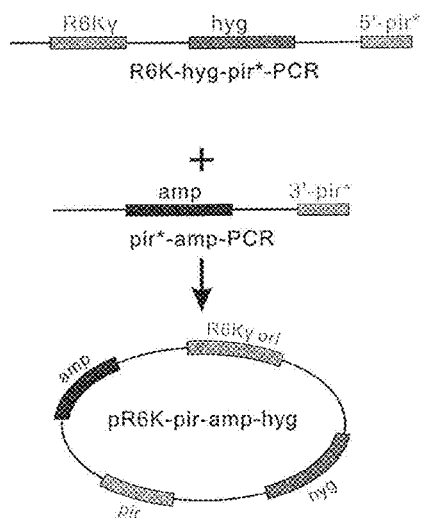
Figure 16D:
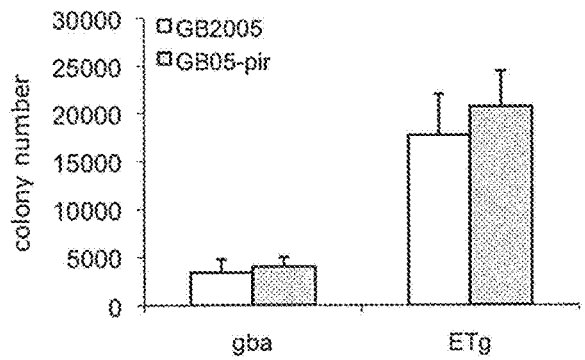

The equivalent experiment, as described in FIG. 16C, was used to investigate whether LLHR requires replication to be occurring. The same linear molecule pir*-amp was used for LLHR but the recipient was a linear vector R6K-hyg-pir* generated by PCR using pR6K-pir*-cm-hyg as template (FIG. 16C). R6K-hyg-pir*-PCR has only the 5' part of the pir gene and the replication origin R6K. The PCR production of pir*-amp has the 3' part of the pir gene. LLHR of the two PCR products results in plasmid pR6k-pir-amp-hyg, which replicates in both pir− strain GB2005 and pir+ strain GB2005-pir (FIG. 16C). When LLHR was used, recombination occurred in both GB2005 and GB2005-pir with expression of Red-gba and RecETg (FIG. 16D). Therefore, LLHR is replication independent and can occur without pir and without replication (in strain GB2005). The use of full length RecE in the ETg system was most efficient (FIG. 16 D), demonstrating that full length RecE is most suited for mediating such recombination.

Example 16—Recombination is Affected by Modified Ends in Linear Molecule

Figure 17A:
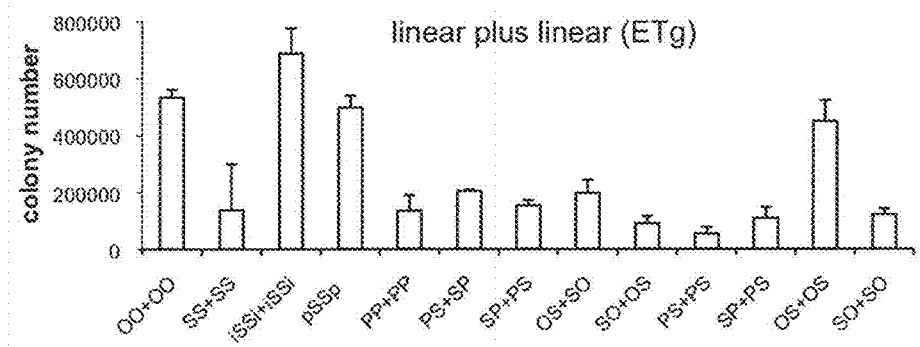
FIGS. 17A-17D. Effect on LCHR and LLHR of PCR products with different ends. LLHR (FIG. 17A.
Figure 17B:
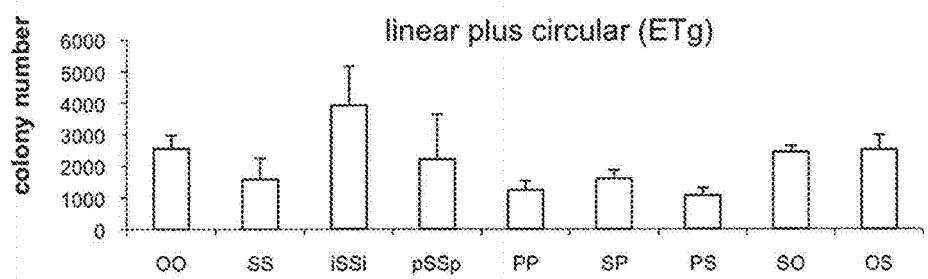

Exonucleases Red-a and RecE work on the 5' end of a double strand break. RecE degrades one strand from the 5' end to the 3' end without phosphorylation at the 5' end but Red-a needs 5' end phosphorylation to process the degradation (34 ref—Red-a and RecE). A linear DNA molecule without phosphorylation at the 5' end (for example, a PCR product produced by using oligos without modification) has to be phosphorylated first at the 5' end in vivo before Red-a can process it. Since the modification of the ends of molecules has an effect on exonuclease activity, the effect of modifications of linear molecules on LLHR and LCHR was studied. 5 oligos with different 5' ends were used in the experiments: no modification (O); phosphorylation (P); phosphorothioation(S); no modification at the 5' end but with internal phosphorothioation at nucleotide 51 where homology ends (iS); and phosphorylation at the 5' end also with internal phosphorothioation at nucleotide 51 (pS). In the model experiments as described in Example 1, PCR products with symmetric ends or asymmetric ends were generated by using these oligos and the homology is 50 bp in the PCR products. In the linear double-stranded PCR products, the strand without 5' end modification can be digested by RecE directly or Red-α after phosphorylation in vivo; the strand with 5' end phosphorylation can be digested by Red-α and RecE directly; the strand with 5' end phosphorothioation cannot be digested by both Red-α and RecE; the strand with no modification at 5' end but with an internal phosphorothioation at 51 nt can be digested by RecE until 50 base to expose exact homology in another strand; and the strand with phosphorylation at 5' end and an internal phosphorothioation at 51 nt can be directly digested by both Red-α and RecE until base 50 to expose exact homology in another strand. LCHR (FIGS. 17A and 17C) and LLHR (FIGS. 17B and 17D) using these PCR products were tested in GB2005 with expression of Red-gba (FIGS. 17C and 17D) or RecETg (FIGS. 17A and 17B).

In LCHR, a linear double-stranded molecule has 25 possible combinations of two strands with different ends and 9 of them were tested. Because both of the molecules are linear in LLHR, 625 combinations can be generated but only 13 were tested here. In LCHR with expression of RecETg (FIG. 17 B), the PCR product with iSSi gives the highest efficiency but there is little difference between the other modifications and the OO product, which has no modifications. In LLHR with expression of RecETg (FIG. 17A), the combination of two linear PCR products with iSSi+iSSi gives the highest efficiency. pSSp+pSSp and OS+OS have similar efficiency to OO+OO (no modifications) but all of the other combinations have a lower efficiency. In both LCHR and LLHR, phosphorothioation at nucleotide 51 gives the highest efficiency or at least does not reduce efficiency. This can be explained by the fact that if the linear molecules are protected by internal phosphorothioation and the homology sequences are exposed at the 3' ends, this encourages recombination. All of the combinations containing phosphorothioation at one end, which lead to a single stranded DNA after recE digestion, have a lower efficiency in LLHR (except OS+OS) (FIG. 17A).

Figure 17C:
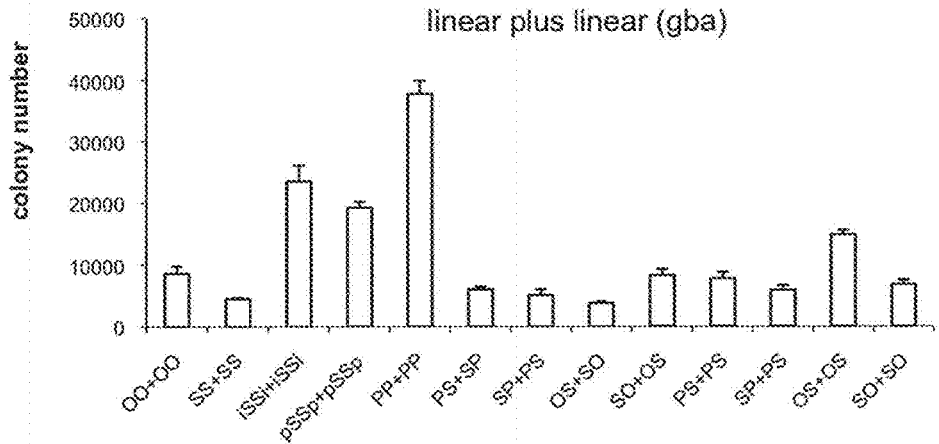
Figure 17D:
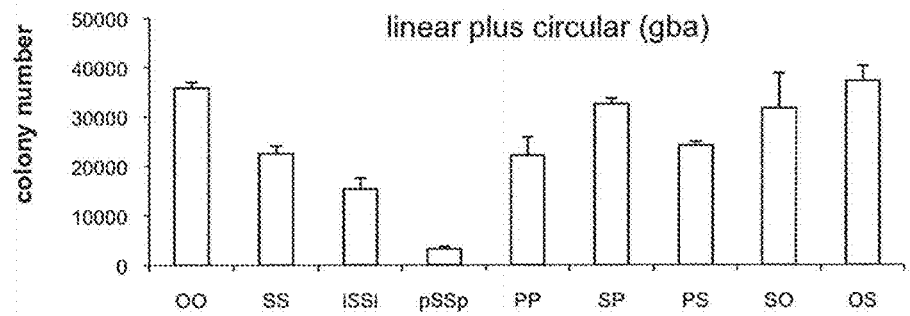

With expression of Red-gba in LLHR, the PP+PP combination is the most efficient (FIG. 17C). Combinations containing internal phosphorothioation at the 5' end (iSSi+iSSi and pSSp+pSSp) work better than combinations with no modifications (OO+OO) (FIG. 17C). All other combinations have lower or similar efficiency to the OO+OO combination (FIG. 17C). In LCHR with expression of Red-gba, the result is the opposite to LLHR (FIG. 17D). Linear molecule with pSSp have the lowest efficiency. Linear molecules with iSSi have a lower efficiency than OO (FIG. 17D). The other combinations are equally efficient or less efficient than non-modified OO (FIG. 17D).

Figure 18:
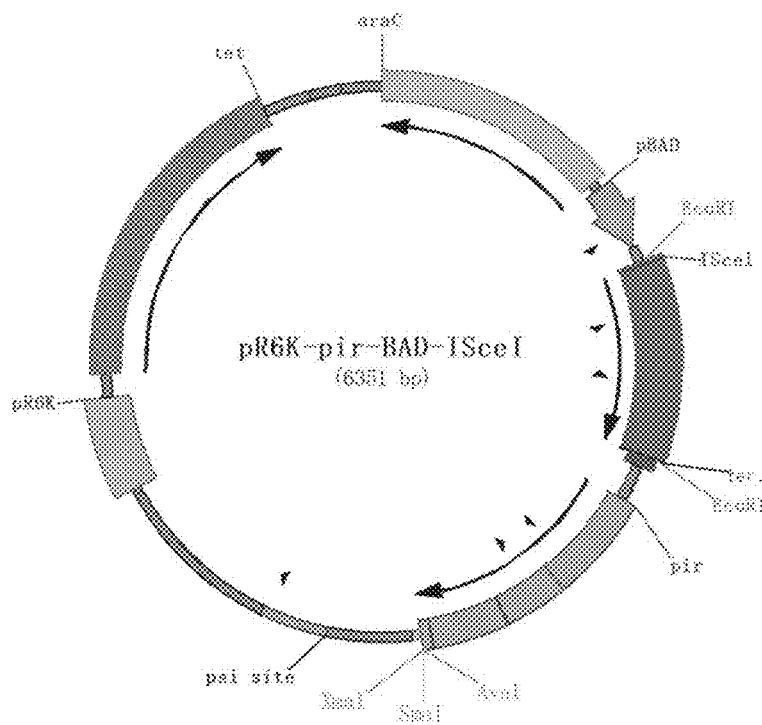
FIG. 18. I-SceI enzyme expression construct. Plasmid map of pR6K-dir-BAD-ISceI. This plasmid has a synthetic I-SceI coding sequence under PBAD promoter which is regulated by arabinose.

Example 17—Increased Recombination Frequency by Using Linearised Vector Generated In Vivo A synthetic I-SceI gene was inserted into a vector under an arabinose inducible promoter. The expression plasmid was a R6K origin based plasmid and it was compatible with BAC, p15A or pBR322 origin based plasmids (FIG. 18). The recognition site of I-SceI is the 30 bp sequence: 5' AGT-TACGCTAGGGATAACAGGGTAATATAG 3' (SEQ ID NO: 2).

Figure 19A:
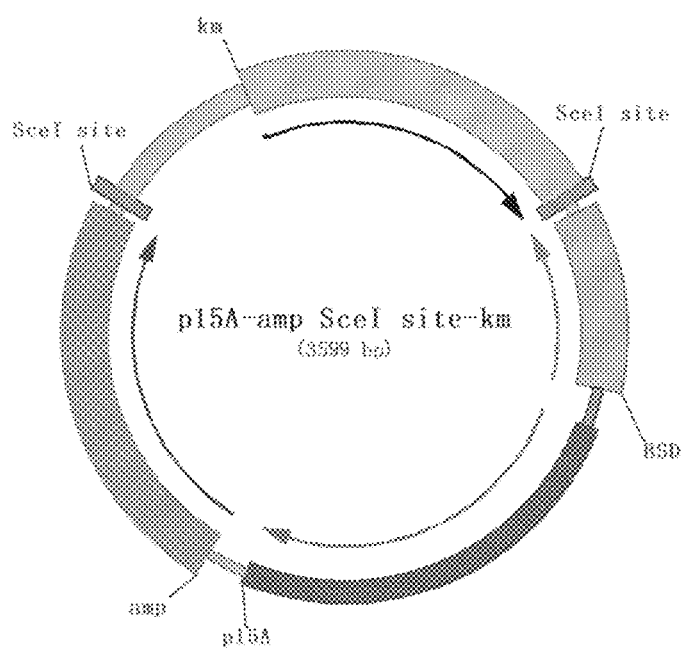
FIGS. 19A and 19B. Direct cloning recipient vector and its digestion in vivo.

The recipient plasmid for the direct cloning experiment was the direct cloning recipient p15A origin-based plasmid shown in FIG. 19A. In this plasmid, a kanamycin resistant gene is flanked by two I-SceI recognition sites. Ampicillin and blasticidin resistant genes are also present in the backbone.

Figure 19B:
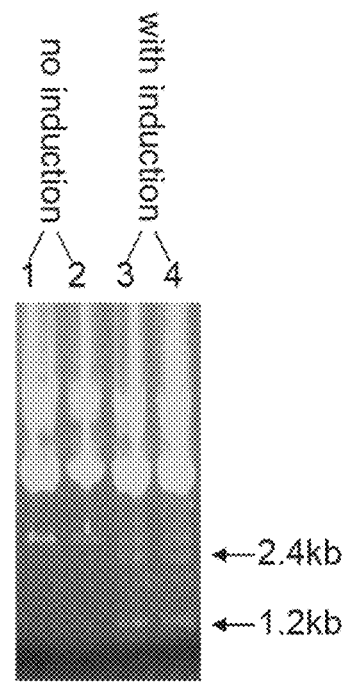

When the I-SceI expression plasmid and the recipient plasmid were transformed into a GB2005-dir cell, two linear fragments were produced after induction of I-SceI expression by L-arabinose (FIG. 19B). The first linear fragment represented the kanamycin resistance gene which was flanked by the two I-SceI recognition sites. The second linear fragment represents the backbone of the vector that remained following the excision of the fragment encoding the kanamycin resistance gene. The activity of I-SceI in vivo is low because less than 10% recipient plasmids were linearised. However, this experiment shows that I-SceI does linearise the recipient plasmid in vivo.

Figure 20:
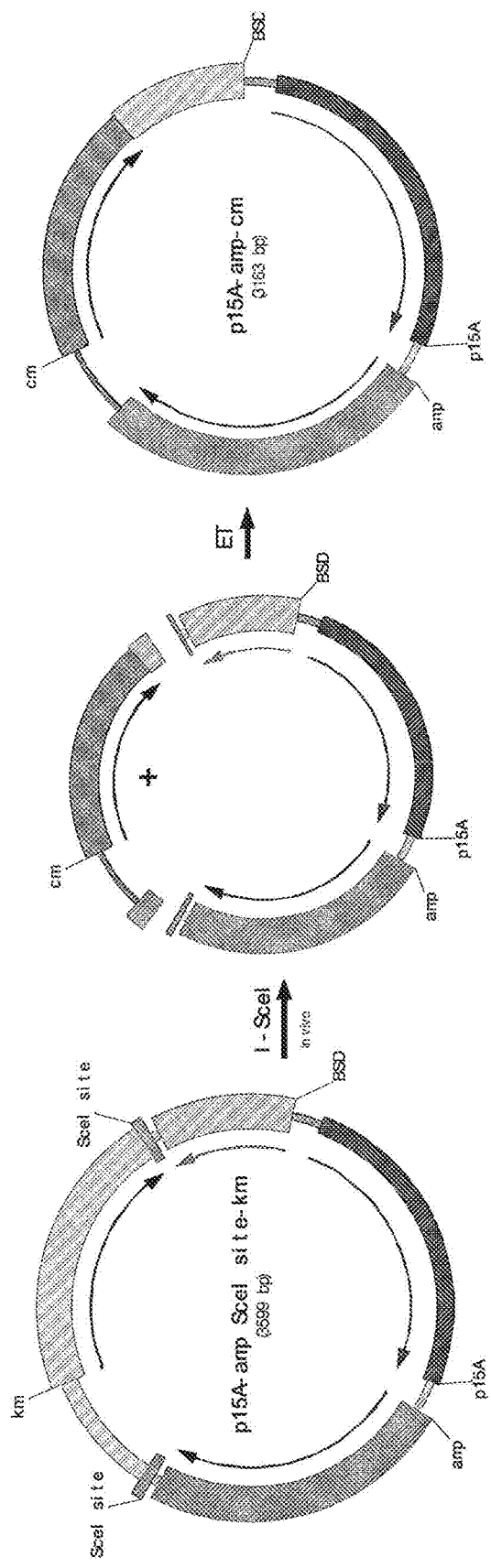
FIG. 20. Pathway of in vivo I-SceI cleavage and cloning by homologous recombination. The cloning vector is linearised by I-SceI in vivo. The linearised vector is then recombined with cm (chloramphenicol) PCR product by RecET via the homology arms at the ends of the cm PCR product to form recombinants.
Figure 21:
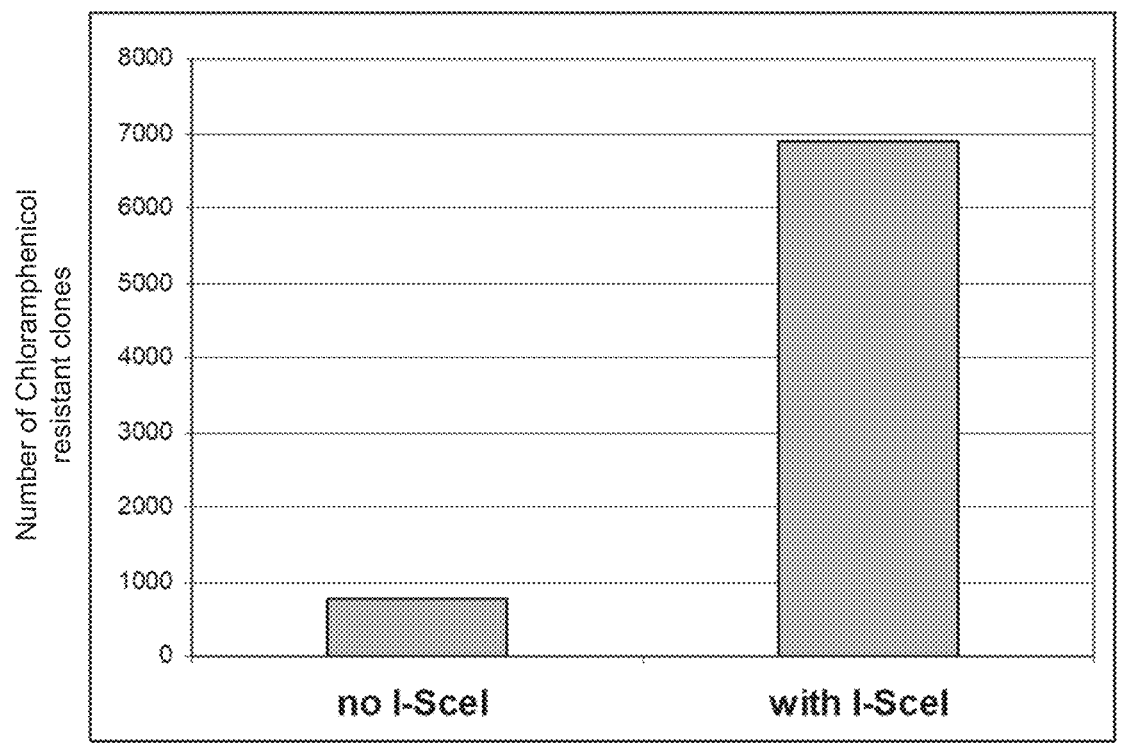
FIG. 21. Linear to linear recombination in vivo. This graph shows the recombination efficiency with and without I-SceI expression in vivo (each column represents 4 independent electroporations). Without expression from the I-SceI plasmid, circular recipient plasmids were recombined with cm PCR product by RecET, producing recombinant plasmids encoding a chloraphenicol resistance protein with low efficiency (758). With I-SceI expression, some of the recipient plasmids were linearised and recombined with cm PCR product by RecET with high efficiency, producing approximately 10-fold more chloraphenicol resistant colonies (6890) compared to when I-SceI was not expressed.

GB2005-dir is an *E. coli* strain carrying an ETgA (recE, recT, red gamma and recA) operon on its chromosome under the Para-BAD promoter. This strain was transformed with both the I-SceI homing endonuclease expression vector and the recipient vector. When L-arabinose was added to the GB2005-dir culture, the recombination proteins (ETgA) and I-SceI were all expressed. I-SceI then linearized the recipient plasmid in vivo. After 1 hour induction, electrocompetent cells were prepared and transformed by a cm (chloramphenicol resistance gene) PCR product, using standard techniques. The cm PCR product comprises the chloramphenicol resistance gene and homology arms at both ends (i.e. flanking the chloramphenicol resistance gene) having homology to the recipient vector (FIG. 20). Following transformation, LLHR of the cm PCR product and the linearised recipient vector occurred. FIG. 21 shows the recombination rate with and without I-SceI expression plasmid (as determined by the number of colonies on a chloramphenicol supplemented agar plate). The data indicate that recombination efficiency is dramatically improved (~10 fold) by linearization of the recipient vector in vivo.

This experiment is proof of principal for improvement of direct cloning via linearization of the recipient vector in vivo.

The invention has been described above by way of example only and it will be appreciated that further modifications may be made that fall within the scope of the claims. All citations are incorporated by reference in their entirety.

TABLE 2

List of plasmids and strains

| Name | Description | Source |
|---|---|---|
| P15A-cm | Recombineering substrate, PCR template | this work |
| pUBC-neo | PCR template, Recombineering product | this work |
| P15A-cm-kan | Recombineering product | this work |
| pR6K-pir*-cm-hyg | Recombineering substrate, PCR template | this work |
| pR6K-pir-amp | PCR template | this work |
| BAC-mll-neo* | Recombineering substrate | Ref. 22 |
| PBAD24 | Recombineering substrate | Ref. |
| pR6K-PGK-EM7-neo | PCR template | this work |
| pR6K-IRES-IacZneo-PGK-BSD | Recombineering substrate | this work |
| P15A-amp-setd1b | Recombineering substrate | this work |
| pSC101-BAD-ba-tet | Expression plasmid | this work |
| pSC101-BAD-gba-tet | Expression plasmid | Ref. 22 |
| pSC101-BAD-gbaA-tet | Expression plasmid | Ref. 27 |
| pSC101-BAD-ET-tet | Expression plasmid | this work |
| pSC101-BAD-ETg-tet | Expression plasmid | this work |
| pSC101-BAD-ETgA-tet | Expression plasmid | this work |
| pSC101-BAD-E141Tg-tet | Expression plasmid | this work |
| pSC101-BAD-E282Tg-tet | Expression plasmid | this work |
| pSC101-BAD-E423Tg-tet | Expression plasmid | this work |
| pSC101-BAD-E564Tg-tet | Expression plasmid | this work |

TABLE 2-continued

List of plasmids and strains

| Name | Description | Source |
|---|---|---|
| pSC101-BAD-E602Tg-tet | Expression plasmid | this work |
| pSC101-BAD-gam-tet | Expression plasmid | this work |
| pSC101-BAD-Eg-tet | Expression plasmid | this work |
| pSC101-BAD-E(1-601)Tg-tet | Expression plasmid | this work |
| pSC101-pRha-ETgA-tet | Expression plasmid | this work |
| pSC101-BAD-ETgA-hyg | Expression plasmid | this work |
| pSC101-tetR-tetO-ETgA-hyg | Expression plasmid | this work |
| pSC101-BAD-gbaA-amp | Expression plasmid | this work |
| pSC101-Rha-gbaA-amp | Expression plasmid | this work |
| pSC101-tetR-tetO-gbaA-amp | Expression plasmid | this work |
| P15A-amp-BSD | PCR template | this work |
| P15A-amp-ccdB | PCR template | this work |
| YZ2005 | YZ2000*, rpsL | this work |
| DH10B** | E. coli strain | Research Genetics |
| HS996 | DH10B. fhuA::IS2; phage T1-resistant | Research Genetics |
| GB2005 | HS996, ΔrecET Δ ybcC | Ref. 25 |
| GB05-pir | GB2005, pir | this work |
| GB05-dir | GB2005, pBAD-ETgA | this work |
| HS996-BAD-ET | HS996, pBAD-ET | this work |

*YZ2000 genotype: thr-1 leu-6 thi-1 lacY1 galK2 ara- 14 xyl-5 mtl-1 proA2 his-4 argE3 str-31 tsx-33 supE44 recB21, recC22, sbcA23, rpsL31, tsx-33, supE44, his-328, mcrA, mcrBC, mrr, hsdMRS
**DH10B genotype: F- mcrA Δ(mmr-hsdRMS-mcrBC) Φ80dlacZ ΔM15 ΔlacX74 endA1 recA1 deoR Δ(ara, leu)7697 araD139 galU galK nupG rpsL λ-

TABLE 3

Drug selectable markers

| Abbreviation | Resistance | Concentration (μg/ml) | Gene |
|---|---|---|---|
| cm | Chloramphenicol | 15 | chloramphenicol acetyl transferase (cat) from Tn9 |
| neo | Kanamycin | 15 | kanamycin and neomycin phosphotransferase II (nptII) from Tn5 |
| kan | Kanamycin | 15 | kanamycin phosphotransferase (aph) from Tn903 |
| hyg | Hygromycin-B | 40 | hygromycin phosphotransferase (hphB) from *Streptomyces hygroscopicus* |
| amp | Ampicillin | 100 | TEM-1 beta-lactamase (bla) from Tn3 |
| tet | Tetracycline | 5 | tetracycline efflux protein (class C tetA or tetA(C)) from pSC101 |
| BSD | Blasticidin-S | 40 | blasticidin S deaminase (BSD) from *Aspergillus terreus* |

REFERENCES

1. Bubeck, P., Winkler, M. & Bautsch, W. Rapid cloning by homologous recombination in vivo. *Nucleic Acids Res.* 21, 3601-3602 (1993).
2. Oliner, J. D., Kinzler, K. W. & Vogelstein, B. In vivo cloning of PCR products in *E. coli*. *Nucleic Acids Res.* 21, 5192-5197 (1993).
3. Degryse, E. In vivo intermolecular recombination in *Escherichia coli*: application to plasmid constructions. *Gene* 170, 45-50 (1996).
4. Chartier, C. et al. Efficient generation of recombinant adenovirus vectors by homologous recombination in *Escherichia coli*. *J. Virol.* 70, 4805-4810 (1996).
5. Clark, A. J. et al. Genes of the RecE and RecF pathways of conjugational recombination in *Escherichia coli*. *Cold Spring Harb. Symp. Quant. Biol.* 49, 453-462 (1984).
6. Hall, S. D., Kane, M. F. & Kolodner, R. D. Identification and characterization of the *Escherichia coli* RecT protein, a protein encoded by the recE region that promotes renaturation of homologous single-stranded DNA. *J. Bacteriol.* 175, 277-287 (1993).
7. Zhang, Y., J. P. P. Muyrers, G. Testa, and A. F. Stewart. 2000. DNA cloning by homologous recombination in *Escherichia coli*. *Nat. Biotechnol.* 18:1314-1317.
8. Bhargava, J. et al. Direct cloning of genomic DNA by recombinogenic targeting method using a yeast-bacterial shuttle vector, pClasper. *Genomics* 62, 285-288 (1999).
9. Bradshaw, M. S., Bollekens, J. A. & Ruddle, F. H. A new vector for recombination based cloning of large DNA fragments from yeast artificial chromosomes. *Nucleic Acids Res.* 23, 4850-4856 (1995).
10. Bhargava, J. et al. Direct cloning of genomic DNA by recombinogenic targeting method using a yeast-bacterial shuttle vector, pClasper. *Genomics* 62, 285-288 (1999).
11. Shashikant, C. S., Carr, J. L., Bhargava, J., Bentley, K. L. & Ruddle, F. H. Recombinogenic targeting: a new approach to genomic analysis—a review. *Gene* 223, 9-20 (1998).
12. Larionov, V. Direct isolation of specific chromosomal regions and entire genes by TAR cloning. *Genet. Eng.* 21, 37-55 (1999).
13. Zhang Y, Buchholz F, Muyrers J P and Stewart A F. A new logic for DNA engineering using recombination in *Escherichia coli*. *Nature Genetics*. 20 (2): 123-8, 1998.
14. Muyrers J P, Zhang Y, Buchholz F, Stewart A F. RecE/RecT and Redα/Redβ initiate double stranded break repair by specifically interacting with their respective partners. *Genes & Dev.* 14:1971-1982, 2000.
15. Yu, D., Ellis, H. M., Lee, E. C., Jenkins, N. A., Copeland, N. G., and Court, D. L. (2000) An efficient recombination system for chromosome engineering in *Escherichia coli*. *Proc. Natl. Acad. Sci. USA* 97, 5978-5983.
16. Muyrers J P, Zhang Y, Testa G, Stewart A F. Rapid modification of bacterial artificial chromosomes by ET-recombination. *Nucleic Acids Res.* 27 (6): 1555-1557, 1999.
17. Muyrers J P, Zhang Y, Benes V, Testa G, Ansorge W, Stewart A F. Point mutation of Bacterial Artificial Chromosome by ET recombination. *EMBO reports*. 1:239-243, 2000.
18. Angrand P O, Daigle N, van der Hoeven F, Schöler H R, Stewart A F. Simplified generation of targeting constructs using ET recombination. *Nucleic Acids Res.* 1999 Sep. 1; 27 (17): e16.
19. K Narayanan, R Williamson, Y Zhang, A F Stewart & P A Ioannou. Efficient and precise engineering of a 200 kb-globin human/bacterial artificial chromosome in *E. coli* DH10B using an inducible homologous recombination system. *Gene Therapy*. 6 (3): 442-447, 1999.
20. Murphy, K. C, Campellone, K. G., and Poteete, A. R. (2000) PCR-mediated gene replacement in *Escherichia coli*. *Gene* 246, 321-330.
21. Datsenko, K. A. and Wanner, B. L. (2000) One-step inactivation of chromosomal genes in *Escherichia coli* K-12 using PCR products. *Proc. Natl. Acad. Sci. USA* 97, 6640-6645.

22. Zhang Y, Muyrers J P, Rientjes J and Stewart A F. Phage annealing proteins promote oligonucleotide-directed mutagenesis in *Escherichia coli* and mouse ES cells. *BMC Molecular Biology.* 4 (1): 1-14, 2003.
23. Ellis, H. M., Yu, D., DiTizio, T., and Court, D. L. (2001) High efficiency mutagenesis, repair, and engineering of chromosomal DNA using single-stranded oligonucleotides. *Proc. Natl. Acad. Sci. USA* 98, 6742-6746.
24. see 16 and 17.
25. Fu J, Wenzel S C, Perlova O, Wang J, Gross F, Tang Z, Yin Y, Stewart A F, Müller R, and Zhang Y (2008). Efficient transfer of two large secondary metabolite pathway gene clusters into heterologous hosts by transposition. *Nucleic Acids Res.* 36: e113.
26. Murphy, K. C. (1991) Lambda Gam protein inhibits the helicase and chi-stimulated recombination activities of *Escherichia coli* RecBCD enzyme. *J. Bacteriol.* 173, 5808-5821.
27. Junping Wang, Mihail Sarov, Jeanette Rientjes, Jun Fu, Heike Hollak, Harald Kranz, Wei Xie, A. Francis Stewart and Youming Zhang. An improved recombineering approach by adding RecA to lambda Red recombination. *Molecular Biotechnology.* 32 (1): 43-54, 2006.
28. Clark, A. J. et al. Genes of the RecE and RecF pathways of conjugational recombination in *Escherichia coli*. *Cold Spring Harb. Symp. Quant. Biol.* 49, 453-462 (1984).
29. Hall, S. D., Kane, M. F. & Kolodner, R. D. Identification and characterization of the *Escherichia coli* RecT protein, a protein encoded by the recE region that promotes renaturation of homologous single-stranded DNA. *J. Bacteriol.* 175, 277-287 (1993).
30. Kulkarni S K, Stahl F W. Interaction between the sbcC gene of *Escherichia coli* and the gam gene of phage lambda. *Genetics.* 1989 October; 123 (2): 249-53.
31. Rivero-Müller, A. et al. "Assisted large fragment insertion by Red/ET-recombination (ALFIRE)—an alternative and enhanced method for large fragment recombineering", Nuc. Acids. Res. 2007, 35 (1): e78;
32. Schmidt W. M., Mueller M. W. 1999. CapSelect: a highly sensitive method for 5' CAP-dependent enrichment of full length cDNA in PCRmediated analysis of mRNAs. Nucleic Acids Res. 27 (21): e31.
33. Penfold, R. J. & Pemberton, J. M. An improved suicide vector for construction of chromosomal insertion mutations in bacteria. Gene 118, 145-146 (1992).
34. Kovall R, Matthews B W. Toroidal structure of lambda-exonuclease. *Science.* 1997 Sep. 19; 277 (5333): 1824-7.
35. Zhang J, Xing X, Herr A B, Bell C E. Crystal structure of *E. coli* RecE protein reveals a toroidal tetramer for processing double-stranded DNA breaks. Structure. 2009 May 13; 17 (5): 690-702.
36. Willis, D. K. et al., "Mutation-dependent suppression of recB21 and recC22 by a region cloned from the Rac progphage of *Escherichia coli* K-12", *J. Bacteriol.* 162, 1166-1172.
37. Schmidt, W. M. and Mueller, M. W., 1999, "CapSelect: A highly sensitive method for 5' CAP-dependent enrichment of full length cDNA in PCR mediated analysis of mRNAs", Nuc. Acids. Res. 27 (21): e31.
38. Hashimoto-Gotoh, T. and Sekiguchi, M., 1977, "Mutations of temperature sensitivity in R plasmid pSC101", *J. Bacteriol.* 131, 405-412.
39. Chang A C, Cohen S N. Construction and characterization of amplifiable multicopy DNA cloning vehicles derived from the P15A cryptic miniplasmid. *J Bacteriol.* 1978; 134 (3): 1141-56.
40. Bolivar F, Rodriguez R L, Greene P J, Betlach M C, Heyneker H L, Boyer H W, Crosa J H, Falkow S. Construction and characterization of new cloning vehicles. II. A multipurpose cloning system. *Gene.* 1977; 2 (2): 95-113.
41. Yanisch-Perron C, Vieira J, Messing J. Improved M13 phage cloning vectors and host strains: nucleotide sequences of the M13mp18 and pUC19 vectors. Gene. 1985; 33 (1): 103-19.
42. Gibson D G, et al. *Science.* 2010 May 20 Creation of a Bacterial Cell Controlled by a Chemically Synthesized Genome

The invention claimed is:

1. A host cell comprising one or more nucleic acids encoding a 5' to 3' exonuclease and means for its expression, one or more nucleic acids encoding RecT and means for its expression, and one or more nucleic acids encoding Red gamma and means for its expression,
   wherein the 5' to 3' exonuclease is an N-terminally extended RecE expressed from heterologous DNA that comprises or consists of amino acids 1-866 of SEQ ID NO:1, or a variant of this sequence having at least 95% sequence identity to SEQ ID NO:1 over the entire length of the 866 amino acid sequence,
   said host cell further comprising one or more nucleic acids encoding Red alpha and Red beta and means for their expression,
   wherein the expression of RecE, RecT, Red alpha, and/or Red beta is controlled by different inducible promoters that may be independently temporally expressed.

2. The host cell according to claim 1, further comprising a nucleic acid sequence encoding RecA.

3. The host cell according to claim 1, wherein expression of the 5' to 3' exonuclease is driven by an arabinose inducible promoter or a rhamnose inducible promoter.

4. A kit comprising the host cell according to claim 1 and one or more linearized cloning vectors.

5. The kit according to claim 4, wherein the kit additionally comprises at least one single stranded oligonucleotide.

6. The kit according to claim 5, wherein the at least one single stranded oligonucleotide comprises or consists of DNA.

7. The kit according to claim 5, wherein the at least one single stranded oligonucleotide is 10-100 nucleotides in length.

8. The kit according to claim 7, wherein the at least one single stranded oligonucleotide is about 40 nucleotides in length.

* * * * *

SEQUENCE LISTING

```
<160> NUMBER OF SEQ ID NOS: 2

<210> SEQ ID NO 1
<211> LENGTH: 866
<212> TYPE: PRT
<213> ORGANISM: Escherichia coli K12

<400> SEQUENCE: 1

Met Ser Thr Lys Pro Leu Phe Leu Leu Arg Lys Ala Lys Lys Ser Ser
1               5                   10                  15

Gly Glu Pro Asp Val Val Leu Trp Ala Ser Asn Asp Phe Glu Ser Thr
                20                  25                  30

Cys Ala Thr Leu Asp Tyr Leu Ile Val Lys Ser Gly Lys Lys Leu Ser
            35                  40                  45

Ser Tyr Phe Lys Ala Val Ala Thr Asn Phe Pro Val Val Asn Asp Leu
        50                  55                  60

Pro Ala Glu Gly Glu Ile Asp Phe Thr Trp Ser Glu Arg Tyr Gln Leu
65                  70                  75                  80

Ser Lys Asp Ser Met Thr Trp Glu Leu Lys Pro Gly Ala Ala Pro Asp
                85                  90                  95

Asn Ala His Tyr Gln Gly Asn Thr Asn Val Asn Gly Glu Asp Met Thr
```

```
            100             105             110
Glu Ile Glu Glu Asn Met Leu Leu Pro Ile Ser Gly Gln Glu Leu Pro
        115                 120                 125
Ile Arg Trp Leu Ala Gln His Gly Ser Glu Lys Pro Val Thr His Val
        130                 135                 140
Ser Arg Asp Gly Leu Gln Ala Leu His Ile Ala Arg Ala Glu Glu Leu
145                 150                 155                 160
Pro Ala Val Thr Ala Leu Ala Val Ser His Lys Thr Ser Leu Leu Asp
                165                 170                 175
Pro Leu Glu Ile Arg Glu Leu His Lys Leu Val Arg Asp Thr Asp Lys
            180                 185                 190
Val Phe Pro Asn Pro Gly Asn Ser Asn Leu Gly Leu Ile Thr Ala Phe
        195                 200                 205
Phe Glu Ala Tyr Leu Asn Ala Asp Tyr Thr Asp Arg Gly Leu Leu Thr
        210                 215                 220
Lys Glu Trp Met Lys Gly Asn Arg Val Ser His Ile Thr Arg Thr Ala
225                 230                 235                 240
Ser Gly Ala Asn Ala Gly Gly Asn Leu Thr Asp Arg Gly Glu Gly
                245                 250                 255
Phe Val His Asp Leu Thr Ser Leu Ala Arg Asp Val Ala Thr Gly Val
                260                 265                 270
Leu Ala Arg Ser Met Asp Leu Asp Ile Tyr Asn Leu His Pro Ala His
            275                 280                 285
Ala Lys Arg Ile Glu Glu Ile Ile Ala Glu Asn Lys Pro Pro Phe Ser
        290                 295                 300
Val Phe Arg Asp Lys Phe Ile Thr Met Pro Gly Gly Leu Asp Tyr Ser
305                 310                 315                 320
Arg Ala Ile Val Val Ala Ser Val Lys Glu Ala Pro Ile Gly Ile Glu
                325                 330                 335
Val Ile Pro Ala His Val Thr Glu Tyr Leu Asn Lys Val Leu Thr Glu
                340                 345                 350
Thr Asp His Ala Asn Pro Asp Pro Glu Ile Val Asp Ile Ala Cys Gly
            355                 360                 365
Arg Ser Ser Ala Pro Met Pro Gln Arg Val Thr Glu Glu Gly Lys Gln
        370                 375                 380
Asp Asp Glu Glu Lys Pro Gln Pro Ser Gly Thr Thr Ala Val Glu Gln
385                 390                 395                 400
Gly Glu Ala Glu Thr Met Glu Pro Asp Ala Thr Glu His His Gln Asp
                405                 410                 415
Thr Gln Pro Leu Asp Ala Gln Ser Gln Val Asn Ser Val Asp Ala Lys
            420                 425                 430
Tyr Gln Glu Leu Arg Ala Glu Leu His Glu Ala Arg Lys Asn Ile Pro
        435                 440                 445
Ser Lys Asn Pro Val Asp Asp Lys Leu Leu Ala Ala Ser Arg Gly
        450                 455                 460
Glu Phe Val Asp Gly Ile Ser Asp Pro Asn Asp Pro Lys Trp Val Lys
465                 470                 475                 480
Gly Ile Gln Thr Arg Asp Cys Val Tyr Gln Asn Gln Pro Glu Thr Glu
                485                 490                 495
Lys Thr Ser Pro Asp Met Asn Gln Pro Glu Pro Val Val Gln Gln Glu
                500                 505                 510
Pro Glu Ile Ala Cys Asn Ala Cys Gly Gln Thr Gly Gly Asp Asn Cys
            515                 520                 525
```

```
Pro Asp Cys Gly Ala Val Met Gly Asp Ala Thr Tyr Gln Glu Thr Phe
    530                 535                 540
Asp Glu Glu Ser Gln Val Glu Ala Lys Glu Asn Asp Pro Glu Glu Met
545                 550                 555                 560
Glu Gly Ala Glu His Pro His Asn Glu Asn Ala Gly Ser Asp Pro His
                565                 570                 575
Arg Asp Cys Ser Asp Glu Thr Gly Glu Val Ala Asp Pro Val Ile Val
            580                 585                 590
Glu Asp Ile Glu Pro Gly Ile Tyr Tyr Gly Ile Ser Asn Glu Asn Tyr
        595                 600                 605
His Ala Gly Pro Gly Ile Ser Lys Ser Gln Leu Asp Asp Ile Ala Asp
    610                 615                 620
Thr Pro Ala Leu Tyr Leu Trp Arg Lys Asn Ala Pro Val Asp Thr Thr
625                 630                 635                 640
Lys Thr Lys Thr Leu Asp Leu Gly Thr Ala Phe His Cys Arg Val Leu
                645                 650                 655
Glu Pro Glu Glu Phe Ser Asn Arg Phe Ile Val Ala Pro Glu Phe Asn
            660                 665                 670
Arg Arg Thr Asn Ala Gly Lys Glu Glu Lys Ala Phe Leu Met Glu
        675                 680                 685
Cys Ala Ser Thr Gly Lys Thr Val Ile Thr Ala Glu Glu Gly Arg Lys
    690                 695                 700
Ile Glu Leu Met Tyr Gln Ser Val Met Ala Leu Pro Leu Gly Gln Trp
705                 710                 715                 720
Leu Val Glu Ser Ala Gly His Ala Glu Ser Ser Ile Tyr Trp Glu Asp
                725                 730                 735
Pro Glu Thr Gly Ile Leu Cys Arg Cys Arg Pro Asp Lys Ile Ile Pro
            740                 745                 750
Glu Phe His Trp Ile Met Asp Val Lys Thr Thr Ala Asp Ile Gln Arg
        755                 760                 765
Phe Lys Thr Ala Tyr Tyr Asp Tyr Arg Tyr His Val Gln Asp Ala Phe
    770                 775                 780
Tyr Ser Asp Gly Tyr Glu Ala Gln Phe Gly Val Gln Pro Thr Phe Val
785                 790                 795                 800
Phe Leu Val Ala Ser Thr Thr Ile Glu Cys Gly Arg Tyr Pro Val Glu
                805                 810                 815
Ile Phe Met Met Gly Glu Glu Ala Lys Leu Ala Gly Gln Gln Glu Tyr
            820                 825                 830
His Arg Asn Leu Arg Thr Leu Ser Asp Cys Leu Asn Thr Asp Glu Trp
        835                 840                 845
Pro Ala Ile Lys Thr Leu Ser Leu Pro Arg Trp Ala Lys Glu Tyr Ala
    850                 855                 860
Asn Asp
865

<210> SEQ ID NO 2
<211> LENGTH: 30
<212> TYPE: DNA
<213> ORGANISM: Artificial Sequence
<220> FEATURE:
<223> OTHER INFORMATION: I-SceI recognition site

<400> SEQUENCE: 2
agttacgcta gggataacag ggtaatatag                              30
```